United States Patent [19]

Isogai et al.

[11] Patent Number: 5,677,141

[45] Date of Patent: Oct. 14, 1997

[54] PROCESS FOR PRODUCING 7-AMINOCEPHEM COMPOUND OR SALTS THEREOF

[75] Inventors: Takao Isogai, Ibaraki; Masao Fukagawa, Tsuchiura; Morita Iwami, Tsukuba; Ichiro Aramori, Kyoto; Hitoshi Kojo, Tsuchiura, all of Japan

[73] Assignee: Fujisawa Pharmaceutical Co., Ltd., Osaka, Japan

[21] Appl. No.: 314,309

[22] Filed: Sep. 30, 1994

Related U.S. Application Data

[63] Continuation of Ser. No. 631,906, Dec. 21, 1990, abandoned.

[30] Foreign Application Priority Data

Dec. 27, 1989 [JP] Japan .................................. 1-341113
Jul. 20, 1990 [JP] Japan .................................. 2-193609

[51] Int. Cl.⁶ .............................. C12N 1/21; C12P 15/00; C12P 35/02
[52] U.S. Cl. ................................ 435/47; 435/51; 435/256.4
[58] Field of Search ............................ 435/47, 51, 256.4

[56] References Cited

U.S. PATENT DOCUMENTS

| | | | |
|---|---|---|---|
| 4,141,790 | 2/1979 | Niwa et al. | 435/51 |
| 4,925,794 | 5/1990 | Isogai et al. | 435/252.33 |
| 5,132,218 | 7/1992 | Isogai et al. | 435/172.3 |
| 5,208,155 | 5/1993 | Mosbach et al. | 435/191 |
| 5,354,667 | 10/1994 | Croux et al. | 435/51 |
| 5,424,196 | 6/1995 | Cambiaghi et al. | 435/51 |
| 5,559,005 | 9/1996 | Conder et al. | 435/47 |

FOREIGN PATENT DOCUMENTS

| | | |
|---|---|---|
| 200425 | 12/1986 | European Pat. Off. |
| 63-74488 | 4/1988 | Japan . |

OTHER PUBLICATIONS

American Type Culture Collection Catalogue of Filamentous Fungi, 18th Edition, Amer. Type Culture Collection, Rockville, MD, 1991, pp. 5, 87.

Komatsu et al., Chem. Abstracts 110:113193y (1989).

Deshpande et al., World J. Microbiol. Biotechnol. 10:129–138 (1994).

Matsuda et al., J. Bacteriol. 169:5821–5826 (1987).

Matsuda et al., J. Bacteriol. 169:5815–5820 (1987).

*Primary Examiner*—Robert A. Wax
*Assistant Examiner*—Eric Grimes
*Attorney, Agent, or Firm*—Oblon, Spivak, McClelland, Maier & Neustadt, P.C.

[57] ABSTRACT

The present invention provides a process for producing 7-aminocephem compounds or salts thereof. 7-Aminocephem compounds are produced via microorganisms transformed with a vector containing a gene capable of converting a cephalosporin compound of the formula (II):

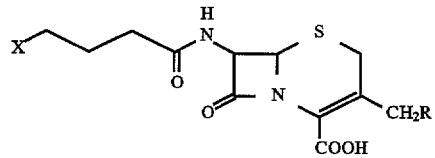

to a 7-aminocephem compound of the formula (I):

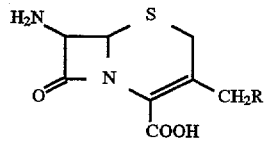

11 Claims, 39 Drawing Sheets

```
       10         20         30         40         50         60
5'-CTCGAGTCGT AMATACATAC AGAAATAGAA TACGACACGT TATACGAGTA CATGACTACA 70         80         90        100        110        120
   TGTGTTGACG AACGCTGAGA CTGTCCGCCA AAGCCCATCT GAGGAAATTA CACGTATCGA 130        140        150        160        170        180
   GGTTTATTGC ACCTGTTTCA AAGATATAGT ACCTACGTAT CTATATACTC ATGCATATAT 190        200        210        220        230        240
   ATTATTAGTG ATAGCCGAAA CACGGGCGAA GATAGTACCC GATTCGACCA TGTCGTCCGC 250        260        270        280        290        300
   CCCTTTACCT CTTGACGTCC CACGATCCGG CTCGCTCCAG ATTGCTACAT TACAGCAACC 310        320        330        340        350        360
   CCCTGGAACA TGTGTGGACA CAACCCACCC AACTGGCCCG GGTCTGAGGC GTCATGATGG 370        380        390        400        410        420
   AAGAGGGTTG GTTACACCGA TACCAGGTGC CAAGGCCGTG CCTCCCATGC GCACCGGCTT 430        440        450        460        470        480
   GTGTCCCCCA GTCGCCGGTT CCCCGGCAAT GGATGGTTGT CGCCCGTCCA CCTCCTCCCC 490        500        510        520        530        540
   CTCCTCCTCC TCCTCCTCCT CCTCCTCTTC CTCATTCTAC CCTGCCCTGC CCCCTTTCTC 550        560        570        580        590        600
   TGTTGAACTT GCCGCTGGAC TTATCCTCCT TCCACATTTC GACTCGTCAT GTATCCTCGG 610        620        630        640        650        660
   CGTGCCTGGT TACCCGGTTG CTTCGCATGG GACTATTGAT TCGGAGCCGT GATGCGTCAG 670        680        690        700        710        720
   TCGACGAGAC CGTGGCCCTG GGAGGGTGGC GTGGACAGCA GAGCACGCCC TCCTGTCTCG 730        740        750        760        770        780
   ACTGGTGGGG TTGGATAGCG GCGAGCACCG GGGGAGTATA GTCCCCTCGG CCGGATGGTT 790        800        810        820        830        840
   ATCAAAGTCT CGCAGTATCA CGAGGGGCCG GTTCCAGATG ACTATATAAG AGGTCCATGG 850        860        870        880        890        900
   TATCCTCCCC TCTCCGTCGA CAGAAGAAGA CTCCTCACCC TCACAGCCTG CCTCCTTCAC 910        920        930        940        950        960
   CGGGTATCAA CCAGCTCTTT TCCCCTCAAC TGCTCACCAA CACCGCCAAC ATGGTCACCC 970        980        990       1000       1010       1020
   TCCGCCGCCT CGCCGTCCTC CTCGGCGCCA TCCCCGCCGC CCTCGCCGCT CCCACCACGC
```

FIG. 1D

```
     1030       1040       1050       1060       1070       1080
AGAAGCGCGA GGTCGTCCCC AACAAGTACA TCGTGACCCT GAAGGAGGGC GCCTCCAACT
     1090       1100       1110       1120       1130       1140
TTGACTCCCA CATCTCCTGG GTCAGCGACA TCCACAAGCG CAGCCTCAGC CGCCGCAGCA
     1150       1160       1170       1180       1190       1200
CCGCCGGTAT CGAGAAGGAG TTCCACATCG ACACCTTTAA CGCCTATGTC GGCGAGTTCG
     1210       1220       1230       1240       1250       1260
ACGAGACTAC CATTGAGGAG ATCAAGAACA ACCCGGATGT GAGTAGTTTT GTCCCTTTCC
     1270       1280       1290       1300       1310       1320
CCCCCCCTTT GTCAACGACA CCCACCACCT TGCAATCAAG CCCGCTGACC AGCTCGTCAC
     1330       1340       1350       1360       1370       1380
TACAAGGTCC TCGAGGTAGA GGAGGACCAG ATCTGGCACC TCTTCGACGA GCAGGACGAG
     1390       1400       1410       1420       1430       1440
GGAGAATTCA GCACCGCCGC CCTCGTCACC CAGAACGGCG CCTGGGGCCT GGGCACCATC
     1450       1460       1470       1480       1490       1500
TCTCATCGCC AGCCTGGCTC GACCAGCTAC ATCTACGACG ACTCGGCCGG CAGCGGCACC
     1510       1520       1530       1540       1550       1560
TACGCCTACG TCGTGGACAC GGGCATCCTC GAGAGTCACA ACGAGTTCTC CGGCCGCGCC
     1570       1580       1590       1600       1610       1620
ATCACGGGCT ACAACGCCGT CGGCGGGAGC AACGCCGACA CCAACGGCCA CGGCACCCAC
     1630       1640       1650       1660       1670       1680
GTCGCTGGCA CCATTGGCGG CAGGACCTAC GGCGTTGCCA AGAACACCAA CCTCATCGCT
     1690       1700       1710       1720       1730       1740
GTCAAGGTCT TCCGGGGATC TTCGAGCTCT ACTTCCATCA TCCTTGACGG CTTCAACTGG
     1750       1760       1770       1780       1790       1800
GCCGTGAACG ATATCATCAA CAGGGGCCGC CAGAACAAGG CTGCCATCAG CATGTCCCTG
     1810       1820       1830       1840       1850       1860
GGTGAGCTAT ACCCCTTTTT TTCCCCTGAC ACCAAAGACA CTCAAATTCC CTTTGCTAAC
     1870       1880       1890       1900       1910       1920
CACAACTAAA CTCCCCCCTT GCAGGTGGTG GCTACTCTTC TGCCTTCAAC AACGCCGTCA
     1930       1940       1950       1960       1970       1980
ACACTGCCTA CTCCCGCGGC GTCCTCTCCG TCGTGGCCGC CGGCAACGAT AACCAGAACG
     1990       2000       2010       2020       2030       2040
CCGCCAACTA CTCCCCCGCC TCGGCCGCCA ACGCCATCAC CGTCGGCTCC ATCGCCTCCA
     2050       2060       2070       2080       2090       2100
ACTGGGCCCG CTCCAGCTTC AGCAACTACG GCTCCGTGCT CGACATCTTC GCCCCCGGAA
     2110       2120       2130       2140       2150       2160
CCAGCATCCT CTCCGCCTGG ATCGGCGGCA ACTCGGCCAC CAACACCATC TCCGGCACCT
     2170       2180       2190       2200       2210       2220
CCATGGCCAC CCCCCATGTC ACCGGCGTCG TCCTCTACCT CCAGGCCCTC GAGGGTCTGA
```

FIG. 1E

```
     2230       2240       2250       2260       2270       2280
CCACCTCTGG CGCTGCCGCC CGCCTCAACG CTCTGGCCAC CACCGGCCGT GTCTCCAACC
     2290       2300       2310       2320       2330       2340
CTGGCTCCGG TAGCCCCAAC CGCATCCTCT ACAACGGCAA CGGTGCCTAG TGCGCACGGG
     2350       2360       2370       2380       2390       2400
CATGGGATAG CCAGTGATGG ATGGTGAAAC GCCATACGGT GAGCGGCTTT CTTGGCCGAT
     2410       2420       2430       2440       2450       2460
AGGGTGGGCG ATCGGGATGG CTTGAGGGTA GCATATATGT ATCTCGGTGA TATTGGGGGG
     2470       2480       2490       2500       2510       2520
GGGGCTAGGA CGCTCCAGAG GACCAGGTTT CTGCTCTTGG TGCTATACCT ACATACGATA
     2530       2540       2550       2560       2570       2580
TACGAATTGA CCGACTTCCA TGATACACAG AGAGTCTTTG TTCCGTTCCA CATGTACCTA
     2590       2600       2610       2620       2630       2640
CGTCCCTACC TCATGGTGTT GCCACGCTGC TCCCAGATAC CAGACGACAT GGTAATAGTA
     2650       2660       2670       2680       2690       2700
GACAAAGTAG ACAACATTGA AGCCGGCACA CACGGGGGTC AAGTATCCCC ATGAGCCATG
     2710       2720       2730       2740       2750       2760
ATGCTTCAAA CAACTAGAAG AATTAGAAGA TATATATGTG TGTACATAGC TATATGTGTT
     2770       2780       2790       2800       2810       2820
ATGCATGTTC CCTCATACCT TCGTTCCCCC CTCCCCTCAC CTCTTCCTCC GACCGATCAG
     2830       2840       2850       2860       2870       2880
CGGCCCGAGT CGCTGTCACT ATTCCTATGT CAAGCTCGGT CATGCTCTCC GACTCGCCAT
     2890       2900       2910       2920       2930       2940
CCTTCTTTAT CCTCCTCGAC ATCTTCGACT GTGTTCCCAT AGGCGAGTCC TGCCCACCTC
     2950       2960       2970       2980       2990       3000
CCATACCCCC ATTCCCGCCA AGATGTATAT CATCGAGGCT GTAGTTGTGG TTACGATGAT
     3010       3020       3030       3040       3050       3060
GCCCACTGCC GCCGTTCATC ATGTCGGCTA GATCACTCTC ATTATCCTTG GCCGCCATAC
     3070       3080       3090       3100       3110       3120
CGCCGACCAG ATCAGCAACC GGTCCGCCGC CCGTGACCAG CGTCGTGCCA CAGGTTCTTG
     3130       3140       3150       3160       3170
CACGCCGTCA CGATGTCGTG GCGTAGATGA GGCAGTTCCA GAAGCCCTGC AG-3'
```

FIG.1F

```
        10         20         30         40         50         60
5'-AGAAGAAGAC TCCTCACCCT CACAGCCTGC CTCCTTCACC GGGTATCAAC CAGCTCTTTT 70         80         90        100        110        120
   CCCCTCAACT GCTCACCAAC ACCGCCAACA TGGTCACCCT CCGCCGCCTC GCCGTCCTCC 130        140        150        160        170        180
   TCGGCGCCAT CCCCGCCGCC CTCGCCGCTC CCACCACGCA GAAGCGCGAG GTCGTCCCCA 190        200        210        220        230        240
   ACAAGTACAT CGTGACCCTG AAGGAGGGCG CCTCCAACTT TGACTCCCAC ATCTCCTGGG 250        260        270        280        290        300
   TCAGCGACAT CCACAAGCGC AGCCTCAGCC GCCGCAGCAC CGCCGGTATC GAGAAGGAGT 310        320        330        340        350        360
   TCCACATCGA CACCTTTAAC GCCTATGTCG GCGAGTTCGA CGAGACTACC ATTGAGGAGA 370        380        390        400        410        420
   TCAAGAACAA CCCGGATGTC CTCGAGGTAG AGGAGGACCA GATCTGGCAC CTCTTCGACG 430        440        450        460        470        480
   AGCAGGACGA GGGAGAATTC AGCACCGCCG CCCTCGTCAC CCAGAACGGC GCCTGGGGCC 490        500        510        520        530        540
   TGGGCACCAT CTCTCATCGC CAGCCTGGCT CGACCAGCTA CATCTACGAC GACTCGGCCG 550        560        570        580        590        600
   GCAGCGGCAC CTACGCCTAC GTCGTGGACA CGGGCATCCT CGAGAGTCAC AACGAGTTCT 610        620        630        640        650        660
   CCGGCCGCGC CATCACGGGC TACAACGCCG TCGGCGGGAG CAACGCCGAC ACCAACGGCC 670        680        690        700        710        720
   ACGGCACCCA CGTCGCTGGC ACCATTGGCG GCAGGACCTA CGGCGTTGCC AAGAACACCA 730        740        750        760        770        780
   ACCTCATCGC TGTCAAGGTC TTCCGGGGAT CTTCGAGCTC TACTTCCATC ATCCTTGACG 790        800        810        820        830        840
   GCTTCAACTG GGCCGTGAAC GATATCATCA ACAGGGGCCG CCAGAACAAG GCTGCCATCA 850        860        870        880        890        900
   GCATGTCCCT GGGTGGTGGC TACTCTTCTG CCTTCAACAA CGCCGTCAAC ACTGCCTACT 910        920        930        940        950        960
   CCCGCGGCGT CCTCTCCGTC GTGGCCGCCG GCAACGATAA CCAGAACGCC GCCAACTACT 970        980        990       1000       1010       1020
   CCCCCGCCTC GGCCGCCAAC GCCATCACCG TCGGCTCCAT CGCCTCCAAC TGGGCCCGCT
```

FIG.1G

```
            1030       1040       1050       1060       1070       1080
       CCAGCTTCAG CAACTACGGC TCCGTGCTCG ACATCTTCGC CCCCGGAACC AGCATCCTCT 1090       1100       1110       1120       1130       1140
       CCGCCTGGAT CGGCGGCAAC TCGGCCACCA ACACCATCTC CGGCACCTCC ATGGCCACCC 1150       1160       1170       1180       1190       1200
       CCCATGTCAC CGGCGTCGTC CTCTACCTCC AGGCCCTCGA GGGTCTGACC ACCTCTGGCG 1210       1220       1230       1240       1250       1260
       CTGCCGCCCG CCTCAACGCT CTGGCCACCA CCGGCCGTGT CTCCAACCCT GGCTCCGGTA 1270       1280       1290       1300       1310       1320
       GCCCCAACCG CATCCTCTAC AACGGCAACG GTGCCTAGTG CGCACGGGCA TGGGATAGCC 1330       1340       1350       1360       1370       1380
       AGTGATGGAT GGTGAAACGC CATACGGTGA GCGGCTTTCT TGGCCGATAG GGTGGGCGAT 1390       1400       1410       1420       1430       1440
       CGGGATGGCT TGAGGGTAGC ATATATGTAT CTCGGTGATA TTGGGGGGGG GGCTAGGACG 1450       1460       1470       1480       1490       1500
       CTCCAGAGGA CCAGGTTTCT GCTCTTGGTG CTATACCTAC ATACGATATA CGAATTGACC

1510
       GACTTCCATG ATA-3'
```

FIG.1H

```
       10        20        30        40        50        60
5'-GAATTCCGGGGGGGGGGGGGGGGGGGGGGAGAAGAAGACTCCTCACCCTCACAGCCTGCCT
   GluPheArgGlyGlyGlyGlyGlyGlyGluLysLysThrProHisProHisSerLeuPro 70        80        90       100       110       120
   CCTTCACCGGGTATCAACCAGCTCTTTTCCCCTCAACTGCTCACCAACACCGCCAACATG
   ProSerProGlyIleAsnGlnLeuPheSerProGlnLeuLeuThrAsnThrAlaAsnMet 130       140       150       160       170       180
   GTCACCCTCCGCCGCCTCGCCGTCCTCCTCGGCGCCATCCCCGCCGCCCTCGCCGCTCCC
   ValThrLeuArgArgLeuAlaValLeuLeuGlyAlaIleProAlaAlaLeuAlaAlaPro 190       200       210       220       230       240
   ACCACGCAGAAGCGCGAGGTCGTCCCCAACAAGTACATCGTGACCCTGAAGGAGGGCGCC
   ThrThrGlnLysArgGluValValProAsnLysTyrIleValThrLeuLysGluGlyAla 250       260       270       280       290       300
   TCCAACTTTGACTCCCACATCTCCTGGGTCAGCGACATCCACAAGCGCAGCCTCAGCCGC
   SerAsnPheAspSerHisIleSerTrpValSerAspIleHisLysArgSerLeuSerArg 310       320       330       340       350       360
   CGCAGCACCGCCGGTATCGAGAAGGAGTTCCACATCGACACCTTTAACGCCTATGTCGGC
   ArgSerThrAlaGlyIleGluLysGluPheHisIleAspThrPheAsnAlaTyrValGly 370       380       390       400       410       420
   GAGTTCGACGAGACTACCATTGAGGAGATCAAGAACAACCCGGATGTCCTCGAGGTAGAG
   GluPheAspGluThrThrIleGluGluIleLysAsnAsnProAspValLeuGluValGlu 430       440       450       460       470       480
   GAGGACCAGATCTGGCACCTCTTCGACGAGCAGGACGAGGGAGAATTCAGCACCGCCGCC
   GluAspGlnIleTrpHisLeuPheAspGluGlnAspGluGlyGluPheSerThrAlaAla 490       500       510       520       530       540
   CTCGTCACCCAGAACGGCGCCTGGGGCCTGGGCACCATCTCTCATCGCCAGCCTGGCTCG
   LeuValThrGlnAsnGlyAlaTrpGlyLeuGlyThrIleSerHisArgGlnProGlySer 550       560       570       580       590       600
   ACCAGCTACATCTACGACGACTCGGCCGGCAGCGGCACCTACGCCTACGTCGTGGACACG
   ThrSerTyrIleTyrAspAspSerAlaGlySerGlythrTyrAlaTyrValValAspThr 610       620       630       640       650       660
   GGCATCCTCGAGAGTCACAACGAGTTCTCCGGCCGCGCCATCACGGGCTACAACGCCGTC
   GlyIleLeuGluSerHisAsnGluPheSerGlyArgAlaIleThrGlyTyrAsnAlaVal 670       680       690       700       710       720
   GGCGGGAGCAACGCCGACACCAACGGCCACGGCACCCACGTCGCTGGCACCATTGGCGGC
   GlyGlySerAsnAlaAspThrAsnGlyHisGlyThrHisValAlaGlyThrIleGlyGly 730       740       750       760       770       780
   AGGACCTACGGCGTTGCCAAGAACACCAACCTCATCGCTGTCAAGGTCTTCCGGGGATCT
   ArgThrTyrGlyValAlaLysAsnThrAsnLeuIleAlaValLysValPheArgGlySer 790       800       810       820       830       840
   TCGAGCTCTACTTCCATCATCCTTGACGGCTTCAACTGGGCCGTGAACGATATCATCAAC
   SerSerSerThrSerIleIleLeuAspGlyPheAsnTrpAlaValAsnAspIleIleAsn
```

FIG. 1I

```
           850       860       870       880       890       900
AGGGGCCGCCAGAACAAGGCTGCCATCAGCATGTCCCTGGGTGGTGGCTACTCTTCTGCC
ArgGlyArgGlnAsnLysAlaAlaIleSerMetSerLeuGlyGlyGlyTyrSerSerAla 910       920       930       940       950       960
TTCAACAACGCCGTCAACACTGCCTACTCCCGCGGCGTCCTCTCCGTCGTGGCCGCCGGC
PheAsnAsnAlaValAsnThrAlaTyrSerArgGlyValLeuSerValValAlaAlaGly 970       980       990      1000      1010      1020
AACGATAACCAGAACGCCGCCAACTACTCCCCCGCCTCGGCCGCCAACGCCATCACCGTC
AsnAspAsnGlnAsnAlaAlaAsnTyrSerProAlaSerAlaAlaAsnAlaIleThrVal 1030      1040      1050      1060      1070      1080
GGCTCCATCGCCTCCAACTGGGCCCGCTCCAGCTTCAGCAACTACGGCTCCGTGCTCGAC
GlySerIleAlaSerAsnTrpAlaArgSerSerPheSerAsnTyrGlySerValLeuAsp 1090      1100      1110      1120      1130      1140
ATCTTCGCCCCCGGAACCAGCATCCTCTCCGCCTGGATCGGCGGCAACTCGGCCACCAAC
IlePheAlaProGlyThrSerIleLeuSerAlaTrpIleGlyGlyAsnSerAlaThrAsn 1150      1160      1170      1180      1190      1200
ACCATCTCCGGCACCTCCATGGCCACCCCCCATGTCACCGGCGTCGTCCTCTACCTCCAG
ThrIleSerGlyThrSerMetAlaThrProHisValThrGlyValValLeuTyrLeuGln 1210      1220      1230      1240      1250      1260
GCCCTCGAGGGTCTGACCACCTCTGGCGCTGCCGCCCGCCTCAACGCTCTGGCCACCACC
AlaLeuGluGlyLeuThrThrSerGlyAlaAlaAlaArgLeuAsnAlaLeuAlaThrThr 1270      1280      1290      1300      1310      1320
GGCCGTGTCTCCAACCCTGGCTCCGGTAGCCCCAACCGCATCCTCTACAACGGCAACGGT
GlyArgValSerAsnProGlySerGlySerProAsnArgIleLeuTyrAsnGlyAsnGly 1330      1340      1350      1360      1370      1380
GCCTAGTGCGCACGGGCATGGGATAGCCAGTGATGGATGGTGAAACGCCATACGGTGAGC
Ala***

1390      1400      1410      1420      1430      1440
GGCTTTCTTGGCCGATAGGGTGGGCGATCGGGATGGCTTGAGGGTAGCATATATGTATCT 1450      1460      1470      1480      1490      1500
CGGTGATATTGGGGGGGGGGCTAGGACGCTCCAGAGGACCAGGTTTCTGCTCTTGGTGCT 1510      1520      1530      1540
ATACCTACATACGATATACGAATTGACCGACTTCCATGATAAAAAA-3'
```

FIG.1J

```
5'-ATGGTCACCCTCCGCCGCCTCGCCGTCCTCCTCGGCGCCATCCCCGCCGCCCTCGCCGCT    60
   MetValThrLeuArgArgLeuAlaValLeuLeuGlyAlaIleProAlaAlaLeuAlaAla   -98

CCCACCACGCAGAAGCGCGAGGTCGTCCCCAACAAGTACATCGTGACCCTGAAGGAGGGC   120
   ProThrThrGlnLysArgGluValValProAsnLysTyrIleValThrLeuLysGluGly   -78

GCCTCCAACTTTGACTCCCACATCTCCTGGGTCAGCGACATCCACAAGCGCAGCCTCAGC   180
   AlaSerAsnPheAspAerHisIleSerTrpValSerAspIleHisLysArgSerLeuSer   -58

CGCCGCAGCACCGCCGGTATCGAGAAGGAGTTCCACATCGACACCTTTAACGCCTATGTC   240
   ArgArgSerThrAlaGlyIleGluLysGluPheHisIleAspThrPheAsnAlaTyrVal   -38

GGCGAGTTCGACGAGACTACCATTGAGGAGATCAAGAACAACCCGGATGTCCTCGAGGTA   300
   GlyGluPheAspGluThrThrIleGluGluIleLysAsnAsnProAspValLeuGluVal   -18

GAGGAGGACCAGATCTGGCACCTCTTCGACGAGCAGGACGAGGGAGAATTCAGCACCGCC   360
   GluGluAspGlnIleTrpHisLeuPheAspGluGlnAspGluGlyGluPheSerThrAla     3

GCCCTCGTCACCCAGAACGGCGCCTGGGGCCTGGGCACCATCTCTCATCGCCAGCCTGGC   420
   AlaLeuValThrGlnAsnGlyAlaTrpGlyLeuGlyThrIleSerHisArgGlnProGly    23

TCGACCAGCTACATCTACGACGACTCGGCCGGCAGCGGCACCTACGCCTACGTCGTGGAC   480
   SerThrSerTyrIleTyrAspAspSerAlaGlySerGlyThrTyrAlaTyrValValAsp    43

ACGGGCATCCTCGAGAGTCACAACGAGTTCTCCGGCCGCGCCATCACGGGCTACAACGCC   540
   ThrGlyIleLeuGluSerHisAsnGluPheSerGlyArgAlaIleThrGlyTyrAsnAla    63

GTCGGCGGGAGCAACGCCGACACCAACGGCCACGGCACCCACGTCGCTGGCACCATTGGC   600
   ValGlyGlySerAsnAlaAspThrAsnGlyHisGlyThrHisValAlaGlyThrIleGly    83

GGCAGGACCTACGGCGTTGCCAAGAACACCAACCTCATCGCTGTCAAGGTCTTCCGGGGA   660
   GlyArgThrTyrGlyValAlaLysAsnThrAsnLeuIleAlaValLysValPheArgGly   103

TCTTCGAGCTCTACTTCCATCATCCTTGACGGCTTCAACTGGGCCGTGAACGATATCATC   720
   SerSerSerSerThrSerIleIleLeuAspGlyPheAsnTrpAlaValAsnAspIleIle   123

AACAGGGGCCGCCAGAACAAGGCTGCCATCAGCATGTCCCTGGGTGGTGGCTACTCTTCT   780
   AsnArgGlyArgGlnAsnLysAlaAlaIleSerMetSerLeuGlyGlyGlyTyrSerSer   143

GCCTTCAACAACGCCGTCAACACTGCCTACTCCCGCGGCGTCCTCTCCGTCGTGGCCGCC   840
   AlaPheAsnAsnAlaValAsnThrAlaTyrSerArgGlyValLeuSerValValAlaAla   163

GGCAACGATAACCAGAACGCCGCCAACTACTCCCCCGCCTCGGCCGCCAACGCCATCACC   900
   GlyAsnAspAsnGlnAsnAlaAlaAsnTyrSerProAlaSerAlaAlaAsnAlaIleThr   183

GTCGGCTCCATCGCCTCCAACTGGGCCCGCTCCAGCTTCAGCAACTACGGCTCCGTGCTC   960
   ValGlySerIleAlaSerAsnTrpAlaArgSerSerPheSerAsnTyrGlySerValLeu   203

GACATCTTCGCCCCCGGAACCAGCATCCTCTCCGCCTGGATCGGCGGCAACTCGGCCACC  1020
   AspIlePheAlaProGlyThrSerIleLeuSerAlaTrpIleGlyGlyAsnSerAlaThr   223

AACACCATCTCCGGCACCTCCATGGCCACCCCCCATGTCACCGGCGTCGTCCTCTACCTC  1080
   AsnThrIleSerGlyThrSerMetAlaThrProHisValThrGlyValValLeuTyrLeu   243

CAGGCCCTCGAGGGTCTGACCACCTCTGGCGCTGCCGCCCGCCTCAACGCTCTGGCCACC  1140
   GlnAlaLeuGluGlyLeuThrThrSerGlyAlaAlaAlaArgLeuAsnAlaLeuAlaThr   263

ACCGGCCGTGTCTCCAACCCTGGCTCCGGTAGCCCCAACCGCATCCTCTACAACGGCAAC  1200
   ThrGlyArgValSerAsnProGlySerGlySerProAsnArgIleLeuTyrAsnGlyAsn   283

GGTGCCTAG-3'                                                  1209
   GlyAla***                                                      285
```

FIG. 1K

```
         10         20         30         40         50         60
5'-GAATTCGGGG GTCTGAGGCG TCATGATGGA AGAGGGTTGG TTACACCGAT ACCAGGTGCC
         70         80         90        100        110        120
   AAGGCCGTGC CTCCCATGCG CACCGGCTTG TGTCCCCCAG TCGCCGGTTC CCCGGCAATG
        130        140        150        160        170        180
   GATGGTTGTC GCCCGTCCAC GTCCTCCCCC TCCTCCTCCT CCTCCTCCTC GTCCTCTTCC
        190        200        210        220        230        240
   TCATTCTACC CTGCCCTGCC CCCTTTCTCT GTTGAACTTG CCGCTGGACT TATCCTCCTT
        250        260        270        280        290        300
   CCACATTTCG ACTCGTCATG TATCCTCGGC GTGCCTGGTT ACCCGGTTGC TTCGCATGGG
        310        320        330        340        350        360
   ACTATTGATT CGGAGCCGTG ATGCGTCAGT CGACGAGACC GTGGCCCTGG GAGGGTGGCG
        370        380        390        400        410        420
   TGGACAGCAG AGCACGCCCT CCTGTCTCGA CTCGTGGGGT TGGATAGCGG CGAGCACCGG
        430        440        450        460        470        480
   GGGAGTATAG TCCCCTCGGC CGGATGGTTA TCAAAGTCTC GCAGTATCAC GAGGGGCCGG
        490        500        510        520        530        540
   TTCCAGATGA CTATATAAGA GGTCCATGGT ATCCTCCCCT CTCCGTCGAC AGAAGAAGAC
        550        560        570        580        590
   TCCTCACCCT CACAGCCTGC CTCCTTCACC GGGTATCAAC CAGCGGATCC-3'
```

FIG.1M

```
        10         20         30         40         50         60
5'-GGATCCGGCC ACCACCGGCC GTGTCTCCAA CCCTGGCTCC GGTAGCCCCA ACCGCATCCT 70         80         90        100        110        120
CTACAACGGC AACGGTGCCT AGTGCGCACG GGCATGGGAT AGCCAGTGAT GGATGGTGAA 130        140        150        160        170        180
ACGCCATACG GTGAGCGGCT TTCTTGGCCG ATTGGGTGGG CGATCGGGAT GGCTTGAGGG 190        200        210        220        230        240
TAGCATATAT GTATCTCGGT GATATTGGCG GGGGGGCTAC GACGCTCCAG AGGACCAGGT 250        260        270        280        290        300
TTCTGCTCTT GGTGCTATAC CTACATACGA TATACGAATT GACCGACTTC CATGATACAC 310        320        330        340        350        360
AGAGAGTCTT TGTTCCGTTC CACATGTACC TACGTCCCTA CCTCATGGTG TTGCCACGCT 370        380        390        400        410        420
GCTCCCAGAT ACCAGACGAC ATGGTAATAG TAGACAAAGT AGACAACATT GAAGCCGGCA 430        440        450        460        470        480
CACACGGGGG TCAAGTATCC CCATGAGCCA TGATGCTTCA AACAACTAGA AGAATTAGAA 490        500        510        520        530        540
GATATATATG TGTGTACATA GCTATATGTG TTATGCATGT TCCCTCATAC CTTCGTTCCC 550        560        570        580        590        600
CCCTCCCCTC ACCTCTTCCT CCGACCGATC AGCGGCCCGA GTCGCTGTCA CTATTCCTAT 610        620        630        640        650        660
GTCAAGCTCG GTCATGCTCT CCGACTCGCC ATCCTTCTTT ATCCTCCTCG ACATCTTCGA 670        680        690        700        710        720
CTGTGTTCCC ATAGGCGAGT CCTGCCCACC TCCCATACCC CCATTCCCGC CAAGATGTAT 730        740        750        760        770        780
ATCATCGAGG CTGTAGTTGT GGTTACGATG ATGCCCACTG CCGCCGTTCA TCATGTCGGC 790        800        810        820        830        840
TAGATCACTC TCATTATCCT TGGCCGCCAT ACCGCCGACC AGATCAGCAA CCGGTCCGCC 850        860        870        880        890        900
GCCCGTGACC AGCGTCGTGC CACAGGTTCT TGCACGCCGT CACGATGTCG TGGCGTAGAT 910        920        930
GAGGCAGTTC CAGAAGCCCT GCAGGCATGC AAGCTT-3'
```

FIG.1N

```
        10         20         30         40         50         60
5'-GTCGACTACC GGTGAGCCGC TCGACGGGGC GTCGAGTTGC CGGGCCCAAT CCCTGAGCTT 70         80         90        100        110        120
   CGATAGACTG TTCCGGGCCT CATGTGGGTG GCGGCGTCTA CATGCACATG CATAACGGCG 130        140        150        160        170        180
   TTCCTCATCG CTTGGCCCCG CATGCAGTCT TCAGGGACCA AACTCCATCG CCGCTGCTGG 190        200        210        220        230        240
   ACCGTATGTA ACCCCCCTCG GCAGTGCACC CGCAGGAGCC GGATAATCGA GACCTTGGCA 250        260        270        280        290        300
   GGCCATAAAG GCGCGTCGTG GGGAAGCTCA TATCGTATAG CAACGGGAGA CACGAGGTAG 310        320        330        340        350        360
   GTACTCAAGT ACACATACAC ACACCCAGCC GCCCGTATAA ACAGCTTCAA GAGGGGCGAA 370        380        390        400        410        420
   TACTTGAATA TCCCTTTGGT CGCTCTTCTG ATTTTCGAGG CTTCTCCTTC CGCCATCGTC 430        440        450        460        470
   ACTCACGCAT ATCTCGTCTT TCACATCTTA CACCAGGCAG GACAAACCGT CACCATGG-3'
```

FIG.1Q

```
        10         20         30         40         50         60
5'-TGATCAACAA GAATGGTCAG ACCTAAATCG GTCGATCAGG TTCGGCTGAT CTGCCGCTGT 70         80         90        100        110        120
GGGCGGGCGT GCGGAGGAAT GCGGGAGTAA AAGCAGTTCA AGGGGCCGGA AGGGTCGAGT 130        140        150        160        170        180
GTCTGCCAGG AAGAATCAGT CCTTCTCCGC CCCCTTTTTT TTTTCCCCTT GCCGGCTATG 190        200        210        220        230        240
TTAAACCACC AGCAATCGAA CCCTTTTTCT CCCATCAGTA TGCTCTGGAG TGTACCCTCT 250        260        270        280        290        300
ATGTACATGT AGTGAAACAG GCTAAATTTG CTGCCCCGTG TGCATGTATC AATGATGCGT 310        320        330        340        350        360
TTCCTGCGTC CATGTCTGAC TGTAGTTGTA CACGTACACC ACACCATTGT CTACCCCCCG 370        380        390        400        410        420
CGACGTATGT ACGTATTGAT CTATGATGTG CATATTCAAC GCTAACTATT TTTACCTCGG 430        440        450        460        470        480
ACAGATTCCA GAATGCTACC GTAAGCCATC ATGAACCCAT GAACCACGGT GGATCTAGCC 490        500        510        520        530        540
CGGTCATCCC TGCCTCCCTG CCACAGTGCG GGTCATCTCC TGGGGCCGAG CACACGAGAG 550        560        570        580        590        600
GCCGAATTGG CGTTCAGTCG GCCATGAGGC CGCTTGCGAT CCCTTGTGGG ATTGAAGATC 610        620        630        640        650        660
CGTCGTCGAA ATTCAGCCGC CGAGATACCC TATATCGATT CATAGATACC AATATCCGCA 670        680        690        700        710        720
CTGGTAGACG TTCTTGGACA GTCCATGCAG GCGAGCTGCC TCTCTCTCTC TCTCTTTTTT 730        740        750        760        770        780
TTTTTTTTTC TTTAGTTGCA GTTATTGCAG TCTGACTGTG ACCCTGGCAC TTGGCAAGCC 790        800        810        820        830        840
ACCGGTTCGC GAGTTATTTC ATTCCGGTGC TTCTCCCGTC GATAGCGCAG GGATGGGAGG 850        860        870        880        890        900
GAGGGGAGTA GGGTAAGGGG GGTTGGTGTG GGGAGTGTCG AACCAAAAAA TGACGGGAGC 910        920        930        940        950        960
TCGGATACAG CTTCCTCGCA CGCGCTGTGT ACTCCTACAT ACATGTATAT GCTTTCTAAC 970        980        990       1000       1010
AGGGACCGAG ACTTATTTAG GTAAGGATCA AGGATCGATC CCCGGGGAGC TCGAATTC -3'
```

FIG.1T

```
                                      5'-GGATCCACAGGAAACAGCT
       10        20        30        40        50        60
ATGAAAAAGCCTGAACTCACCGCGACGTCTGTCGAGAAGTTTCTGATCGAAAAGTTCGAC
MetLysLysProGluLeuThrAlaThrSerValGluLysPheLeuIleGluLysPheAsp 70        80        90       100       110       120
AGCGTCTCCGACCTGATGCAGCTCTCGGAGGGCGAAGAATCTCGTGCTTTCAGCTTCGAT
SerValSerAspLeuMetGlnLeuSer Glu GlyGluGluSerArgAlaPheSerPheAsp 130       140       150       160       170       180
GTAGGAGGGCGTGGATATGTCCTGCGGGTAAATAGCTGCGCCGATGGTTTCTACAAAGAT
ValGlyGlyArgGlyTyrValLeuArgValAsnSerCysAlaAspGlyPheTyrLysAsp 190       200       210       220       230       240
CGTTATGTTTATCGGCACTTTGCATCGGCCGCGCTCCCGATTCCGGAAGTGCTTGACATT
ArgTyrValTyrArgHisPheAlaSerAlaAlaLeuProIleProGluValLeuAspIle 250       260       270       280       290       300
GGGGAATTC/  GAGAGCCTGACCTATTGCATCTCCCGCCGTGCACAGGGTGTCACGTTG
GlyGluPheSerGluSerLeuThrTyr CysIleSerArgArgAlaGlnGlyValThrLeu 310       320       330       340       350       360
CAAGACCTGCCTGAAACCGAACTGCCCGCTGTTCTGCAGCCGGTCGCGGAGGCCATGGAT
GlnAspLeuProGlu ThrGluLeuProAlaValLeuGlnProValAlaGluAlaMetAsp 370       380       390       400       410       420
GCGATCGCTGCGGCCGATCTTAGCCAGACGAGCGGGTTCGGCCCATTCGGACCGCAAGGA
AlaIleAlaAlaAlaAspLeuSerGlnThrSerGlyPheGlyProPheGlyProGlnGly 430       440       450       460       470       480
ATCGGTCAATACACTACATGGCGTGATTTCATATGCGCGATTGCTGATCCCCATGTGTAT
IleGlyGlnTyrThrThrTrpArgAspPheIleCysAlaIleAlaAspProHisValTyr 490       500       510       520       530       540
CACTGGCAAACTGTGATGGACGACACCGTCAGTGCGTCCGTCGCGCAGGCTCTCGATGAG
HisTrpGlnThrValMetAspAspThrValSerAlaSerValAlaGlnAlaLeuAspGlu 550       560       570       580       590       600
CTGATGCTTTGGGCCGAGGACTGCCCCGAAGTCCGGCACCTCGTGCACGCGGATTTCGGC
LeuMetLeuTrpAlaGluAspCysProGluValArgHisLeuValHisAlaAspPheGly
```

FIG.2B

```
      610       620       630       640       650       660
TCCAACAATGTCCTGACGGACAATGGCCGCATAACAGCGGTCATTGACTGGAGCGAGGCG
SerAsnAsnValLeuThrAspAsnGlyArgIleThrAlaValIleAspTrpSerGluAla 670       680       690       700       710       720
ATGTTCGGGGATTCCCAATACGAGGTCGCCAACATCTTCTTCTGGAGGCCGTGGTTGGCT
MetPheGlyAspSerGlnTyrGluValAlaAsnIlePhePheTrpArgProTrpLeuAla 730       740       750       760       770       780
TGTATGGAGCAGCAGACGCGCTACTTCGAGCGGAGGCATCCGGAGCTTGCAGGATCGCCG
CysMetGluGlnGlnThrArgTyrPheGluArgArgHisProGluLeuAlaGlySerPro 790       800       810       820       830       840
CGGCTCCGGGCGTATATGCTCCGCATTGGTCTTGACCAACTCTATCAGAGCTTGGTTGAC
ArgLeuArgAlaTyrMetLeuArgIleGlyLeuAspGlnLeuTyrGlnSerLeuValAsp 850       860       870       880       890       900
GGCAATTTCGATGATGCAGCTTGGGCGCAGGGTCGATGCGACGCAATCGTCCGATCCGGA
GlyAsnPheAspAspAlaAlaTrpAlaGlnGlyArgCysAspAlaIleValArgSerGly 910       920       930       940       950       960
GCCGGGACTGTCGGGCGTACACAAATCGCCCGCAGAAGCGCGGCCGTCTGGACCGATGGC
AlaGlyThrValGlyArgThrGlnIleAlaArgArgSerAlaAlaValTrpThrAspGly 970       980       990      1000      1010      1020
TGTGTAGAAGTACTCGCCGATAGTGGAAACCGACGCCCCAGCACTCGTCCGAGGGCAAAG
CysValGluValLeuAlaAspSerGlyAsnArgArgProSerThrArgProArgAlaLys

GAATAGAGTAGATGCCGACCGGGATCC -3'
Glu***
```

FIG.2C

```
5'-ATGACTATGGCTGCCAACACCGATCGCGCGGTCTTGCAGGCGGCGCTGCCGCCGCTTTCC      60
   MetThrMetAlaAlaAsnThrAspArgAlaValLeuGlnAlaAlaLeuProProLeuSer      19

GGCAGCCTCCCCATTCCCGGATTGAGCGCGTCGGTCCGTATCCAGCGCGATGCCTGGGGC     120
   GlySerLeuProIleProGlyLeuSerAlaSerValArgIleGlnArgAspAlaTrpGly      39

ATCCCGCATATCAAGGCCTCCGGCGAGGCCGATGCCTATCGCGCGCTGGGCTTCGTCCAT     180
   IleProHisIleLysAlaSerGlyGluAlaAspAlaTyrArgAlaLeuGlyPheValHis      59

GCGCAGGACCGCCTTTTCCAGATGGAGCTGACGCGTCGCAAGGCGCTGGGACGCGCGGCC     240
   AlaGlnAspArgLeuPheGlnMetGluLeuThrArgArgLysAlaLeuGlyArgAlaAla      79

GAATGGCTGGGTGCCGAGGCCGCCGAGGCCGATATCCTCGTGCGCCGGCTCGGTATGGAA     300
   GluTrpLeuGlyAlaGluAlaAlaGluAlaAspIleLeuValArgArgLeuGlyMetGlu      99

AAAGTCTGCCGACGCGATTTCGAGGCCCTGGGCGCCGAGGCGAAGGACATGCTCCGGGCC     360
   LysValCysArgArgAspPheGluAlaLeuGlyAlaGluAlaLysAspMetLeuArgAla     119

TACGTCGCCGGCGTGAACGCATTCCTGGCTTCCGGTGTTCCCCTGCCTGTCGAATACGGA     420
   TyrValAlaGlyValAsnAlaPheLeuAlaSerGlyValProLeuProValGluTyrGly     139

TTGCTCGGAGCAGAGCCGGAGCCCTGGGAGCCTTGGCACAGCATCGCGGTGATGCGCCGG     480
   LeuLeuGlyAlaGluProGluProTrpGluProTrpHisSerIleAlaValMetArgArg     159

CTGGGCCTGCTGATGGGTTCGGTCTGGTTCAAGCTCTGGCGGATGCTGGCGCTGCCGGTG     540
   LeuGlyLeuLeuMetGlySerValTrpPheLysLeuTrpArgMetLeuAlaLeuProVal     179

GTCGGAGCCGCGAATGCGCTGAAGCTGCGCTATGACGATGGCGGCCGCGATTTGCTCTGC     600
   ValGlyAlaAlaAsnAlaLeuLysLeuArgTyrAspAspGlyGlyArgAspLeuLeuCys     199

ATCCCGCCGGGCGCCGAAGCGGATCGGCTCGAGGCGGATCTCGCGACCCTGCGGCCCGCG     660
   IleProProGlyAlaGluAlaAspArgLeuGluAlaAspLeuAlaThrLeuArgProAla     219

GTCGATGCGCTGCTGAAGGCGATGGGCGGGGATGCCTCAGATGCCGCCGGTGGCGGCAGC     720
   ValAspAlaLeuLeuLysAlaMetGlyGlyAspAlaSerAspAlaAlaGlyGlyGlySer     239

AACAACTGGGCGGTCGCGCCGGGCCGTACGGCGACCGGCCGGCCGATCCTCGCGGGCGAT     780
   AsnAsnTrpAlaValAlaProGlyArgThrAlaThrGlyArgProIleLeuAlaGlyAsp     259

CCGCATCGCGTCTTCGAGATCCCCGGCATGTATGCCCAGCATCATCTGGCCTGCGATCGC     840
   ProHisArgValPheGluIleProGlyMetTyrAlaGlnHisHisLeuAlaCysAspArg     279

TTCGACATGATCGGCCTGACCGTGCCGGGCGTGCCGGGTTTTCCGCATTTCGCGCATAAC     900
   PheAspMetIleGlyLeuThrValProGlyValProGlyPheProHisPheAlaHisAsn     299

GGCAAGGTCGCCTACTGCGTCACCCATGCCTTCATGGACATTCACGATCTCTACCTTGAG     960
   GlyLysValAlaTyrCysValThrHisAlaPheMetAspIleHisAspLeuTyrLeuGlu     319

CAGTTCGCGGAGGAGGGCCGCAGGGCGCGGTTCGGCAACGATTTCGAGCCCGCCGCCTGG    1020
   GlnPheAlaGluGluGlyArgArgAlaArgPheGlyAsnAspPheGluProAlaAlaTrp     339

AGCCGGGACCGTATCGCGGTCCGGGGTGGTGCCGACCGCGAATTCGATATCATCGAGACG    1080
   SerArgAspArgIleAlaValArgGlyGlyAlaAspArgGluPheAspIleIleGluThr     359

CGCCATGGTCCCGTCATAGCAGGCGATCCGCGCGATGGCGCAGCGCTCACGCTGCGCTCG    1140
   ArgHisGlyProValIleAlaGlyAspProArgAspGlyAlaAlaLeuThrLeuArgSer     379
```

FIG. 3G

```
GTCCAGTTCGCCGAGACCGATCTGTCCTTCGATTGCCTGACGCGGATGCCGGGCGCATCG    1200
ValGlnPheAlaGluThrAspLeuSerPheAspCysLeuThrArgMetProGlyAlaSer     399

ACCGTGGCGCAGCTCTACGACGCGACGCGCGGCTGGGGCCTGATCGACCATAATCTCGTC    1260
ThrValAlaGlnLeuTyrAspAlaThrArgGlyTrpGlyLeuIleAspHisAsnLeuVal     419

GCCGGGGATGTCGGGGGCTCGATCGGCCATCTGGTCCGCGCCCGTGTCCCGTCCCGCTCG    1320
AlaGlyAspValGlyGlySerIleGlyHisLeuValArgAlaArgValProSerArgSer     439

CGCGAAAACGGCTGGCTGCCGGTGCCGGGCTGGTCCGGCGAGCATGAATGGCGGGGTTGG    1380
ArgGluAsnGlyTrpLeuProValProGlyTrpSerGlyGluHisGluTrpArgGlyTrp     459

ATTCCGCACGAGGCGATGCCGCGCGTGATCGATCCGCCGGGCGGCATCATCGTCACGGCG    1440
IleProHisGluAlaMetProArgValIleAspProProGlyGlyIleIleValThrAla     479

AATAATCGCGTCGTGGCCGATGACCATCCCGATTATCTCTGCACCGATTGCCATCCGCCC    1500
AsnAsnArgValValAlaAspAspHisProAspTyrLeuCysThrAspCysHisProPro     499

TACCGCGCCGAGCGCATCATGAAGCGCCTGGTCGCCAATCCGGCTTTCGCCGTCGACGAT    1560
TyrArgAlaGluArgIleMetLysArgLeuValAlaAsnProAlaPheAlaValAspAsp     519

GCCGCCGCGATCCATGCCGATACGCTGTCGCCCCATGTCGGGTTGCTGCGCCGGAGGCTC    1620
AlaAlaAlaIleHisAlaAspThrLeuSerProHisValGlyLeuLeuArgArgArgLeu     539

GAGGCGCTTGGAGCCCGCGACGACTCCGCGGCCGAAGGGCTGAGGCAGATGCTCGTCGCC    1680
GluAlaLeuGlyAlaArgAspAspSerAlaAlaGluGlyLeuArgGlnMetLeuValAla     559

TGGGACGGCCGCATGGATGCGGCTTCGGAGGTCGCGTCTGCCTACAATGCGTTCCGCAGG    1740
TrpAspGlyArgMetAspAlaAlaSerGluValAlaSerAlaTyrAsnAlaPheArgArg     579

GCGCTGACGCGGCTGGTGACGGACCGCAGCGGGCTGGAGCAGGCGATATCGCATCCCTTC    1800
AlaLeuThrArgLeuValThrAspArgSerGlyLeuGluGlnAlaIleSerHisProPhe     599

GCGGCTGTCGCGCCGGGCGTCTCACCGCAAGGCCAGGTCTGGTGGGCCGTGCCGACCCTG    1860
AlaAlaValAlaProGlyValSerProGlnGlyGlnValTrpTrpAlaValProThrLeu     619

CTGCGCGACGACGATGCCGGAATGCTGAAGGGCTGGAGCTGGGACCAGGCCTTGTCTGAG    1920
LeuArgAspAspAspAlaGlyMetLeuLysGlyTrpSerTrpAspGlnAlaLeuSerGlu     639

GCCCTCTCGGTCGCGTCGCAGAACCTGACCGGGCGAAGCTGGGGCGAAGAGCATCGGCCG    1980
AlaLeuSerValAlaSerGlnAsnLeuThrGlyArgSerTrpGlyGluGluHisArgPro     659

CGCTTCACGCATCCGCTTGCCACGCAATTCCCGGCCTGGGCGGGGCTGCTGAATCCGGCT    2040
ArgPheThrHisProLeuAlaThrGlnPheProAlaTrpAlaGlyLeuLeuAsnProAla     679

TCCCGTCCGATCGGCGGCGATGGCGACACCGTGCTGGCGAACGGGCTCGTCCCGTCAGCC    2100
SerArgProIleGlyGlyAspGlyAspThrValLeuAlaAsnGlyLeuValProSerAla     699

GGGCCGCAGGCGACCTATGGCGCCCTGTCGCGCTACGTCTTTGATGTCGGCAATTGGGAC    2160
GlyProGlnAlaThrTyrGlyAlaLeuSerArgTyrValPheAspValGlyAsnTrpAsp     719

AATAGCCGCTGGGTCGTCTTCCACGGCGCCTCCGGGCATCCGGCCAGCGCCCATTATGCC    2220
AsnSerArgTrpValValPheHisGlyAlaSerGlyHisProAlaSerAlaHisTyrAla     739

GATCAGAATGCGCCCTGGAGCGACTGTGCGATGGTGCCGATGCTCTATAGCTGGGACAGG    2280
AspGlnAsnAlaProTrpSerAspCysAlaMetValProMetLeuTyrSerTrpAspArg     759

ATCGCGGCAGAGGCCGTGACGTCGCAGGAACTCGTCCCGGCCTGA-3'               2325
IleAlaAlaGluAlaValThrSerGlnGluLeuValProAla***                   773
```

FIG.3H

```
GGATCC GGTACC AAG GAC GTC
BamHI  KpnI       AatII
```
↑ conversion by using synthetic DNA

```
BamHI SmaI/MuI                              AatII
          **        *       *       *  *    *     **
GGATCCCCCGCGTGAGCTTGCCCAGATTCCGACAAGCA ATG ACGTCC-GACAAGGA
       10        20        30        40        50        60
  *         *         *        *  *
 ATG ACTATGGCTGCCAACACCGATCGCGCGGTCTTGCAGGCGGCGCTGCCGCCGCTTTCC
 Met ThrMetAlaAlaAsnThrAspArgAlaValLeuGlnAlaAlaLeuProProLeuSer
        70        80        90       100       110
         *         *         *         *         *
GGCAGCCTCCCCATTCCCGGATTGAGCGCGTCGGTCCGTATCCAGCGCGATGCC----
GlySerLeuProIleProGlyLeuSerAlaSerValArgIleGlnArgAspAla----
```

FIG.3J

```
                                                              5'-GGATCCAATC
        10         20         30         40         50         60
ATGTCCAACACAATCGTCGTCGTTGGTGCCGGTGTCATTGGCTTGACGTCGGCCTTGTTG
MetSerAsnThrIleValValValGlyAlaGlyValIleGlyLeuThrSerAlaLeuLeu 70         80         90        100        110        120
CTCTCCAAGAACAAGGGCAACAAGATCACCGTCGTGGCCAAGCACATGCCCGGCGACTAT
LeuSerLysAsnLysGlyAsnLysIleThrValValAlaLysHisMetProGlyAspTyr 130        140        150        160        170        180
GACGTTGAATACGCCTCGCCTTTTGCTGGTGCCAACCACTCCCCCATGGCGACGGAAGAG
AspValGluTyrAlaSerProPheAlaGlyAlaAsnHisSerProMetAlaThrGluGlu 190        200        210        220        230        240
AGCAGCGAATGGGAACGTCGCACTTGGTACGAGTTTAAGAGACTGGTCGAGGAGGTCCCT
SerSerGluTrpGluArgArgThrTrpTyrGluPheLysArgLeuValGluGluValPro 250        260        270        280        290        300
GAGGCCGGTGTTCATTTCCAGAAGTCTCGCATCCAGAGGCGCAATGTGGACACTGAAAAG
GluAlaGlyValHisPheGlnLysSerArgIleGlnArgArgAsnValAspThrGluLys 310        320        330        340        350        360
GCGCAGAGGTCTGGTTTCCCAGACGCCCTCTTCTCGAAAGAACCCTGGTTCAAGAACATG
AlaGlnArgSerGlyPheProAspAlaLeuPheSerLysGluProTrpPheLysAsnMet 370        380        390        400        410        420
TTTGAGGACTTCCGTGAGCAGCACCCTAGCGAGGTCATCCCCGGTTACGACTCTGGCTGC
PheGluAspPheArgGluGlnHisProSerGluValIleProGlyTyrAspSerGlyCys 430        440        450        460        470        480
GAGTTCACATCGGTGTGCATCAACACGGCCATCTACCTCCCCTGGCTCCTCGGCCAGTGC
GluPheThrSerValCysIleAsnThrAlaIleTyrLeuProTrpLeuLeuGlyGlnCys 490        500        510        520        530        540
ATCAAGAATGGCGTCATCGTCAAGCGCGCCATCCTCAACGACATTAGCGAGGCCAAGAAG
IleLysAsnGlyValIleValLysArgAlaIleLeuAsnAspIleSerGluAlaLysLys 550        560        570        580        590        600
CTGAGCCACGCGGGCAAGACGCCCAATATCATCGTCAACGCCACGGGTCTCGGCTCCTAC
LeuSerHisAlaGlyLysThrProAsnIleIleValAsnAlaThrGlyLeuGlySerTyr 610        620        630        640        650        660
AAGCTGGGCGGTGTCGAGGACAAGACCATGGCGCCTGCGCGGGGACAGATTGTGGTTGTG
LysLeuGlyGlyValGluAspLysThrMetAlaProAlaArgGlyGlnIleValValVal 670        680        690        700        710        720
CGCAACGAGAGCAGCCCCATGCTCCTCACTTCAGGTGTCGAGGACGGCGGTGCTGATGTC
ArgAsnGluSerSerProMetLeuLeuThrSerGlyValGluAspGlyGlyAlaAspVal
```

FIG.3L

```
       730       740       750       760       770       780
ATGTACTTGATGCAGCGAGCAGCTGGCGGTGGCACCATCCTGGGCGGTACCTACGACGTT
MetTyrLeuMetGlnArgAlaAlaGlyGlyGlyThrIleLeuGlyGlyThrTyrAspVal 790       800       810       820       830       840
GGCAACTGGGAGTCTCAGCCAGACCCCAACATCGCGAATCGCATCATGCAGCGCATCGTC
GlyAsnTrpGluSerGlnProAspProAsnIleAlaAsnArgIleMetGlnArgIleVal 850       860       870       880       890       900
GAGGTGCGGCCCGAGATTGCCAACGGCAAGGGCGTCAAGGGGCTGAGCGTGATCCGACAC
GluValArgProGluIleAlaAsnGlyLysGlyValLysGlyLeuSerValIleArgHis 910       920       930       940       950       960
GCCGTCGGCATGCGGCCGTGGCGAAAGGACGGAGTCAGGATCGAGGAGGAGAAGCTGGAT
AlaValGlyMetArgProTrpArgLysAspGlyValArgIleGluGluGluLysLeuAsp 970       980       990      1000      1010      1020
GATGAGACTTGGATCGTGCACAACTACGGACACTCTGGATGGGGTTACCAGGGTTCGTAT
AspGluThrTrpIleValHisAsnTyrGlyHisSerGlyTrpGlyTyrGlnGlySerTyr 1030      1040      1050      1060      1070      1080
GGTTGTGCTGAGAATGTAGTCCAGTTGGTTGACAAGGTCGGCAAGGCGGCCAAGTCTAAG
GlyCysAlaGluAsnValValGlnLeuValAspLysValGlyLysAlaAlaLysSerLys

CTGTAGTTGAAAAGGCCTGAATGAGTAATAGTAATTGGATATTGGAAATACCGTATTTGC
Leu***

CCTCGAAAAAAAAAAAAAAAAAAAAAAAAAAAAAAAAAAAAAGTACCTTCTGAGGCGGAAAGAAC

CAGCCGGATCAATTCGAGCTCGCCCGGGGATCC-3'
```

FIG.3M

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 3172 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

```
CTCGAGTCGT ASATACATAC AGAAATAGAA TACGACACGT TATACGAGTA CATGACTACA      60
TGTGTTGACG AACGCTGAGA CTGTCCGCCA AAGCCCATCT GAGGAAATTA CACGTATCGA     120
GGTTTATTGC ACCTGTTTCA AAGATATAGT ACCTACGTAT CTATATACTC ATGCATATAT     180
ATTATTAGTG ATAGCCGAAA CACGGGCGAA GATAGTACCC GATTCGACCA TGTCGTCCGC     240
CCCTTTACCT CTTGACGTCC CACGATCCGG CTCGCTCCAG ATTGCTACAT TACAGCAACC     300
CCCTGGAACA TGTGTGGACA CAACCCACCC AACTGGCCCG GGTCTGAGGC GTCATGATGG     360
AAGAGGGTTG GTTACACCGA TACCAGGTGC CAAGGCCGTG CCTCCATGC  GCACCGGCTT     420
GTGTCCCCCA GTCGCCGGTT CCCCGGCAAT GGATGGTTGT CGCCCGTCCA CCTCCTCCCC     480
CTCCTCCTCC TCCTCCTCCT CCTCCTCTTC CTCATTCTAC CCTGCCCTGC CCCCTTTCTC     540
```

-continued

```
TGTTGAACTT GCCGCTGGAC TTATCCTCCT TCCACATTTC GACTCGTCAT GTATCCTCGG    600
CGTGCCTGGT TACCCGGTTG CTTCGCATGG GACTATTGAT TCGGAGCCGT GATGCGTCAG    660
TCGACGAGAC CGTGGCCCTG GGAGGGTGGC GTGGACAGCA GAGCACGCCC TCCTGTCTCG    720
ACTCGTGGGG TTGGATAGCG GCGAGCACCG GGGGAGTATA GTCCCTCGG CCGGATGGTT    780
ATCAAAGTCT CGCAGTATCA CGAGGGGCCG GTTCCAGATG ACTATATAAG AGGTCCATGG    840
TATCCTCCCC TCTCCGTCGA CAGAAGAAGA CTCCTCACCC TCACAGCCTG CCTCCTTCAC    900
CGGGTATCAA CCAGCTCTTT TCCCCTCAAC TGCTCACCAA CACCGCCAAC ATGGTCACCC    960
TCCGCCGCCT CGCCGTCCTC CTCGGCGCCA TCCCGCCGC CCTCGCCGCT CCACCACGC    1020
AGAAGCGCGA GGTCGTCCCC AACAAGTACA TCGTGACCCT GAAGGAGGGC GCCTCCAACT   1080
TTGACTCCCA CATCTCCTGG GTCAGCGACA TCCACAAGCG CAGCCTCAGC CGCCGCAGCA   1140
CCGCCGGTAT CGAGAAGGAG TTCCACATCG ACACCTTTAA CGCCTATGTC GGCGAGTTCG   1200
ACGAGACTAC CATTGAGGAG ATCAAGAACA ACCGGATGT GAGTAGTTTT GTCCCTTTCC    1260
CCCCCCCTTT GTCAACGACA CCCACCACCT TGCAATCAAG CCCGCTGACC AGCTCGTCAC   1320
TACAAGGTCC TCGAGGTAGA GGAGGACCAG ATCTGGCACC TCTTCGACGA GCAGGACGAG   1380
GGAGAATTCA GCACCGCCGC CCTCGTCACC CAGAACGGCG CCTGGGGCCT GGGCACCATC   1440
TCTCATCGCC AGCCTGGCTC GACCAGCTAC ATCTACGACG ACTCGGCCGG CAGCGGCACC   1500
TACGCCTACG TCGTGGACAC GGGCATCCTC GAGAGTCACA ACGAGTTCTC CGGCCGCGCC   1560
ATCACGGGCT ACAACGCCGT CGGCGGGAGC AACGCCGACA CCAACGGCCA CGGCACCCAC   1620
GTCGCTGGCA CCATTGGCGG CAGGACCTAC GGCGTTGCCA AGAACACCAA CCTCATCGCT   1680
GTCAAGGTCT TCCGGGGATC TTCGAGCTCT ACTTCCATCA TCCTTGACGG CTTCAACTGG   1740
GCCGTGAACG ATATCATCAA CAGGGGCCGC CAGAACAAGG CTGCCATCAG CATGTCCCTG   1800
GGTGAGCTAT ACCCCTTTTT TTCCCCTGAC ACCAAAGACA CTCAAATTCC CTTTGCTAAC   1860
CACAACTAAA CTCCCCCCTT GCAGGTGGTG GCTACTCTTC TGCCTTCAAC AACGCCGTCA   1920
ACACTGCCTA CTCCCGCGGC GTCCTCTCCG TCGTGGCCGC CGGCAACGAT AACCAGAACG   1980
CCGCCAACTA CTCCCCCGCC TCGGCCGCCA ACGCCATCAC CGTCGGCTCC ATCGCCTCCA   2040
ACTGGGCCCG CTCCAGCTTC AGCAACTACG GCTCCGTGCT CGACATCTTC GCCCCGGAA    2100
CCAGCATCCT CTCCGCCTGG ATCGGCGGCA ACTCGGCCAC CAACACCATC TCCGGCACCT   2160
CCATGGCCAC CCCCCATGTC ACCGGCGTCG TCCTCTACCT CCAGGCCCTC GAGGGTCTGA   2220
CCACCTCTGG CGCTGCCGCC CGCCTCAACG CTCTGGCCAC CACCGGCCGT GTCTCCAACC   2280
CTGGCTCCGG TAGCCCCAAC CGCATCCTCT ACAACGGCAA CGGTGCCTAG TGCGCACGGG   2340
CATGGGATAG CCAGTGATGG ATGGTGAAAC GCCATACGGT GAGCGGCTTT CTTGGCCGAT   2400
AGGGTGGGCG ATCGGGATGG CTTGAGGGTA GCATATATGT ATCTCGGTGA TATTGGGGGG   2460
GGGGCTAGGA CGCTCCAGAG GACCAGGTTT CTGCTCTTGG TGCTATACCT ACATACGATA   2520
TACGAATTGA CCGACTTCCA TGATACACAG AGAGTCTTTG TTCCGTTCCA CATGTACCTA   2580
CGTCCCTACC TCATGGTGTT GCCACGCTGC TCCCAGATAC CAGACGACAT GGTAATAGTA   2640
GACAAAGTAG ACAACATTGA AGCCGGCACA CACGGGGGTC AAGTATCCCC ATGAGCCATG   2700
ATGCTTCAAA CAACTAGAAG AATTAGAAGA TATATATGTG TGTACATAGC TATATGTGTT   2760
ATGCATGTTC CCTCATACCT TCGTTCCCCC CTCCCTCAC CTCTTCCTCC GACCGATCAG    2820
CGGCCCGAGT CGCTGTCACT ATTCCTATGT CAAGCTCGGT CATGCTCTCC GACTCGCCAT   2880
CCTTCTTTAT CCTCCTCGAC ATCTTCGACT GTGTTCCCAT AGGCGAGTCC TGCCCACCTC   2940
```

```
CCATACCCCC  ATTCCCGCCA  AGATGTATAT  CATCGAGGCT  GTAGTTGTGG  TTACGATGAT      3000
GCCCACTGCC  GCCGTTCATC  ATGTCGGCTA  GATCACTCTC  ATTATCCTTG  GCCGCCATAC      3060
CGCCGACCAG  ATCAGCAACC  GGTCCGCCGC  CCGTGACCAG  CGTCGTGCCA  CAGGTTCTTG      3120
CACGCCGTCA  CGATGTCGTG  GCGTAGATGA  GGCAGTTCCA  GAAGCCCTGC  AG              3172
```

( 2 ) INFORMATION FOR SEQ ID NO:2:

( i ) SEQUENCE CHARACTERISTICS:
        ( A ) LENGTH: 1513 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:2:

```
AGAAGAAGAC  TCCTCACCCT  CACAGCCTGC  CTCCTTCACC  GGGTATCAAC  CAGCTCTTTT        60
CCCCTCAACT  GCTCACCAAC  ACCGCCAACA  TGGTCACCCT  CCGCCGCCTC  GCCGTCCTCC       120
TCGGCGCCAT  CCCCGCCGCC  CTCGCCGCTC  CCACCACGCA  GAAGCGCGAG  GTCGTCCCCA       180
ACAAGTACAT  CGTGACCCTG  AAGGAGGGCG  CCTCCAACTT  TGACTCCCAC  ATCTCCTGGG       240
TCAGCGACAT  CCACAAGCGC  AGCCTCAGCC  GCCGCAGCAC  CGCCGGTATC  GAGAAGGAGT       300
TCCACATCGA  CACCTTTAAC  GCCTATGTCG  GCGAGTTCGA  CGAGACTACC  ATTGAGGAGA       360
TCAAGAACAA  CCCGGATGTC  CTCGAGGTAG  AGGAGGACCA  GATCTGGCAC  CTCTTCGACG       420
AGCAGGACGA  GGGAGAATTC  AGCACCGCCG  CCCTCGTCAC  CCAGAACGGC  GCCTGGGGCC       480
TGGGCACCAT  CTCTCATCGC  CAGCCTGGCT  CGACCAGCTA  CATCTACGAC  GACTCGGCCG       540
GCAGCGGCAC  CTACGCCTAC  GTCGTGGACA  CGGGCATCCT  CGAGAGTCAC  AACGAGTTCT       600
CCGGCCGCGC  CATCACGGGC  TACAACGCCG  TCGGCGGGAG  CAACGCCGAC  ACCAACGGCC       660
ACGGCACCCA  CGTCGCTGGC  ACCATTGGCG  GCAGGACCTA  CGGCGTTGCC  AAGAACACCA       720
ACCTCATCGC  TGTCAAGGTC  TTCCGGGGAT  CTTCGAGCTC  TACTTCCATC  ATCCTTGACG       780
GCTTCAACTG  GCCGTGAAC   GATATCATCA  ACAGGGGCCG  CCAGAACAAG  CTGCCATCA        840
GCATGTCCCT  GGGTGGTGGC  TACTCTTCTG  CCTTCAACAA  CGCCGTCAAC  ACTGCCTACT       900
CCCGCGGCGT  CCTCTCCGTC  GTGGCCGCCG  GCAACGATAA  CCAGAACGCC  GCCAACTACT       960
CCCCCGCCTC  GGCCGCCAAC  GCCATCACCG  TCGGCTCCAT  CGCCTCCAAC  TGGGCCCGCT      1020
CCAGCTTCAG  CAACTACGGC  TCCGTGCTCG  ACATCTTCGC  CCCCGGAACC  AGCATCCTCT      1080
CCGCCTGGAT  CGGCGGCAAC  TCGGCCACCA  ACACCATCTC  CGGCACCTCC  ATGGCCACCC      1140
CCCATGTCAC  CGGCGTCGTC  CTCTACCTCC  AGGCCCTCGA  GGGTCTGACC  ACCTCTGGCG      1200
CTGCCGCCCG  CCTCAACGCT  CTGGCCACCA  CCGGCCGTGT  CTCCAACCCT  GGCTCCGGTA      1260
GCCCCAACCG  CATCCTCTAC  AACGGCAACG  GTGCCTAGTG  CGCACGGGCA  TGGGATAGCC      1320
AGTGATGGAT  GGTGAAACGC  CATACGGTGA  GCGGCTTTCT  TGGCCGATAG  GGTGGGCGAT      1380
CGGGATGGCT  TGAGGGTAGC  ATATATGTAT  CTCGGTGATA  TTGGGGGGGG  GGCTAGGACG      1440
CTCCAGAGGA  CCAGGTTTCT  GCTCTTGGTG  CTATACCTAC  ATACGATATA  CGAATTGACC      1500
GACTTCCATG  ATA                                                            1513
```

( 2 ) INFORMATION FOR SEQ ID NO:3:

( i ) SEQUENCE CHARACTERISTICS:
        ( A ) LENGTH: 1546 base pairs
        ( B ) TYPE: nucleic acid (C) STRANDEDNESS: unknown
(D) TOPOLOGY: unknown (ii) MOLECULE TYPE: DNA (genomic)

(ix) FEATURE:
(A) NAME/KEY: CDS
(B) LOCATION: 1..1323

(xi) SEQUENCE DESCRIPTION: SEQ ID NO:3:

| | | | | | | | | | | | | | | | | |
|---|---|---|---|---|---|---|---|---|---|---|---|---|---|---|---|---|
| GAA | TTC | CGG | GGG | GGG | GGG | GGG | GGG | GGG | GAG | AAG | AAG | ACT | CCT | CAC | CCT | 48 |
| Glu | Phe | Arg | Gly | Gly | Gly | Gly | Gly | Gly | Glu | Lys | Lys | Thr | Pro | His | Pro | |
| 1 | | | | 5 | | | | | 10 | | | | | 15 | | |
| CAC | AGC | CTG | CCT | CCT | TCA | CCG | GGT | ATC | AAC | CAG | CTC | TTT | TCC | CCT | CAA | 96 |
| His | Ser | Leu | Pro | Pro | Ser | Pro | Gly | Ile | Asn | Gln | Leu | Phe | Ser | Pro | Gln | |
| | | | 20 | | | | | 25 | | | | | 30 | | | |
| CTG | CTC | ACC | AAC | ACC | GCC | AAC | ATG | GTC | ACC | CTC | CGC | CGC | CTC | GCC | GTC | 144 |
| Leu | Leu | Thr | Asn | Thr | Ala | Asn | Met | Val | Thr | Leu | Arg | Arg | Leu | Ala | Val | |
| | | 35 | | | | | 40 | | | | | 45 | | | | |
| CTC | CTC | GGC | GCC | ATC | CCC | GCC | GCC | CTC | GCC | GCT | CCC | ACC | ACG | CAG | AAG | 192 |
| Leu | Leu | Gly | Ala | Ile | Pro | Ala | Ala | Leu | Ala | Ala | Pro | Thr | Thr | Gln | Lys | |
| | 50 | | | | | 55 | | | | | 60 | | | | | |
| CGC | GAG | GTC | GTC | CCC | AAC | AAG | TAC | ATC | GTG | ACC | CTG | AAG | GAG | GGC | GCC | 240 |
| Arg | Glu | Val | Val | Pro | Asn | Lys | Tyr | Ile | Val | Thr | Leu | Lys | Glu | Gly | Ala | |
| 65 | | | | | 70 | | | | | 75 | | | | | 80 | |
| TCC | AAC | TTT | GAC | TCC | CAC | ATC | TCC | TGG | GTC | AGC | GAC | ATC | CAC | AAG | CGC | 288 |
| Ser | Asn | Phe | Asp | Ser | His | Ile | Ser | Trp | Val | Ser | Asp | Ile | His | Lys | Arg | |
| | | | | 85 | | | | | 90 | | | | | 95 | | |
| AGC | CTC | AGC | CGC | CGC | AGC | ACC | GCC | GGT | ATC | GAG | AAG | GAG | TTC | CAC | ATC | 336 |
| Ser | Leu | Ser | Arg | Arg | Ser | Thr | Ala | Gly | Ile | Glu | Lys | Glu | Phe | His | Ile | |
| | | | 100 | | | | | 105 | | | | | 110 | | | |
| GAC | ACC | TTT | AAC | GCC | TAT | GTC | GGC | GAG | TTC | GAC | GAG | ACT | ACC | ATT | GAG | 384 |
| Asp | Thr | Phe | Asn | Ala | Tyr | Val | Gly | Glu | Phe | Asp | Glu | Thr | Thr | Ile | Glu | |
| | | 115 | | | | | 120 | | | | | 125 | | | | |
| GAG | ATC | AAG | AAC | AAC | CCG | GAT | GTC | CTC | GAG | GTA | GAG | GAG | GAC | CAG | ATC | 432 |
| Glu | Ile | Lys | Asn | Asn | Pro | Asp | Val | Leu | Glu | Val | Glu | Glu | Asp | Gln | Ile | |
| | 130 | | | | | 135 | | | | | 140 | | | | | |
| TGG | CAC | CTC | TTC | GAC | GAG | CAG | GAC | GAG | GGA | GAA | TTC | AGC | ACC | GCC | GCC | 480 |
| Trp | His | Leu | Phe | Asp | Glu | Gln | Asp | Glu | Gly | Glu | Phe | Ser | Thr | Ala | Ala | |
| 145 | | | | | 150 | | | | | 155 | | | | | 160 | |
| CTC | GTC | ACC | CAG | AAC | GGC | GCC | TGG | GGC | CTG | GGC | ACC | ATC | TCT | CAT | CGC | 528 |
| Leu | Val | Thr | Gln | Asn | Gly | Ala | Trp | Gly | Leu | Gly | Thr | Ile | Ser | His | Arg | |
| | | | | 165 | | | | | 170 | | | | | 175 | | |
| CAG | CCT | GGC | TCG | ACC | AGC | TAC | ATC | TAC | GAC | GAC | TCG | GCC | GGC | AGC | GGC | 576 |
| Gln | Pro | Gly | Ser | Thr | Ser | Tyr | Ile | Tyr | Asp | Asp | Ser | Ala | Gly | Ser | Gly | |
| | | | 180 | | | | | 185 | | | | | 190 | | | |
| ACC | TAC | GCC | TAC | GTC | GTG | GAC | ACG | GGC | ATC | CTC | GAG | AGT | CAC | AAC | GAG | 624 |
| Thr | Tyr | Ala | Tyr | Val | Val | Asp | Thr | Gly | Ile | Leu | Glu | Ser | His | Asn | Glu | |
| | | 195 | | | | | 200 | | | | | 205 | | | | |
| TTC | TCC | GGC | CGC | GCC | ATC | ACG | GGC | TAC | AAC | GCC | GTC | GGC | GGG | AGC | AAC | 672 |
| Phe | Ser | Gly | Arg | Ala | Ile | Thr | Gly | Tyr | Asn | Ala | Val | Gly | Gly | Ser | Asn | |
| | 210 | | | | | 215 | | | | | 220 | | | | | |
| GCC | GAC | ACC | AAC | GGC | CAC | GGC | ACC | CAC | GTC | GCT | GGC | ACC | ATT | GGC | GGC | 720 |
| Ala | Asp | Thr | Asn | Gly | His | Gly | Thr | His | Val | Ala | Gly | Thr | Ile | Gly | Gly | |
| 225 | | | | | 230 | | | | | 235 | | | | | 240 | |
| AGG | ACC | TAC | GGC | GTT | GCC | AAG | AAC | ACC | AAC | CTC | ATC | GCT | GTC | AAG | GTC | 768 |
| Arg | Thr | Tyr | Gly | Val | Ala | Lys | Asn | Thr | Asn | Leu | Ile | Ala | Val | Lys | Val | |
| | | | | 245 | | | | | 250 | | | | | 255 | | |
| TTC | CGG | GGA | TCT | TCG | AGC | TCT | ACT | TCC | ATC | ATC | CTT | GAC | GGC | TTC | AAC | 816 |
| Phe | Arg | Gly | Ser | Ser | Ser | Ser | Thr | Ser | Ile | Ile | Leu | Asp | Gly | Phe | Asn | |
| | | | 260 | | | | | 265 | | | | | 270 | | | |
| TGG | GCC | GTG | AAC | GAT | ATC | ATC | AAC | AGG | GGC | CGC | CAG | AAC | AAG | GCT | GCC | 864 |

```
Trp Ala Val Asn Asp Ile Ile Asn Arg Gly Arg Gln Asn Lys Ala Ala
    275                 280                 285

ATC AGC ATG TCC CTG GGT GGT GGC TAC TCT TCT GCC TTC AAC AAC GCC      912
Ile Ser Met Ser Leu Gly Gly Gly Tyr Ser Ser Ala Phe Asn Asn Ala
    290                 295                 300

GTC AAC ACT GCC TAC TCC CGC GGC GTC CTC TCC GTC GTG GCC GCC GGC      960
Val Asn Thr Ala Tyr Ser Arg Gly Val Leu Ser Val Val Ala Ala Gly
305                 310                 315                 320

AAC GAT AAC CAG AAC GCC GCC AAC TAC TCC CCC GCC TCG GCC GCC AAC     1008
Asn Asp Asn Gln Asn Ala Ala Asn Tyr Ser Pro Ala Ser Ala Ala Asn
                325                 330                 335

GCC ATC ACC GTC GGC TCC ATC GCC TCC AAC TGG GCC CGC TCC AGC TTC     1056
Ala Ile Thr Val Gly Ser Ile Ala Ser Asn Trp Ala Arg Ser Ser Phe
        340                 345                 350

AGC AAC TAC GGC TCC GTG CTC GAC ATC TTC GCC CCC GGA ACC AGC ATC     1104
Ser Asn Tyr Gly Ser Val Leu Asp Ile Phe Ala Pro Gly Thr Ser Ile
    355                 360                 365

CTC TCC GCC TGG ATC GGC GGC AAC TCG GCC ACC AAC ACC ATC TCC GGC     1152
Leu Ser Ala Trp Ile Gly Gly Asn Ser Ala Thr Asn Thr Ile Ser Gly
    370                 375                 380

ACC TCC ATG GCC ACC CCC CAT GTC ACC GGC GTC GTC CTC TAC CTC CAG     1200
Thr Ser Met Ala Thr Pro His Val Thr Gly Val Val Leu Tyr Leu Gln
385                 390                 395                 400

GCC CTC GAG GGT CTG ACC ACC TCT GGC GCT GCC GCC CGC CTC AAC GCT     1248
Ala Leu Glu Gly Leu Thr Thr Ser Gly Ala Ala Ala Arg Leu Asn Ala
                405                 410                 415

CTG GCC ACC ACC GGC CGT GTC TCC AAC CCT GGC TCC GGT AGC CCC AAC     1296
Leu Ala Thr Thr Gly Arg Val Ser Asn Pro Gly Ser Gly Ser Pro Asn
        420                 425                 430

CGC ATC CTC TAC AAC GGC AAC GGT GCC TAGTGCGCAC GGGCATGGGA           1343
Arg Ile Leu Tyr Asn Gly Asn Gly Ala
    435                 440

TAGCCAGTGA TGGATGGTGA AACGCCATAC GGTGAGCGGC TTTCTTGGCC GATAGGGTGG   1403

GCGATCGGGA TGGCTTGAGG GTAGCATATA TGTATCTCGG TGATATTGGG GGGGGGGCTA   1463

GGACGCTCCA GAGGACCAGG TTTCTGCTCT TGGTGCTATA CCTACATACG ATATACGAAT   1523

TGACCGACTT CCATGATAAA AAA                                          1546
```

( 2 ) INFORMATION FOR SEQ ID NO:4:

( i ) SEQUENCE CHARACTERISTICS:
        ( A ) LENGTH: 441 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu Phe Arg Gly Gly Gly Gly Gly Gly Glu Lys Lys Thr Pro His Pro
  1               5                  10                  15

His Ser Leu Pro Pro Ser Pro Gly Ile Asn Gln Leu Phe Ser Pro Gln
                20                  25                  30

Leu Leu Thr Asn Thr Ala Asn Met Val Thr Leu Arg Arg Leu Ala Val
            35                  40                  45

Leu Leu Gly Ala Ile Pro Ala Ala Leu Ala Ala Pro Thr Thr Gln Lys
        50                  55                  60

Arg Glu Val Val Pro Asn Lys Tyr Ile Val Thr Leu Lys Glu Gly Ala
 65                  70                  75                  80

Ser Asn Phe Asp Ser His Ile Ser Trp Val Ser Asp Ile His Lys Arg
                85                  90                  95
```

Ser Leu Ser Arg Arg Ser Thr Ala Gly Ile Glu Lys Glu Phe His Ile
            100                 105                 110

Asp Thr Phe Asn Ala Tyr Val Gly Glu Phe Asp Glu Thr Thr Ile Glu
            115                 120                 125

Glu Ile Lys Asn Asn Pro Asp Val Leu Val Glu Glu Asp Gln Ile
            130                 135                 140

Trp His Leu Phe Asp Glu Gln Asp Glu Gly Glu Phe Ser Thr Ala Ala
145                 150                 155                 160

Leu Val Thr Gln Asn Gly Ala Trp Gly Leu Gly Thr Ile Ser His Arg
                165                 170                 175

Gln Pro Gly Ser Thr Ser Tyr Ile Tyr Asp Asp Ser Ala Gly Ser Gly
            180                 185                 190

Thr Tyr Ala Tyr Val Val Asp Thr Gly Ile Leu Glu Ser His Asn Glu
            195                 200                 205

Phe Ser Gly Arg Ala Ile Thr Gly Tyr Asn Ala Val Gly Gly Ser Asn
            210                 215                 220

Ala Asp Thr Asn Gly His Gly Thr His Val Ala Gly Thr Ile Gly Gly
225                 230                 235                 240

Arg Thr Tyr Gly Val Ala Lys Asn Thr Asn Leu Ile Ala Val Lys Val
                245                 250                 255

Phe Arg Gly Ser Ser Ser Ser Thr Ser Ile Ile Leu Asp Gly Phe Asn
            260                 265                 270

Trp Ala Val Asn Asp Ile Ile Asn Arg Gly Arg Gln Asn Lys Ala Ala
            275                 280                 285

Ile Ser Met Ser Leu Gly Gly Gly Tyr Ser Ser Ala Phe Asn Asn Ala
290                 295                 300

Val Asn Thr Ala Tyr Ser Arg Gly Val Leu Ser Val Val Ala Ala Gly
305                 310                 315                 320

Asn Asp Asn Gln Asn Ala Ala Asn Tyr Ser Pro Ala Ser Ala Ala Asn
                325                 330                 335

Ala Ile Thr Val Gly Ser Ile Ala Ser Asn Trp Ala Arg Ser Ser Phe
            340                 345                 350

Ser Asn Tyr Gly Ser Val Leu Asp Ile Phe Ala Pro Gly Thr Ser Ile
            355                 360                 365

Leu Ser Ala Trp Ile Gly Gly Asn Ser Ala Thr Asn Thr Ile Ser Gly
    370                 375                 380

Thr Ser Met Ala Thr Pro His Val Thr Gly Val Val Leu Tyr Leu Gln
385                 390                 395                 400

Ala Leu Glu Gly Leu Thr Thr Ser Gly Ala Ala Ala Arg Leu Asn Ala
                405                 410                 415

Leu Ala Thr Thr Gly Arg Val Ser Asn Pro Gly Ser Gly Ser Pro Asn
            420                 425                 430

Arg Ile Leu Tyr Asn Gly Asn Gly Ala
            435                 440

( 2 ) INFORMATION FOR SEQ ID NO:5:

( i ) SEQUENCE CHARACTERISTICS:
        ( A ) LENGTH: 1209 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS (B) LOCATION: 1..1206

(xi) SEQUENCE DESCRIPTION: SEQ ID NO:5:

| | | | | | | | | | | | | | | | | |
|---|---|---|---|---|---|---|---|---|---|---|---|---|---|---|---|---|
| ATG | GTC | ACC | CTC | CGC | CGC | CTC | GCC | GTC | CTC | CTC | GGC | GCC | ATC | CCC | GCC | 48 |
| Met | Val | Thr | Leu | Arg | Arg | Leu | Ala | Val | Leu | Leu | Gly | Ala | Ile | Pro | Ala | |
| 1 | | | | 5 | | | | | 10 | | | | | 15 | | |
| GCC | CTC | GCC | GCT | CCC | ACC | ACG | CAG | AAG | CGC | GAG | GTC | GTC | CCC | AAC | AAG | 96 |
| Ala | Leu | Ala | Ala | Pro | Thr | Thr | Gln | Lys | Arg | Glu | Val | Val | Pro | Asn | Lys | |
| | | | 20 | | | | | 25 | | | | | 30 | | | |
| TAC | ATC | GTG | ACC | CTG | AAG | GAG | GGC | GCC | TCC | AAC | TTT | GAC | TCC | CAC | ATC | 144 |
| Tyr | Ile | Val | Thr | Leu | Lys | Glu | Gly | Ala | Ser | Asn | Phe | Asp | Ser | His | Ile | |
| | | | 35 | | | | 40 | | | | | 45 | | | | |
| TCC | TGG | GTC | AGC | GAC | ATC | CAC | AAG | CGC | AGC | CTC | AGC | CGC | CGC | AGC | ACC | 192 |
| Ser | Trp | Val | Ser | Asp | Ile | His | Lys | Arg | Ser | Leu | Ser | Arg | Arg | Ser | Thr | |
| | 50 | | | | | 55 | | | | | 60 | | | | | |
| GCC | GGT | ATC | GAG | AAG | GAG | TTC | CAC | ATC | GAC | ACC | TTT | AAC | GCC | TAT | GTC | 240 |
| Ala | Gly | Ile | Glu | Lys | Glu | Phe | His | Ile | Asp | Thr | Phe | Asn | Ala | Tyr | Val | |
| 65 | | | | | 70 | | | | | 75 | | | | | 80 | |
| GGC | GAG | TTC | GAC | GAG | ACT | ACC | ATT | GAG | GAG | ATC | AAG | AAC | AAC | CCG | GAT | 288 |
| Gly | Glu | Phe | Asp | Glu | Thr | Thr | Ile | Glu | Glu | Ile | Lys | Asn | Asn | Pro | Asp | |
| | | | | 85 | | | | | 90 | | | | | 95 | | |
| GTC | CTC | GAG | GTA | GAG | GAG | GAC | CAG | ATC | TGG | CAC | CTC | TTC | GAC | GAG | CAG | 336 |
| Val | Leu | Glu | Val | Glu | Glu | Asp | Gln | Ile | Trp | His | Leu | Phe | Asp | Glu | Gln | |
| | | | 100 | | | | | 105 | | | | | 110 | | | |
| GAC | GAG | GGA | GAA | TTC | AGC | ACC | GCC | GCC | CTC | GTC | ACC | CAG | AAC | GGC | GCC | 384 |
| Asp | Glu | Gly | Glu | Phe | Ser | Thr | Ala | Ala | Leu | Val | Thr | Gln | Asn | Gly | Ala | |
| | | | 115 | | | | | 120 | | | | | 125 | | | |
| TGG | GGC | CTG | GGC | ACC | ATC | TCT | CAT | CGC | CAG | CCT | GGC | TCG | ACC | AGC | TAC | 432 |
| Trp | Gly | Leu | Gly | Thr | Ile | Ser | His | Arg | Gln | Pro | Gly | Ser | Thr | Ser | Tyr | |
| | 130 | | | | | 135 | | | | | 140 | | | | | |
| ATC | TAC | GAC | GAC | TCG | GCC | GGC | AGC | GGC | ACC | TAC | GCC | TAC | GTC | GTG | GAC | 480 |
| Ile | Tyr | Asp | Asp | Ser | Ala | Gly | Ser | Gly | Thr | Tyr | Ala | Tyr | Val | Val | Asp | |
| 145 | | | | | 150 | | | | | 155 | | | | | 160 | |
| ACG | GGC | ATC | CTC | GAG | AGT | CAC | AAC | GAG | TTC | TCC | GGC | CGC | GCC | ATC | ACG | 528 |
| Thr | Gly | Ile | Leu | Glu | Ser | His | Asn | Glu | Phe | Ser | Gly | Arg | Ala | Ile | Thr | |
| | | | | 165 | | | | | 170 | | | | | 175 | | |
| GGC | TAC | AAC | GCC | GTC | GGC | GGG | AGC | AAC | GCC | GAC | ACC | AAC | GGC | CAC | GGC | 576 |
| Gly | Tyr | Asn | Ala | Val | Gly | Gly | Ser | Asn | Ala | Asp | Thr | Asn | Gly | His | Gly | |
| | | | 180 | | | | | 185 | | | | | 190 | | | |
| ACC | CAC | GTC | GCT | GGC | ACC | ATT | GGC | GGC | AGG | ACC | TAC | GGC | GTT | GCC | AAG | 624 |
| Thr | His | Val | Ala | Gly | Thr | Ile | Gly | Gly | Arg | Thr | Tyr | Gly | Val | Ala | Lys | |
| | | | 195 | | | | | 200 | | | | | 205 | | | |
| AAC | ACC | AAC | CTC | ATC | GCT | GTC | AAG | GTC | TTC | CGG | GGA | TCT | TCG | AGC | TCT | 672 |
| Asn | Thr | Asn | Leu | Ile | Ala | Val | Lys | Val | Phe | Arg | Gly | Ser | Ser | Ser | Ser | |
| | | 210 | | | | | 215 | | | | | 220 | | | | |
| ACT | TCC | ATC | ATC | CTT | GAC | GGC | TTC | AAC | TGG | GCC | GTG | AAC | GAT | ATC | ATC | 720 |
| Thr | Ser | Ile | Ile | Leu | Asp | Gly | Phe | Asn | Trp | Ala | Val | Asn | Asp | Ile | Ile | |
| 225 | | | | | 230 | | | | | 235 | | | | | 240 | |
| AAC | AGG | GGC | CGC | CAG | AAC | AAG | GCT | GCC | ATC | AGC | ATG | TCC | CTG | GGT | GGT | 768 |
| Asn | Arg | Gly | Arg | Gln | Asn | Lys | Ala | Ala | Ile | Ser | Met | Ser | Leu | Gly | Gly | |
| | | | | 245 | | | | | 250 | | | | | 255 | | |
| GGC | TAC | TCT | TCT | GCC | TTC | AAC | AAC | GCC | GTC | AAC | ACT | GCC | TAC | TCC | CGC | 816 |
| Gly | Tyr | Ser | Ser | Ala | Phe | Asn | Asn | Ala | Val | Asn | Thr | Ala | Tyr | Ser | Arg | |
| | | | 260 | | | | | 265 | | | | | 270 | | | |
| GGC | GTC | CTC | TCC | GTC | GTG | GCC | GCC | GGC | AAC | GAT | AAC | CAG | AAC | GCC | GCC | 864 |
| Gly | Val | Leu | Ser | Val | Val | Ala | Ala | Gly | Asn | Asp | Asn | Gln | Asn | Ala | Ala | |
| | | | 275 | | | | | 280 | | | | | 285 | | | |
| AAC | TAC | TCC | CCC | GCC | TCG | GCC | GCC | AAC | GCC | ATC | ACC | GTC | GGC | TCC | ATC | 912 |
| Asn | Tyr | Ser | Pro | Ala | Ser | Ala | Ala | Asn | Ala | Ile | Thr | Val | Gly | Ser | Ile | |
| | | 290 | | | | | 295 | | | | | 300 | | | | |

| | | | | | | | | | | | | | | | | |
|---|---|---|---|---|---|---|---|---|---|---|---|---|---|---|---|---|
| GCC | TCC | AAC | TGG | GCC | CGC | TCC | AGC | TTC | AGC | AAC | TAC | GGC | TCC | GTG | CTC | 960 |
| Ala | Ser | Asn | Trp | Ala | Arg | Ser | Ser | Phe | Ser | Asn | Tyr | Gly | Ser | Val | Leu | |
| 305 | | | | 310 | | | | | 315 | | | | | 320 | | |
| GAC | ATC | TTC | GCC | CCC | GGA | ACC | AGC | ATC | CTC | TCC | GCC | TGG | ATC | GGC | GGC | 1008 |
| Asp | Ile | Phe | Ala | Pro | Gly | Thr | Ser | Ile | Leu | Ser | Ala | Trp | Ile | Gly | Gly | |
| | | | | 325 | | | | 330 | | | | | 335 | | | |
| AAC | TCG | GCC | ACC | AAC | ACC | ATC | TCC | GGC | ACC | TCC | ATG | GCC | ACC | CCC | CAT | 1056 |
| Asn | Ser | Ala | Thr | Asn | Thr | Ile | Ser | Gly | Thr | Ser | Met | Ala | Thr | Pro | His | |
| | | | 340 | | | | 345 | | | | | 350 | | | | |
| GTC | ACC | GGC | GTC | GTC | CTC | TAC | CTC | CAG | GCC | CTC | GAG | GGT | CTG | ACC | ACC | 1104 |
| Val | Thr | Gly | Val | Val | Leu | Tyr | Leu | Gln | Ala | Leu | Glu | Gly | Leu | Thr | Thr | |
| | | 355 | | | | 360 | | | | | 365 | | | | | |
| TCT | GGC | GCT | GCC | GCC | CGC | CTC | AAC | GCT | CTG | GCC | ACC | ACC | GGC | CGT | GTC | 1152 |
| Ser | Gly | Ala | Ala | Ala | Arg | Leu | Asn | Ala | Leu | Ala | Thr | Thr | Gly | Arg | Val | |
| | 370 | | | | | 375 | | | | | 380 | | | | | |
| TCC | AAC | CCT | GGC | TCC | GGT | AGC | CCC | AAC | CGC | ATC | CTC | TAC | AAC | GGC | AAC | 1200 |
| Ser | Asn | Pro | Gly | Ser | Gly | Ser | Pro | Asn | Arg | Ile | Leu | Tyr | Asn | Gly | Asn | |
| 385 | | | | 390 | | | | | 395 | | | | | 400 | | |
| GGT | GCC | TAG | | | | | | | | | | | | | | 1209 |
| Gly | Ala | | | | | | | | | | | | | | | |

(2) INFORMATION FOR SEQ ID NO:6:

(i) SEQUENCE CHARACTERISTICS:
        (A) LENGTH: 402 amino acids
        (B) TYPE: amino acid
        (D) TOPOLOGY: linear (ii) MOLECULE TYPE: protein (xi) SEQUENCE DESCRIPTION: SEQ ID NO:6:

| | | | | | | | | | | | | | | |
|---|---|---|---|---|---|---|---|---|---|---|---|---|---|---|
| Met | Val | Thr | Leu | Arg | Arg | Leu | Ala | Val | Leu | Leu | Gly | Ala | Ile | Pro | Ala |
| 1 | | | | 5 | | | | | 10 | | | | | 15 | |
| Ala | Leu | Ala | Ala | Pro | Thr | Thr | Gln | Lys | Arg | Glu | Val | Val | Pro | Asn | Lys |
| | | | 20 | | | | | 25 | | | | | 30 | | |
| Tyr | Ile | Val | Thr | Leu | Lys | Glu | Gly | Ala | Ser | Asn | Phe | Asp | Ser | His | Ile |
| | | | 35 | | | | 40 | | | | | 45 | | | |
| Ser | Trp | Val | Ser | Asp | Ile | His | Lys | Arg | Ser | Leu | Ser | Arg | Arg | Ser | Thr |
| | 50 | | | | | 55 | | | | | 60 | | | | |
| Ala | Gly | Ile | Glu | Lys | Glu | Phe | His | Ile | Asp | Thr | Phe | Asn | Ala | Tyr | Val |
| 65 | | | | | 70 | | | | | 75 | | | | | 80 |
| Gly | Glu | Phe | Asp | Glu | Thr | Thr | Ile | Glu | Glu | Ile | Lys | Asn | Asn | Pro | Asp |
| | | | | 85 | | | | | 90 | | | | | 95 | |
| Val | Leu | Glu | Val | Glu | Glu | Asp | Gln | Ile | Trp | His | Leu | Phe | Asp | Glu | Gln |
| | | | 100 | | | | | 105 | | | | | 110 | | |
| Asp | Glu | Gly | Glu | Phe | Ser | Thr | Ala | Ala | Leu | Val | Thr | Gln | Asn | Gly | Ala |
| | | 115 | | | | | 120 | | | | | 125 | | | |
| Trp | Gly | Leu | Gly | Thr | Ile | Ser | His | Arg | Gln | Pro | Gly | Ser | Thr | Ser | Tyr |
| | 130 | | | | | 135 | | | | | 140 | | | | |
| Ile | Tyr | Asp | Asp | Ser | Ala | Gly | Ser | Gly | Thr | Tyr | Ala | Tyr | Val | Val | Asp |
| 145 | | | | | 150 | | | | | 155 | | | | | 160 |
| Thr | Gly | Ile | Leu | Glu | Ser | His | Asn | Glu | Phe | Ser | Gly | Arg | Ala | Ile | Thr |
| | | | | 165 | | | | | 170 | | | | | 175 | |
| Gly | Tyr | Asn | Ala | Val | Gly | Gly | Ser | Asn | Ala | Asp | Thr | Asn | Gly | His | Gly |
| | | | 180 | | | | | 185 | | | | | 190 | | |
| Thr | His | Val | Ala | Gly | Thr | Ile | Gly | Gly | Arg | Thr | Tyr | Gly | Val | Ala | Lys |
| | | 195 | | | | | 200 | | | | | 205 | | | |
| Asn | Thr | Asn | Leu | Ile | Ala | Val | Lys | Val | Phe | Arg | Gly | Ser | Ser | Ser | Ser |
| | 210 | | | | | 215 | | | | | 220 | | | | |

| | | | | | | | | | | | | | | |
|---|---|---|---|---|---|---|---|---|---|---|---|---|---|---|
| Thr 225 | Ser | Ile | Ile | Leu 230 | Asp | Gly | Phe | Asn | Trp 235 | Ala | Val | Asn | Asp | Ile Ile 240 |
| Asn | Arg | Gly | Arg 245 | Gln | Asn | Lys | Ala | Ala | Ile 250 | Ser | Met | Ser | Leu 255 | Gly Gly |
| Gly | Tyr | Ser | Ser 260 | Ala | Phe | Asn | Asn | Ala 265 | Val | Asn | Thr | Ala 270 | Ser | Arg |
| Gly | Val | Leu 275 | Ser | Val | Val | Ala | Ala 280 | Gly | Asn | Asp | Asn 285 | Gln | Asn | Ala Ala |
| Asn | Tyr 290 | Ser | Pro | Ala | Ser 295 | Ala | Ala | Asn | Ala | Ile 300 | Thr | Val | Gly | Ser Ile |
| Ala 305 | Ser | Asn | Trp | Ala | Arg 310 | Ser | Ser | Phe | Ser | Asn 315 | Tyr | Gly | Ser | Val Leu 320 |
| Asp | Ile | Phe | Ala | Pro 325 | Gly | Thr | Ser | Ile | Leu 330 | Ser | Ala | Trp | Ile 335 | Gly Gly |
| Asn | Ser | Ala | Thr 340 | Asn | Thr | Ile | Ser | Gly 345 | Thr | Ser | Met | Ala | Thr 350 | Pro His |
| Val | Thr | Gly 355 | Val | Val | Leu | Tyr | Leu 360 | Gln | Ala | Leu | Glu | Gly 365 | Leu | Thr Thr |
| Ser | Gly 370 | Ala | Ala | Ala | Arg | Leu 375 | Asn | Ala | Leu | Ala | Thr 380 | Thr | Gly | Arg Val |
| Ser 385 | Asn | Pro | Gly | Ser | Gly 390 | Ser | Pro | Asn | Arg | Ile 395 | Leu | Tyr | Asn | Gly Asn 400 |
| Gly | Ala | | | | | | | | | | | | | |

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:7:

CCCCCGAATT CGGGGG                                           16

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:8:

AGCGGATCCG CT                                                         12

( 2 ) INFORMATION FOR SEQ ID NO:9:

( i ) SEQUENCE CHARACTERISTICS:
        ( A ) LENGTH: 16 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:9:

TGGCCGGATC CGGCCA 16

( 2 ) INFORMATION FOR SEQ ID NO:10:

( i ) SEQUENCE CHARACTERISTICS:
        ( A ) LENGTH: 590 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:10:

```
GAATTCGGGG  GTCTGAGGCG  TCATGATGGA  AGAGGGTTGG  TTACACCGAT  ACCAGGTGCC    60
AAGGCCGTGC  CTCCCATGCG  CACCGGCTTG  TGTCCCCAG   TCGCCGGTTC  CCCGGCAATG   120
GATGGTTGTC  GCCCGTCCAC  CTCCTCCCCC  TCCTCCTCCT  CCTCCTCCTC  CTCCTCTTCC   180
TCATTCTACC  CTGCCCTGCC  CCCTTTCTCT  GTTGAACTTG  CCGCTGGACT  TATCCTCCTT   240
CCACATTTCG  ACTCGTCATG  TATCCTCGGC  GTGCCTGGTT  ACCCGGTTGC  TTCGCATGGG   300
ACTATTGATT  CGGAGCCGTG  ATGCGTCAGT  CGACGAGACC  GTGGCCCTGG  GAGGGTGGCG   360
TGGACAGCAG  AGCACGCCCT  CCTGTCTCGA  CTCGTGGGGT  TGGATAGCGG  CGAGCACCGG   420
GGGAGTATAG  TCCCCTCGGC  CGGATGGTTA  TCAAAGTCTC  GCAGTATCAC  GAGGGGCCGG   480
TTCCAGATGA  CTATATAAGA  GGTCCATGGT  ATCCTCCCCT  CTCCGTCGAC  AGAAGAAGAC   540
TCCTCACCCT  CACAGCCTGC  CTCCTTCACC  GGGTATCAAC  CAGCGGATCC                590
```

( 2 ) INFORMATION FOR SEQ ID NO:11:

( i ) SEQUENCE CHARACTERISTICS:
        ( A ) LENGTH: 936 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:11:

```
GGATCCGGCC  ACCACCGGCC  GTGTCTCCAA  CCCTGGCTCC  GGTAGCCCCA  ACCGCATCCT    60
CTACAACGGC  AACGGTGCCT  AGTGCGCACG  GGCATGGGAT  AGCCAGTGAT  GGATGGTGAA   120
ACGCCATACG  GTGAGCGGCT  TTCTTGGCCG  ATAGGGTGGG  CGATCGGGAT  GGCTTGAGGG   180
TAGCATATAT  GTATCTCGGT  GATATTGGGG  GGGGGGCTAG  GACGCTCCAG  AGGACCAGGT   240
TTCTGCTCTT  GGTGCTATAC  CTACATACGA  TATCGAATT   GACCGACTTC  CATGATACAC   300
AGAGAGTCTT  TGTTCCGTTC  CACATGTACC  TACGTCCCTA  CCTCATGGTG  TTGCCACGCT   360
GCTCCCAGAT  ACCAGACGAC  ATGGTAATAG  TAGACAAAGT  AGACAACATT  GAAGCCGGCA   420
CACACGGGGG  TCAAGTATCC  CCATGAGCCA  TGATGCTTCA  AACAACTAGA  AGAATTAGAA   480
GATATATATG  TGTGTACATA  GCTATATGTG  TTATGCATGT  TCCCTCATAC  CTTCGTTCCC   540
CCCTCCCCTC  ACCTCTTCCT  CCGACCGATC  AGCGGCCCGA  GTCGCTGTCA  CTATTCCTAT   600
GTCAAGCTCG  GTCATGCTCT  CCGACTCGCC  ATCCTTCTTT  ATCCTCCTCG  ACATCTTCGA   660
CTGTGTTCCC  ATAGGCGAGT  CCTGCCCACC  TCCATACCC   CCATTCCCGC  CAAGATGTAT   720
ATCATCGAGG  CTGTAGTTGT  GGTTACGATG  ATGCCCACTG  CCGCCGTTCA  TCATGTCGGC   780
TAGATCACTC  TCATTATCCT  TGGCCGCCAT  ACCGCCGACC  AGATCAGCAA  CCGGTCCGCC   840
GCCCGTGACC  AGCGTCGTGC  CACAGGTTCT  TGCACGCCGT  CACGATGTCG  TGGCGTAGAT   900
```

GAGGCAGTTC CAGAAGCCCT GCAGGCATGC AAGCTT                                                                   936

( 2 ) INFORMATION FOR SEQ ID NO:12:

( i ) SEQUENCE CHARACTERISTICS:
        ( A ) LENGTH: 11 base pairs
        ( B ) TYPE: nucleic acid
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:12:

GGATCCCCGG G                                                                                              11

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:13:

GGATCGATCC CCGGG                                                                                          15

( 2 ) INFORMATION FOR SEQ ID NO:14:

( i ) SEQUENCE CHARACTERISTICS:
        ( A ) LENGTH: 478 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

GTCGACTACC GGTGAGCCGC TCGACGGGGC GTCGAGTTGC CGGGCCCAAT CCCTGAGCTT                                          60

GGATAGACTG TTCCGGGCCT CATGTGGGTG GCGGCGTCTA CATGCACATG CATAACGGCG                                          120

TTCCTCATCG CTTGGCCCCG CATGCAGTCT TCAGGGACCA AACTCCATCG CCGCTGCTGG                                          180

ACCGTATGTA ACCCCCTCG GCAGTGCACC CGCAGGAGCC GGATAATCGA GACCTTGGCA                                           240

GGCCATAAAG GCGCGTCGTG GGGAAGCTCA TATCGTATAG CAACGGGAGA CACGAGGTAG                                          300

GTACTCAAGT ACACATACAC ACACCCAGCC GCCCGTATAA ACAGCTTCAA GAGGGGCGAA                                          360

TACTTGAATA TCCCTTTGGT CGCTCTTCTG ATTTTCGAGG CTTCTCCTTC CGCCATCGTC                                          420

ACTCACGCAT ATCTCGTCTT TCACATCTTA CACCAGGCAG GACAAACCGT CACCATGG                                            478

( 2 ) INFORMATION FOR SEQ ID NO:15:

( i ) SEQUENCE CHARACTERISTICS:
        ( A ) LENGTH: 1018 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:15:

TGATCAACAA GAATGGTCAG ACCTAAATCG GTCGATCAGG TTCGGCTGAT CTGCCGCTGT                                          60

GGGCGGGCGT GCGGAGGAAT GCGGGAGTAA AAGCAGTTCA AGGGGCCGGA AGGGTCGAGT                                          120

GTCTGCCAGG AAGAATCAGT CCTTCTCCGC CCCCTTTTTT TTTTCCCCTT GCCGGCTATG                                          180

| | | | | | |
|---|---|---|---|---|---|
| TTAAACCACC | AGCAATCGAA | CCCTTTTTCT | CCCATCAGTA | TGCTCTGGAG | TGTACCCTCT | 240 |
| ATGTACATGT | AGTGAAACAG | GCTAAATTTG | CTGCCCCGTG | TGCATGTATC | AATGATGCGT | 300 |
| TTCCTGCGTC | CATGTCTGAC | TGTAGTTGTA | CACGTACACC | ACACCATTGT | CTACCCCCCG | 360 |
| CGACGTATGT | ACGTATTGAT | CTATGATGTG | CATATTCAAC | GCTAACTATT | TTTACCTCGG | 420 |
| ACAGATTCCA | GAATGCTACC | GTAAGCCATC | ATGAACCCAT | GAACCACGGT | GGATCTAGCC | 480 |
| CGGTCATCCC | TGCCTCCCTG | CCACAGTGCG | GGTCATCTCC | TGGGGCCGAG | CACACGAGAG | 540 |
| GCCGAATTGG | CGTTCAGTCG | GCCATGAGGC | CGCTTGCGAT | CCCTTGTGGG | ATTGAAGATC | 600 |
| CGTCGTCGAA | ATTCAGCCGC | CGAGATACCC | TATATCGATT | CATAGATACC | AATATCCGCA | 660 |
| CTGGTAGACG | TTCTTGGACA | GTCCATGCAG | GCGAGCTGCC | TCTCTCTCTC | TCTCTTTTTT | 720 |
| TTTTTTTTTC | TTTAGTTGCA | GTTATTGCAG | TCTGACTGTG | ACCCTGGCAC | TTGGCAAGCC | 780 |
| ACCGGTTCGC | GAGTTATTTC | ATTCCGGTGC | TTCTCCCGTC | GATAGCGCAG | GGATGGGAGG | 840 |
| GAGGGGAGTA | GGGTAAGGGG | GGTTGGTGTG | GGGAGTGTCG | AACCAAAAAA | TGACGGGAGC | 900 |
| TCGGATACAG | CTTCCTCGCA | CGCGCTGTGT | ACTCCTACAT | ACATGTATAT | GCTTTCTAAC | 960 |
| AGGGACCGAG | ACTTATTTAG | GTAAGGATCA | AGGATCGATC | CCCGGGGAGC | TCGAATTC | 1018 |

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:16:

| | | | |
|---|---|---|---|
| AATTCGGATC | CACAGGAAAC | AGCTATGAAA | AAG | 33 |

( 2 ) INFORMATION FOR SEQ ID NO:17:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:17:

| | | |
|---|---|---|
| TTTTTCATAG | CTGTTTCCTG | TGGATCCG | 28 |

( 2 ) INFORMATION FOR SEQ ID NO:18:

( i ) SEQUENCE CHARACTERISTICS:
        ( A ) LENGTH: 1066 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 20..1042

( x i ) SEQUENCE DESCRIPTION: SEQ ID NO:18:

| | | | | | | | | | | | | |
|---|---|---|---|---|---|---|---|---|---|---|---|---|
| GGATCCACAG | GAAACAGCT | ATG | AAA | AAG | CCT | GAA | CTC | ACC | GCG | ACG | TCT | GTC | 52 |
| | | Met | Lys | Lys | Pro | Glu | Leu | Thr | Ala | Thr | Ser | Val | |

|   |   |   |   |   |   |   |   |   |   |   |
|---|---|---|---|---|---|---|---|---|---|---|
|   | 1 |   |   |   | 5 |   |   |   | 10 |   |

```
GAG  AAG  TTT  CTG  ATC  GAA  AAG  TTC  GAC  AGC  GTC  TCC  GAC  CTG  ATG  CAG       100
Glu  Lys  Phe  Leu  Ile  Glu  Lys  Phe  Asp  Ser  Val  Ser  Asp  Leu  Met  Gln
               15                  20                  25

CTC  TCG  GAG  GGC  GAA  GAA  TCT  CGT  GCT  TTC  AGC  TTC  GAT  GTA  GGA  GGG       148
Leu  Ser  Glu  Gly  Glu  Glu  Ser  Arg  Ala  Phe  Ser  Phe  Asp  Val  Gly  Gly
          30                  35                  40

CGT  GGA  TAT  GTC  CTG  CGG  GTA  AAT  AGC  TGC  GCC  GAT  GGT  TTC  TAC  AAA       196
Arg  Gly  Tyr  Val  Leu  Arg  Val  Asn  Ser  Cys  Ala  Asp  Gly  Phe  Tyr  Lys
     45                  50                  55

GAT  CGT  TAT  GTT  TAT  CGG  CAC  TTT  GCA  TCG  GCC  GCG  CTC  CCG  ATT  CCG       244
Asp  Arg  Tyr  Val  Tyr  Arg  His  Phe  Ala  Ser  Ala  Ala  Leu  Pro  Ile  Pro
60                  65                  70                  75

GAA  GTG  CTT  GAC  ATT  GGG  GAA  TTC  AGC  GAG  AGC  CTG  ACC  TAT  TGC  ATC       292
Glu  Val  Leu  Asp  Ile  Gly  Glu  Phe  Ser  Glu  Ser  Leu  Thr  Tyr  Cys  Ile
                    80                  85                  90

TCC  CGC  CGT  GCA  CAG  GGT  GTC  ACG  TTG  CAA  GAC  CTG  CCT  GAA  ACC  GAA       340
Ser  Arg  Arg  Ala  Gln  Gly  Val  Thr  Leu  Gln  Asp  Leu  Pro  Glu  Thr  Glu
               95                  100                 105

CTG  CCC  GCT  GTT  CTG  CAG  CCG  GTC  GCG  GAG  GCC  ATG  GAT  GCG  ATC  GCT       388
Leu  Pro  Ala  Val  Leu  Gln  Pro  Val  Ala  Glu  Ala  Met  Asp  Ala  Ile  Ala
          110                 115                 120

GCG  GCC  GAT  CTT  AGC  CAG  ACG  AGC  GGG  TTC  GGC  CCA  TTC  GGA  CCG  CAA       436
Ala  Ala  Asp  Leu  Ser  Gln  Thr  Ser  Gly  Phe  Gly  Pro  Phe  Gly  Pro  Gln
     125                 130                 135

GGA  ATC  GGT  CAA  TAC  ACT  ACA  TGG  CGT  GAT  TTC  ATA  TGC  GCG  ATT  GCT       484
Gly  Ile  Gly  Gln  Tyr  Thr  Thr  Trp  Arg  Asp  Phe  Ile  Cys  Ala  Ile  Ala
140                 145                 150                 155

GAT  CCC  CAT  GTG  TAT  CAC  TGG  CAA  ACT  GTG  ATG  GAC  GAC  ACC  GTC  AGT       532
Asp  Pro  His  Val  Tyr  His  Trp  Gln  Thr  Val  Met  Asp  Asp  Thr  Val  Ser
                    160                 165                 170

GCG  TCC  GTC  GCG  CAG  GCT  CTC  GAT  GAG  CTG  ATG  CTT  TGG  GCC  GAG  GAC       580
Ala  Ser  Val  Ala  Gln  Ala  Leu  Asp  Glu  Leu  Met  Leu  Trp  Ala  Glu  Asp
               175                 180                 185

TGC  CCC  GAA  GTC  CGG  CAC  CTC  GTG  CAC  GCG  GAT  TTC  GGC  TCC  AAC  AAT       628
Cys  Pro  Glu  Val  Arg  His  Leu  Val  His  Ala  Asp  Phe  Gly  Ser  Asn  Asn
          190                 195                 200

GTC  CTG  ACG  GAC  AAT  GGC  CGC  ATA  ACA  GCG  GTC  ATT  GAC  TGG  AGC  GAG       676
Val  Leu  Thr  Asp  Asn  Gly  Arg  Ile  Thr  Ala  Val  Ile  Asp  Trp  Ser  Glu
     205                 210                 215

GCG  ATG  TTC  GGG  GAT  TCC  CAA  TAC  GAG  GTC  GCC  AAC  ATC  TTC  TTC  TGG       724
Ala  Met  Phe  Gly  Asp  Ser  Gln  Tyr  Glu  Val  Ala  Asn  Ile  Phe  Phe  Trp
220                 225                 230                 235

AGG  CCG  TGG  TTG  GCT  TGT  ATG  GAG  CAG  CAG  ACG  CGC  TAC  TTC  GAG  CGG       772
Arg  Pro  Trp  Leu  Ala  Cys  Met  Glu  Gln  Gln  Thr  Arg  Tyr  Phe  Glu  Arg
                    240                 245                 250

AGG  CAT  CCG  GAG  CTT  GCA  GGA  TCG  CCG  CGG  CTC  CGG  GCG  TAT  ATG  CTC       820
Arg  His  Pro  Glu  Leu  Ala  Gly  Ser  Pro  Arg  Leu  Arg  Ala  Tyr  Met  Leu
               255                 260                 265

CGC  ATT  GGT  CTT  GAC  CAA  CTC  TAT  CAG  AGC  TTG  GTT  GAC  GGC  AAT  TTC       868
Arg  Ile  Gly  Leu  Asp  Gln  Leu  Tyr  Gln  Ser  Leu  Val  Asp  Gly  Asn  Phe
          270                 275                 280

GAT  GAT  GCA  GCT  TGG  GCG  CAG  GGT  CGA  TGC  GAC  GCA  ATC  GTC  CGA  TCC       916
Asp  Asp  Ala  Ala  Trp  Ala  Gln  Gly  Arg  Cys  Asp  Ala  Ile  Val  Arg  Ser
     285                 290                 295

GGA  GCC  GGG  ACT  GTC  GGG  CGT  ACA  CAA  ATC  GCC  CGC  AGA  AGC  GCG  GCC       964
Gly  Ala  Gly  Thr  Val  Gly  Arg  Thr  Gln  Ile  Ala  Arg  Arg  Ser  Ala  Ala
300                 305                 310                 315

GTC  TGG  ACC  GAT  GGC  TGT  GTA  GAA  GTA  CTC  GCC  GAT  AGT  GGA  AAC  CGA      1012
Val  Trp  Thr  Asp  Gly  Cys  Val  Glu  Val  Leu  Ala  Asp  Ser  Gly  Asn  Arg
```

|       |       |       |       | 320   |       |       |       | 325   |       |       |            |            | 330 |      |
|-------|-------|-------|-------|-------|-------|-------|-------|-------|-------|-------|------------|------------|-----|------|
| CGC   | CCC   | AGC   | ACT   | CGT   | CCG   | AGG   | GCA   | AAG   | GAA   | TAGAGTAGAT | GCCGACCGGG |     | 1062 |
| Arg   | Pro   | Ser   | Thr   | Arg   | Pro   | Arg   | Ala   | Lys   | Glu   |            |            |     |      |
|       |       |       | 335   |       |       |       |       | 340   |       |            |            |     |      |

ATCC 1066

( 2 ) INFORMATION FOR SEQ ID NO:19:

( i ) SEQUENCE CHARACTERISTICS:
        ( A ) LENGTH: 341 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| Met | Lys | Lys | Pro | Glu | Leu | Thr | Ala | Thr | Ser | Val | Glu | Lys | Phe | Leu | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     |     | 15  |
| Glu | Lys | Phe | Asp | Ser | Val | Ser | Asp | Leu | Met | Gln | Leu | Ser | Glu | Gly | Glu |
|     |     |     | 20  |     |     |     |     | 25  |     |     |     |     | 30  |     |     |
| Glu | Ser | Arg | Ala | Phe | Ser | Phe | Asp | Val | Gly | Gly | Arg | Gly | Tyr | Val | Leu |
|     |     | 35  |     |     |     |     | 40  |     |     |     |     | 45  |     |     |     |
| Arg | Val | Asn | Ser | Cys | Ala | Asp | Gly | Phe | Tyr | Lys | Asp | Arg | Tyr | Val | Tyr |
|     | 50  |     |     |     |     | 55  |     |     |     |     | 60  |     |     |     |     |
| Arg | His | Phe | Ala | Ser | Ala | Ala | Leu | Pro | Ile | Pro | Glu | Val | Leu | Asp | Ile |
| 65  |     |     |     |     | 70  |     |     |     |     | 75  |     |     |     |     | 80  |
| Gly | Glu | Phe | Ser | Glu | Ser | Leu | Thr | Tyr | Cys | Ile | Ser | Arg | Arg | Ala | Gln |
|     |     |     |     | 85  |     |     |     |     | 90  |     |     |     |     | 95  |     |
| Gly | Val | Thr | Leu | Gln | Asp | Leu | Pro | Glu | Thr | Glu | Leu | Pro | Ala | Val | Leu |
|     |     |     |     | 100 |     |     |     |     | 105 |     |     |     |     | 110 |     |
| Gln | Pro | Val | Ala | Glu | Ala | Met | Asp | Ala | Ile | Ala | Ala | Ala | Asp | Leu | Ser |
|     |     |     | 115 |     |     |     |     | 120 |     |     |     |     | 125 |     |     |
| Gln | Thr | Ser | Gly | Phe | Gly | Pro | Phe | Gly | Pro | Gln | Gly | Ile | Gly | Gln | Tyr |
|     | 130 |     |     |     |     | 135 |     |     |     |     |     | 140 |     |     |     |
| Thr | Thr | Trp | Arg | Asp | Phe | Ile | Cys | Ala | Ile | Ala | Asp | Pro | His | Val | Tyr |
| 145 |     |     |     |     | 150 |     |     |     |     | 155 |     |     |     |     | 160 |
| His | Trp | Gln | Thr | Val | Met | Asp | Asp | Thr | Val | Ser | Ala | Ser | Val | Ala | Gln |
|     |     |     |     | 165 |     |     |     |     | 170 |     |     |     |     | 175 |     |
| Ala | Leu | Asp | Glu | Leu | Met | Leu | Trp | Ala | Glu | Asp | Cys | Pro | Glu | Val | Arg |
|     |     |     | 180 |     |     |     |     | 185 |     |     |     |     | 190 |     |     |
| His | Leu | Val | His | Ala | Asp | Phe | Gly | Ser | Asn | Asn | Val | Leu | Thr | Asp | Asn |
|     |     | 195 |     |     |     |     | 200 |     |     |     |     | 205 |     |     |     |
| Gly | Arg | Ile | Thr | Ala | Val | Ile | Asp | Trp | Ser | Glu | Ala | Met | Phe | Gly | Asp |
|     | 210 |     |     |     |     | 215 |     |     |     |     | 220 |     |     |     |     |
| Ser | Gln | Tyr | Glu | Val | Ala | Asn | Ile | Phe | Phe | Trp | Arg | Pro | Trp | Leu | Ala |
| 225 |     |     |     | 230 |     |     |     |     | 235 |     |     |     |     |     | 240 |
| Cys | Met | Glu | Gln | Gln | Thr | Arg | Tyr | Phe | Glu | Arg | Arg | His | Pro | Glu | Leu |
|     |     |     |     | 245 |     |     |     |     | 250 |     |     |     |     | 255 |     |
| Ala | Gly | Ser | Pro | Arg | Leu | Arg | Ala | Tyr | Met | Leu | Arg | Ile | Gly | Leu | Asp |
|     |     |     | 260 |     |     |     |     | 265 |     |     |     |     | 270 |     |     |
| Gln | Leu | Tyr | Gln | Ser | Leu | Val | Asp | Gly | Asn | Phe | Asp | Asp | Ala | Ala | Trp |
|     |     | 275 |     |     |     |     | 280 |     |     |     |     | 285 |     |     |     |
| Ala | Gln | Gly | Arg | Cys | Asp | Ala | Ile | Val | Arg | Ser | Gly | Ala | Gly | Thr | Val |
|     | 290 |     |     |     |     | 295 |     |     |     |     | 300 |     |     |     |     |
| Gly | Arg | Thr | Gln | Ile | Ala | Arg | Arg | Ser | Ala | Ala | Val | Trp | Thr | Asp | Gly |
| 305 |     |     |     |     | 310 |     |     |     |     | 315 |     |     |     |     | 320 |

Cys Val Glu Val Leu Ala Asp Ser Gly Asn Arg Arg Pro Ser Thr Arg
325                     330                     335

Pro Arg Ala Lys Glu
            340

( 2 ) INFORMATION FOR SEQ ID NO:20:

( i ) SEQUENCE CHARACTERISTICS:
        ( A ) LENGTH: 2325 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..2322

( x i ) SEQUENCE DESCRIPTION: SEQ ID NO:20:

| | | | | | | | | | | | | | | | | |
|---|---|---|---|---|---|---|---|---|---|---|---|---|---|---|---|---|
| ATG | ACT | ATG | GCT | GCC | AAC | ACC | GAT | CGC | GCG | GTC | TTG | CAG | GCG | GCG | CTG | 48 |
| Met | Thr | Met | Ala | Ala | Asn | Thr | Asp | Arg | Ala | Val | Leu | Gln | Ala | Ala | Leu | |
| 1 | | | | 5 | | | | | 10 | | | | | 15 | | |
| CCG | CCG | CTT | TCC | GGC | AGC | CTC | CCC | ATT | CCC | GGA | TTG | AGC | GCG | TCG | GTC | 96 |
| Pro | Pro | Leu | Ser | Gly | Ser | Leu | Pro | Ile | Pro | Gly | Leu | Ser | Ala | Ser | Val | |
| | | | 20 | | | | | 25 | | | | | 30 | | | |
| CGT | ATC | CAG | CGC | GAT | GCC | TGG | GGC | ATC | CCG | CAT | ATC | AAG | GCC | TCC | GGC | 144 |
| Arg | Ile | Gln | Arg | Asp | Ala | Trp | Gly | Ile | Pro | His | Ile | Lys | Ala | Ser | Gly | |
| | | 35 | | | | | 40 | | | | | 45 | | | | |
| GAG | GCC | GAT | GCC | TAT | CGC | GCG | CTG | GGC | TTC | GTC | CAT | GCG | CAG | GAC | CGC | 192 |
| Glu | Ala | Asp | Ala | Tyr | Arg | Ala | Leu | Gly | Phe | Val | His | Ala | Gln | Asp | Arg | |
| | 50 | | | | | 55 | | | | | 60 | | | | | |
| CTT | TTC | CAG | ATG | GAG | CTG | ACG | CGT | CGC | AAG | GCG | CTG | GGA | CGC | GCG | GCC | 240 |
| Leu | Phe | Gln | Met | Glu | Leu | Thr | Arg | Arg | Lys | Ala | Leu | Gly | Arg | Ala | Ala | |
| 65 | | | | | 70 | | | | | 75 | | | | | 80 | |
| GAA | TGG | CTG | GGT | GCC | GAG | GCC | GCC | GAG | GCC | GAT | ATC | CTC | GTG | CGC | CGG | 288 |
| Glu | Trp | Leu | Gly | Ala | Glu | Ala | Ala | Glu | Ala | Asp | Ile | Leu | Val | Arg | Arg | |
| | | | | 85 | | | | | 90 | | | | | 95 | | |
| CTC | GGT | ATG | GAA | AAA | GTC | TGC | CGA | CGC | GAT | TTC | GAG | GCC | CTG | GGC | GCC | 336 |
| Leu | Gly | Met | Glu | Lys | Val | Cys | Arg | Arg | Asp | Phe | Glu | Ala | Leu | Gly | Ala | |
| | | | 100 | | | | | 105 | | | | | 110 | | | |
| GAG | GCG | AAG | GAC | ATG | CTC | CGG | GCC | TAC | GTC | GCC | GGC | GTG | AAC | GCA | TTC | 384 |
| Glu | Ala | Lys | Asp | Met | Leu | Arg | Ala | Tyr | Val | Ala | Gly | Val | Asn | Ala | Phe | |
| | | 115 | | | | | 120 | | | | | 125 | | | | |
| CTG | GCT | TCC | GGT | GTT | CCC | CTG | CCT | GTC | GAA | TAC | GGA | TTG | CTC | GGA | GCA | 432 |
| Leu | Ala | Ser | Gly | Val | Pro | Leu | Pro | Val | Glu | Tyr | Gly | Leu | Leu | Gly | Ala | |
| | 130 | | | | | 135 | | | | | 140 | | | | | |
| GAG | CCG | GAG | CCC | TGG | GAG | CCT | TGG | CAC | AGC | ATC | GCG | GTG | ATG | CGC | CGG | 480 |
| Glu | Pro | Glu | Pro | Trp | Glu | Pro | Trp | His | Ser | Ile | Ala | Val | Met | Arg | Arg | |
| 145 | | | | | 150 | | | | | 155 | | | | | 160 | |
| CTG | GGC | CTG | CTG | ATG | GGT | TCG | GTC | TGG | TTC | AAG | CTC | TGG | CGG | ATG | CTG | 528 |
| Leu | Gly | Leu | Leu | Met | Gly | Ser | Val | Trp | Phe | Lys | Leu | Trp | Arg | Met | Leu | |
| | | | | 165 | | | | | 170 | | | | | 175 | | |
| GCG | CTG | CCG | GTG | GTC | GGA | GCC | GCG | AAT | GCG | CTG | AAG | CTG | CGC | TAT | GAC | 576 |
| Ala | Leu | Pro | Val | Val | Gly | Ala | Ala | Asn | Ala | Leu | Lys | Leu | Arg | Tyr | Asp | |
| | | | 180 | | | | | 185 | | | | | 190 | | | |
| GAT | GGC | GGC | CGC | GAT | TTG | CTC | TGC | ATC | CCG | CCG | GGC | GCC | GAA | GCG | GAT | 624 |
| Asp | Gly | Gly | Arg | Asp | Leu | Leu | Cys | Ile | Pro | Pro | Gly | Ala | Glu | Ala | Asp | |
| | | 195 | | | | | 200 | | | | | 205 | | | | |
| CGG | CTC | GAG | GCG | GAT | CTC | GCG | ACC | CTG | CGG | CCC | GCG | GTC | GAT | GCG | CTG | 672 |
| Arg | Leu | Glu | Ala | Asp | Leu | Ala | Thr | Leu | Arg | Pro | Ala | Val | Asp | Ala | Leu | |
| | 210 | | | | | 215 | | | | | 220 | | | | | |
| CTG | AAG | GCG | ATG | GGC | GGG | GAT | GCC | TCA | GAT | GCC | GCC | GGT | GGC | GGC | AGC | 720 |

| | | | | | | | | | | | | | | | | |
|---|---|---|---|---|---|---|---|---|---|---|---|---|---|---|---|---|
| Leu 225 | Lys | Ala | Met | Gly 230 | Gly | Asp | Ala | Ser | Asp 235 | Ala | Ala | Gly | Gly | Gly 240 | Ser | |
| AAC Asn | AAC Asn | TGG Trp | GCG Ala | GTC Val 245 | GCG Ala | CCG Pro | GGC Gly | CGT Arg | ACG Thr 250 | GCG Ala | ACC Thr | GGC Gly | CGG Arg | CCG Pro 255 | ATC Ile | 768 |
| CTC Leu | GCG Ala | GGC Gly | GAT Asp 260 | CCG Pro | CAT His | CGC Arg | GTC Val | TTC Phe | GAG Glu 265 | ATC Ile | CCC Pro | GGC Gly | ATG Met | TAT Tyr 270 | GCC Ala | 816 |
| CAG Gln | CAT His | CAT His 275 | CTG Leu | GCC Ala | TGC Cys | GAT Asp | CGC Arg 280 | TTC Phe | GAC Asp | ATG Met | ATC Ile | GGC Gly 285 | CTG Leu | ACC Thr | GTG Val | 864 |
| CCG Pro | GGC Gly | GTG Val 290 | CCG Pro | GGT Gly | TTT Phe | CCG Pro | CAT His 295 | TTC Phe | GCG Ala | CAT His | AAC Asn | GGC Gly 300 | AAG Lys | GTC Val | GCC Ala | 912 |
| TAC Tyr 305 | TGC Cys | GTC Val | ACC Thr | CAT His 310 | GCC Ala | TTC Phe | ATG Met | GAC Asp | ATT Ile 315 | CAC His | GAT Asp | CTC Leu | TAC Tyr | CTT Leu 320 | GAG Glu | 960 |
| CAG Gln | TTC Phe | GCG Ala | GAG Glu | GAG Glu 325 | GGC Gly | CGC Arg | AGG Arg | GCG Ala | CGG Arg 330 | TTC Phe | GGC Gly | AAC Asn | GAT Asp | TTC Phe 335 | GAG Glu | 1008 |
| CCC Pro | GCC Ala | GCC Ala | TGG Trp 340 | AGC Ser | CGG Arg | GAC Asp | CGT Arg | ATC Ile 345 | GCG Ala | GTC Val | CGG Arg | GGT Gly | GGT Gly 350 | GCC Ala | GAC Asp | 1056 |
| CGC Arg | GAA Glu | TTC Phe | GAT Asp 355 | ATC Ile | ATC Ile | GAG Glu | ACG Thr | CGC Arg 360 | CAT His | GGT Gly | CCC Pro | GTC Val | ATA Ile 365 | GCA Ala | GGC Gly | 1104 |
| GAT Asp | CCG Pro | CGC Arg 370 | GAT Asp | GGC Gly | GCA Ala | GCG Ala | CTC Leu 375 | ACG Thr | CTG Leu | CGC Arg | TCG Ser | GTC Val 380 | CAG Gln | TTC Phe | GCC Ala | 1152 |
| GAG Glu 385 | ACC Thr | GAT Asp | CTG Leu | TCC Ser | TTC Phe 390 | GAT Asp | TGC Cys | CTG Leu | ACG Thr | CGG Arg 395 | ATG Met | CCG Pro | GGC Gly | GCA Ala | TCG Ser 400 | 1200 |
| ACC Thr | GTG Val | GCG Ala | CAG Gln | CTC Leu 405 | TAC Tyr | GAC Asp | GCG Ala | ACG Thr | CGC Arg 410 | GGC Gly | TGG Trp | GGC Gly | CTG Leu | ATC Ile 415 | GAC Asp | 1248 |
| CAT His | AAT Asn | CTC Leu | GTC Val 420 | GCC Ala | GGG Gly | GAT Asp | GTC Val | GGG Gly 425 | GGC Gly | TCG Ser | ATC Ile | GGC Gly | CAT His 430 | CTG Leu | GTC Val | 1296 |
| CGC Arg | GCC Ala | CGT Arg 435 | GTC Val | CCG Pro | TCC Ser | CGC Arg | TCG Ser 440 | CGC Arg | GAA Glu | AAC Asn | GGC Gly | TGG Trp 445 | CTG Leu | CCG Pro | GTG Val | 1344 |
| CCG Pro | GGC Gly 450 | TGG Trp | TCC Ser | GGC Gly | GAG Glu | CAT His 455 | GAA Glu | TGG Trp | GGG Gly | GGT Gly | TGG Trp 460 | ATT Ile | CCG Pro | CAC His | GAG Glu | 1392 |
| GCG Ala 465 | ATG Met | CCG Pro | CGC Arg | GTG Val | ATC Ile 470 | GAT Asp | CCG Pro | CCG Pro | GGC Gly | ATC Ile 475 | ATC Ile | GTC Val | ACG Thr | GCG Ala 480 | | 1440 |
| AAT Asn | AAT Asn | CGC Arg | GTC Val | GTG Val 485 | GCC Ala | GAT Asp | GAC Asp | CAT His | CCC Pro 490 | GAT Asp | TAT Tyr | CTC Leu | TGC Cys | ACC Thr 495 | GAT Asp | 1488 |
| TGC Cys | CAT His | CCG Pro | CCC Pro 500 | TAC Tyr | CGC Arg | GCC Ala | GAG Glu | CGC Arg 505 | ATC Ile | ATG Met | AAG Lys | CGC Arg | CTG Leu 510 | GTC Val | GCC Ala | 1536 |
| AAT Asn | CCG Pro | GCT Ala 515 | TTC Phe | GCC Ala | GTC Val | GAC Asp | GAT Asp 520 | GCC Ala | GCG Ala | GCG Ala | ATC Ile | CAT His 525 | GCC Ala | GAT Asp | ACG Thr | 1584 |
| CTG Leu | TCG Ser | CCC Pro 530 | CAT His | GTC Val | GGG Gly | TTG Leu | CTG Leu 535 | CGC Arg | CGG Arg | AGG Arg | CTC Leu | GAG Glu 540 | GCG Ala | CTT Leu | GGA Gly | 1632 |
| GCC Ala | CGC Arg | GAC Asp | GAC Asp | TCC Ser | GCG Ala | GCC Ala | GAA Glu | GGG Gly | CTG Leu | AGG Arg | CAG Gln | ATG Met | CTC Leu | GTC Val | GCC Ala | 1680 |

| | | | | | | | | | | | | | | | |
|---|---|---|---|---|---|---|---|---|---|---|---|---|---|---|---|
| Ala | Arg | Asp | Asp | Ser | Ala | Ala | Glu | Gly | Leu | Arg | Gln | Met | Leu | Val | Ala |
| 545 | | | | 550 | | | | | 555 | | | | | | 560 |
| TGG | GAC | GGC | CGC | ATG | GAT | GCG | GCT | TCG | GAG | GTC | GCG | TCT | GCC | TAC | AAT | 1728
| Trp | Asp | Gly | Arg | Met | Asp | Ala | Ala | Ser | Glu | Val | Ala | Ser | Ala | Tyr | Asn |
| | | | | 565 | | | | | 570 | | | | | 575 | |
| GCG | TTC | CGC | AGG | GCG | CTG | ACG | CGG | CTG | GTG | ACG | GAC | CGC | AGC | GGG | CTG | 1776
| Ala | Phe | Arg | Arg | Ala | Leu | Thr | Arg | Leu | Val | Thr | Asp | Arg | Ser | Gly | Leu |
| | | 580 | | | | | 585 | | | | | 590 | | | |
| GAG | CAG | GCG | ATA | TCG | CAT | CCC | TTC | GCG | GCT | GTC | GCG | CCG | GGC | GTC | TCA | 1824
| Glu | Gln | Ala | Ile | Ser | His | Pro | Phe | Ala | Ala | Val | Ala | Pro | Gly | Val | Ser |
| | | 595 | | | | 600 | | | | | 605 | | | | |
| CCG | CAA | GGC | CAG | GTC | TGG | TGG | GCC | GTG | CCG | ACC | CTG | CTG | CGC | GAC | GAC | 1872
| Pro | Gln | Gly | Gln | Val | Trp | Trp | Ala | Val | Pro | Thr | Leu | Leu | Arg | Asp | Asp |
| | 610 | | | | | 615 | | | | 620 | | | | | |
| GAT | GCC | GGA | ATG | CTG | AAG | GGC | TGG | AGC | TGG | GAC | CAG | GCC | TTG | TCT | GAG | 1920
| Asp | Ala | Gly | Met | Leu | Lys | Gly | Trp | Ser | Trp | Asp | Gln | Ala | Leu | Ser | Glu |
| 625 | | | | 630 | | | | | 635 | | | | | | 640 |
| GCC | CTC | TCG | GTC | GCG | TCG | CAG | AAC | CTG | ACC | GGG | CGA | AGC | TGG | GGC | GAA | 1968
| Ala | Leu | Ser | Val | Ala | Ser | Gln | Asn | Leu | Thr | Gly | Arg | Ser | Trp | Gly | Glu |
| | | | | 645 | | | | | 650 | | | | | 655 | |
| GAG | CAT | CGG | CCG | CGC | TTC | ACG | CAT | CCG | CTT | GCC | ACG | CAA | TTC | CCG | GCC | 2016
| Glu | His | Arg | Pro | Arg | Phe | Thr | His | Pro | Leu | Ala | Thr | Gln | Phe | Pro | Ala |
| | | | 660 | | | | | 665 | | | | | 670 | | |
| TGG | GCG | GGG | CTG | CTG | AAT | CCG | GCT | TCC | CGT | CCG | ATC | GGC | GGC | GAT | GGC | 2064
| Trp | Ala | Gly | Leu | Leu | Asn | Pro | Ala | Ser | Arg | Pro | Ile | Gly | Gly | Asp | Gly |
| | | 675 | | | | | 680 | | | | | 685 | | | |
| GAC | ACC | GTG | CTG | GCG | AAC | GGG | CTC | GTC | CCG | TCA | GCC | GGG | CCG | CAG | GCG | 2112
| Asp | Thr | Val | Leu | Ala | Asn | Gly | Leu | Val | Pro | Ser | Ala | Gly | Pro | Gln | Ala |
| | 690 | | | | | 695 | | | | | 700 | | | | |
| ACC | TAT | GGC | GCC | CTG | TCG | CGC | TAC | GTC | TTT | GAT | GTC | GGC | AAT | TGG | GAC | 2160
| Thr | Tyr | Gly | Ala | Leu | Ser | Arg | Tyr | Val | Phe | Asp | Val | Gly | Asn | Trp | Asp |
| 705 | | | | 710 | | | | | 715 | | | | | | 720 |
| AAT | AGC | CGC | TGG | GTC | GTC | TTC | CAC | GGC | GCC | TCC | GGG | CAT | CCG | GCC | AGC | 2208
| Asn | Ser | Arg | Trp | Val | Val | Phe | His | Gly | Ala | Ser | Gly | His | Pro | Ala | Ser |
| | | | | 725 | | | | | 730 | | | | | 735 | |
| GCC | CAT | TAT | GCC | GAT | CAG | AAT | GCG | CCC | TGG | AGC | GAC | TGT | GCG | ATG | GTG | 2256
| Ala | His | Tyr | Ala | Asp | Gln | Asn | Ala | Pro | Trp | Ser | Asp | Cys | Ala | Met | Val |
| | | | 740 | | | | | 745 | | | | | 750 | | |
| CCG | ATG | CTC | TAT | AGC | TGG | GAC | AGG | ATC | GCG | GCA | GAG | GCC | GTG | ACG | TCG | 2304
| Pro | Met | Leu | Tyr | Ser | Trp | Asp | Arg | Ile | Ala | Ala | Glu | Ala | Val | Thr | Ser |
| | | 755 | | | | | 760 | | | | | 765 | | | |
| CAG | GAA | CTC | GTC | CCG | GCC | TGA | | | | | | | | | | 2325
| Gln | Glu | Leu | Val | Pro | Ala | | | | | | | | | | |
| | 770 | | | | | | | | | | | | | | |

( 2 ) INFORMATION FOR SEQ ID NO:21:

( i ) SEQUENCE CHARACTERISTICS:
        ( A ) LENGTH: 774 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| | | | | | | | | | | | | | | |
|---|---|---|---|---|---|---|---|---|---|---|---|---|---|---|
| Met | Thr | Met | Ala | Ala | Asn | Thr | Asp | Arg | Ala | Val | Leu | Gln | Ala | Ala | Leu |
| 1 | | | | 5 | | | | | 10 | | | | | 15 |
| Pro | Pro | Leu | Ser | Gly | Ser | Leu | Pro | Ile | Pro | Gly | Leu | Ser | Ala | Ser | Val |
| | | | 20 | | | | | 25 | | | | | 30 | |
| Arg | Ile | Gln | Arg | Asp | Ala | Trp | Gly | Ile | Pro | His | Ile | Lys | Ala | Ser | Gly |
| | | 35 | | | | | 40 | | | | | 45 | | |

-continued

| | | | | | | | | | | | | | | |
|---|---|---|---|---|---|---|---|---|---|---|---|---|---|---|
|Glu|Ala|Asp|Ala|Tyr|Arg|Ala|Leu|Gly|Phe|Val|His|Ala|Gln|Asp|Arg|
| |50| | | |55| | | | |60| | | | |
|Leu|Phe|Gln|Met|Glu|Leu|Thr|Arg|Arg|Lys|Ala|Leu|Gly|Arg|Ala|Ala|
|65| | | | |70| | | | |75| | | | |80|
|Glu|Trp|Leu|Gly|Ala|Glu|Ala|Ala|Glu|Ala|Asp|Ile|Leu|Val|Arg|Arg|
| | | | |85| | | | |90| | | | |95| |
|Leu|Gly|Met|Glu|Lys|Val|Cys|Arg|Arg|Asp|Phe|Glu|Ala|Leu|Gly|Ala|
| | | |100| | | | |105| | | | |110| | |
|Glu|Ala|Lys|Asp|Met|Leu|Arg|Ala|Tyr|Val|Ala|Gly|Val|Asn|Ala|Phe|
| | |115| | | |120| | | | |125| | | | |
|Leu|Ala|Ser|Gly|Val|Pro|Leu|Pro|Val|Glu|Tyr|Gly|Leu|Leu|Gly|Ala|
| |130| | | |135| | | | |140| | | | | |
|Glu|Pro|Glu|Pro|Trp|Glu|Pro|Trp|His|Ser|Ile|Ala|Val|Met|Arg|Arg|
|145| | | |150| | | | |155| | | | |160| |
|Leu|Gly|Leu|Leu|Met|Gly|Ser|Val|Trp|Phe|Lys|Leu|Trp|Arg|Met|Leu|
| | | | |165| | | | |170| | | | |175| |
|Ala|Leu|Pro|Val|Val|Gly|Ala|Ala|Asn|Ala|Leu|Lys|Leu|Arg|Tyr|Asp|
| | | |180| | | | |185| | | | |190| | |
|Asp|Gly|Gly|Arg|Asp|Leu|Leu|Cys|Ile|Pro|Pro|Gly|Ala|Glu|Ala|Asp|
| | |195| | | | |200| | | | |205| | | |
|Arg|Leu|Glu|Ala|Asp|Leu|Ala|Thr|Leu|Arg|Pro|Ala|Val|Asp|Ala|Leu|
| |210| | | | |215| | | | |220| | | | |
|Leu|Lys|Ala|Met|Gly|Gly|Asp|Ala|Ser|Asp|Ala|Ala|Gly|Gly|Gly|Ser|
|225| | | |230| | | | |235| | | | | |240|
|Asn|Asn|Trp|Ala|Val|Ala|Pro|Gly|Arg|Thr|Ala|Thr|Gly|Arg|Pro|Ile|
| | | |245| | | | |250| | | | |255| | |
|Leu|Ala|Gly|Asp|Pro|His|Arg|Val|Phe|Glu|Ile|Pro|Gly|Met|Tyr|Ala|
| | | |260| | | | |265| | | | |270| | |
|Gln|His|His|Leu|Ala|Cys|Asp|Arg|Phe|Asp|Met|Ile|Gly|Leu|Thr|Val|
| | |275| | | | |280| | | | |285| | | |
|Pro|Gly|Val|Pro|Gly|Phe|Pro|His|Phe|Ala|His|Asn|Gly|Lys|Val|Ala|
| |290| | | | |295| | | | |300| | | | |
|Tyr|Cys|Val|Thr|His|Ala|Phe|Met|Asp|Ile|His|Asp|Leu|Tyr|Leu|Glu|
|305| | | | |310| | | | |315| | | | |320| |
|Gln|Phe|Ala|Glu|Glu|Gly|Arg|Arg|Ala|Arg|Phe|Gly|Asn|Asp|Phe|Glu|
| | | | |325| | | | |330| | | | |335| |
|Pro|Ala|Ala|Trp|Ser|Arg|Asp|Arg|Ile|Ala|Val|Arg|Gly|Gly|Ala|Asp|
| | | |340| | | | |345| | | | |350| | |
|Arg|Glu|Phe|Asp|Ile|Ile|Glu|Thr|Arg|His|Gly|Pro|Val|Ile|Ala|Gly|
| | |355| | | | |360| | | | |365| | | |
|Asp|Pro|Arg|Asp|Gly|Ala|Ala|Leu|Thr|Leu|Arg|Ser|Val|Gln|Phe|Ala|
| |370| | | | |375| | | | |380| | | | |
|Glu|Thr|Asp|Leu|Ser|Phe|Asp|Cys|Leu|Thr|Arg|Met|Pro|Gly|Ala|Ser|
|385| | | | |390| | | | |395| | | | |400| |
|Thr|Val|Ala|Gln|Leu|Tyr|Asp|Ala|Thr|Arg|Gly|Trp|Gly|Leu|Ile|Asp|
| | | | |405| | | | |410| | | | |415| |
|His|Asn|Leu|Val|Ala|Gly|Asp|Val|Gly|Gly|Ser|Ile|Gly|His|Leu|Val|
| | | |420| | | | |425| | | | |430| | |
|Arg|Ala|Arg|Val|Pro|Ser|Arg|Ser|Arg|Glu|Asn|Gly|Trp|Leu|Pro|Val|
| | |435| | | | |440| | | | |445| | | |
|Pro|Gly|Trp|Ser|Gly|Glu|His|Glu|Trp|Gly|Gly|Trp|Ile|Pro|His|Glu|
| |450| | | | |455| | | | |460| | | | |
|Ala|Met|Pro|Arg|Val|Ile|Asp|Pro|Pro|Gly|Gly|Ile|Ile|Val|Thr|Ala|
|465| | | |470| | | | |475| | | | | |480|

| | | | | | | | | | | | | | |
|---|---|---|---|---|---|---|---|---|---|---|---|---|---|
|Asn|Asn|Arg|Val|Val 485|Ala|Asp|Asp|His|Pro 490|Asp|Tyr|Leu|Cys|Thr|Asp 495|

Asn Asn Arg Val Val Ala Asp Asp His Pro Asp Tyr Leu Cys Thr Asp
                    485                 490                 495

Cys His Pro Pro Tyr Arg Ala Glu Arg Ile Met Lys Arg Leu Val Ala
            500                 505                 510

Asn Pro Ala Phe Ala Val Asp Asp Ala Ala Ala Ile His Ala Asp Thr
            515                 520                 525

Leu Ser Pro His Val Gly Leu Leu Arg Arg Arg Leu Glu Ala Leu Gly
    530                 535                 540

Ala Arg Asp Asp Ser Ala Ala Glu Gly Leu Arg Gln Met Leu Val Ala
545                 550                 555                 560

Trp Asp Gly Arg Met Asp Ala Ala Ser Glu Val Ala Ser Ala Tyr Asn
                565                 570                 575

Ala Phe Arg Arg Ala Leu Thr Arg Leu Val Thr Asp Arg Ser Gly Leu
            580                 585                 590

Glu Gln Ala Ile Ser His Pro Phe Ala Ala Val Ala Pro Gly Val Ser
            595                 600                 605

Pro Gln Gly Gln Val Trp Trp Ala Val Pro Thr Leu Leu Arg Asp Asp
    610                 615                 620

Asp Ala Gly Met Leu Lys Gly Trp Ser Trp Asp Gln Ala Leu Ser Glu
625                 630                 635                 640

Ala Leu Ser Val Ala Ser Gln Asn Leu Thr Gly Arg Ser Trp Gly Glu
                645                 650                 655

Glu His Arg Pro Arg Phe Thr His Pro Leu Ala Thr Gln Phe Pro Ala
            660                 665                 670

Trp Ala Gly Leu Leu Asn Pro Ala Ser Arg Pro Ile Gly Gly Asp Gly
            675                 680                 685

Asp Thr Val Leu Ala Asn Gly Leu Val Pro Ser Ala Gly Pro Gln Ala
    690                 695                 700

Thr Tyr Gly Ala Leu Ser Arg Tyr Val Phe Asp Val Gly Asn Trp Asp
705                 710                 715                 720

Asn Ser Arg Trp Val Val Phe His Gly Ala Ser Gly His Pro Ala Ser
                725                 730                 735

Ala His Tyr Ala Asp Gln Asn Ala Pro Trp Ser Asp Cys Ala Met Val
            740                 745                 750

Pro Met Leu Tyr Ser Trp Asp Arg Ile Ala Ala Glu Ala Val Thr Ser
            755                 760                 765

Gln Glu Leu Val Pro Ala
    770

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:22:

GGATCCGGTA CCAAGGACGT C                  21

( 2 ) INFORMATION FOR SEQ ID NO:23:

( i ) SEQUENCE CHARACTERISTICS:
        ( A ) LENGTH: 169 base pairs
        ( B ) TYPE: nucleic acid

```
        ( C ) STRANDEDNESS: unknown
        ( D ) TOPOLOGY: linear ( i i ) MOLECULE TYPE: DNA (genomic)

( x i ) SEQUENCE DESCRIPTION: SEQ ID NO:23:

GGATCCCCCG CGTGAGCTTG CCCAGATTCC GACAAGCAAT GACGTCCGAC AAGGAATGAC         60

TATGGCTGCC AACACCGATC GCGCGGTCTT GCAGGCGGCG CTGCCGCCGC TTTCCGGCAG        120

CCTCCCCATT CCCGGATTGA GCGCGTCGGT CCGTATCCAG CGCGATGCC                    169

( 2 ) INFORMATION FOR SEQ ID NO:24:

( i ) SEQUENCE CHARACTERISTICS:
                ( A ) LENGTH: 1243 base pairs
                ( B ) TYPE: nucleic acid
                ( C ) STRANDEDNESS: unknown
                ( D ) TOPOLOGY: unknown ( i i ) MOLECULE TYPE: DNA (genomic)

( i x ) FEATURE:
                ( A ) NAME/KEY: CDS
                ( B ) LOCATION: 11..1093

( x i ) SEQUENCE DESCRIPTION: SEQ ID NO:24:
```

```
GGATCCAATC ATG TCC AAC ACA ATC GTC GTC GTT GGT GCC GGT GTC ATT          49
           Met Ser Asn Thr Ile Val Val Val Gly Ala Gly Val Ile
             1               5                  10

GGC TTG ACG TCG GCC TTG TTG CTC TCC AAG AAC AAG GGC AAC AAG ATC          97
Gly Leu Thr Ser Ala Leu Leu Leu Ser Lys Asn Lys Gly Asn Lys Ile
 15                  20                  25

ACC GTC GTG GCC AAG CAC ATG CCC GGC GAC TAT GAC GTT GAA TAC GCC         145
Thr Val Val Ala Lys His Met Pro Gly Asp Tyr Asp Val Glu Tyr Ala
 30                  35                  40                  45

TCG CCT TTT GCT GGT GCC AAC CAC TCC CCC ATG GCG ACG GAA GAG AGC         193
Ser Pro Phe Ala Gly Ala Asn His Ser Pro Met Ala Thr Glu Glu Ser
         50                  55                  60

AGC GAA TGG GAA CGT CGC ACT TGG TAC GAG TTT AAG AGA CTG GTC GAG         241
Ser Glu Trp Glu Arg Arg Thr Trp Tyr Glu Phe Lys Arg Leu Val Glu
             65                  70                  75

GAG GTC CCT GAG GCC GGT GTT CAT TTC CAG AAG TCT CGC ATC CAG AGG         289
Glu Val Pro Glu Ala Gly Val His Phe Gln Lys Ser Arg Ile Gln Arg
                 80                  85                  90

CGC AAT GTG GAC ACT GAA AAG GCG CAG AGG TCT GGT TTC CCA GAC GCC         337
Arg Asn Val Asp Thr Glu Lys Ala Gln Arg Ser Gly Phe Pro Asp Ala
             95                 100                 105

CTC TTC TCG AAA GAA CCC TGG TTC AAG AAC ATG TTT GAG GAC TTC CGT         385
Leu Phe Ser Lys Glu Pro Trp Phe Lys Asn Met Phe Glu Asp Phe Arg
110                 115                 120                 125

GAG CAG CAC CCT AGC GAG GTC ATC CCC GGT TAC GAC TCT GGC TGC GAG         433
Glu Gln His Pro Ser Glu Val Ile Pro Gly Tyr Asp Ser Gly Cys Glu
                130                 135                 140

TTC ACA TCG GTG TGC ATC AAC ACG GCC ATC TAC CTC CCC TGG CTC CTC         481
Phe Thr Ser Val Cys Ile Asn Thr Ala Ile Tyr Leu Pro Trp Leu Leu
                    145                 150                 155

GGC CAG TGC ATC AAG AAT GGC GTC ATC GTC AAG CGC GCC ATC CTC AAC         529
Gly Gln Cys Ile Lys Asn Gly Val Ile Val Lys Arg Ala Ile Leu Asn
                160                 165                 170

GAC ATT AGC GAG GCC AAG AAG CTG AGC CAC GCG GGC AAG ACG CCC AAT         577
Asp Ile Ser Glu Ala Lys Lys Leu Ser His Ala Gly Lys Thr Pro Asn
                175                 180                 185

ATC ATC GTC AAC GCC ACG GGT CTC GGC TCC TAC AAG CTG GGC GGT GTC         625
Ile Ile Val Asn Ala Thr Gly Leu Gly Ser Tyr Lys Leu Gly Gly Val
```

```
                                                                                                 190
GAG  GAC  AAG  ACC  ATG  GCG  CCT  GCG  CGG  GGA  CAG  ATT  GTG  GTT  GTG  CGC        673
Glu  Asp  Lys  Thr  Met  Ala  Pro  Ala  Arg  Gly  Gln  Ile  Val  Val  Val  Arg
                    210                      215                     220

AAC  GAG  AGC  AGC  CCC  ATG  CTC  CTC  ACT  TCA  GGT  GTC  GAG  GAC  GGC  GGT        721
Asn  Glu  Ser  Ser  Pro  Met  Leu  Leu  Thr  Ser  Gly  Val  Glu  Asp  Gly  Gly
               225                      230                     235

GCT  GAT  GTC  ATG  TAC  TTG  ATG  CAG  CGA  GCA  GCT  GGC  GGT  GGC  ACC  ATC        769
Ala  Asp  Val  Met  Tyr  Leu  Met  Gln  Arg  Ala  Ala  Gly  Gly  Gly  Thr  Ile
          240                      245                     250

CTG  GGC  GGT  ACC  TAC  GAC  GTT  GGC  AAC  TGG  GAG  TCT  CAG  CCA  GAC  CCC        817
Leu  Gly  Gly  Thr  Tyr  Asp  Val  Gly  Asn  Trp  Glu  Ser  Gln  Pro  Asp  Pro
     255                      260                     265

AAC  ATC  GCG  AAT  CGC  ATC  ATG  CAG  CGC  ATC  GTC  GAG  GTG  CGG  CCC  GAG        865
Asn  Ile  Ala  Asn  Arg  Ile  Met  Gln  Arg  Ile  Val  Glu  Val  Arg  Pro  Glu
270                      275                     280                     285

ATT  GCC  AAC  GGC  AAG  GGC  GTC  AAG  GGG  CTG  AGC  GTG  ATC  CGA  CAC  GCC        913
Ile  Ala  Asn  Gly  Lys  Gly  Val  Lys  Gly  Leu  Ser  Val  Ile  Arg  His  Ala
                    290                      295                     300

GTC  GGC  ATG  CGG  CCG  TGG  CGA  AAG  GAC  GGA  GTC  AGG  ATC  GAG  GAG  GAG        961
Val  Gly  Met  Arg  Pro  Trp  Arg  Lys  Asp  Gly  Val  Arg  Ile  Glu  Glu  Glu
               305                      310                     315

AAG  CTG  GAT  GAT  GAG  ACT  TGG  ATC  GTG  CAC  AAC  TAC  GGA  CAC  TCT  GGA       1009
Lys  Leu  Asp  Asp  Glu  Thr  Trp  Ile  Val  His  Asn  Tyr  Gly  His  Ser  Gly
          320                      325                     330

TGG  GGT  TAC  CAG  GGT  TCG  TAT  GGT  TGT  GCT  GAG  AAT  GTA  GTC  CAG  TTG       1057
Trp  Gly  Tyr  Gln  Gly  Ser  Tyr  Gly  Cys  Ala  Glu  Asn  Val  Val  Gln  Leu
     335                      340                     345

GTT  GAC  AAG  GTC  GGC  AAG  GCG  GCC  AAG  TCT  AAG  CTG  TAGTTGAAAA                 1103
Val  Asp  Lys  Val  Gly  Lys  Ala  Ala  Lys  Ser  Lys  Leu
350                      355                     360

GGCCTGAATG  AGTAATAGTA  ATTGGATATT  GGAAATACCG  TATTTGCCCT  CGAAAAAAAA                1163

AAAAAAAAAA  AAAAAAAAAA  AAAAGTACCT  TCTGAGGCGG  AAAGAACCAG  CCGGATCAAT                1223

TCGAGCTCGC  CCGGGGATCC                                                                 1243
```

( 2 ) INFORMATION FOR SEQ ID NO:25:

( i ) SEQUENCE CHARACTERISTICS:
        ( A ) LENGTH: 361 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Met  Ser  Asn  Thr  Ile  Val  Val  Gly  Ala  Gly  Val  Ile  Gly  Leu  Thr
  1             5                     10                     15

Ser  Ala  Leu  Leu  Leu  Ser  Lys  Asn  Lys  Gly  Asn  Lys  Ile  Thr  Val  Val
               20                      25                      30

Ala  Lys  His  Met  Pro  Gly  Asp  Tyr  Asp  Val  Glu  Tyr  Ala  Ser  Pro  Phe
          35                      40                      45

Ala  Gly  Ala  Asn  His  Ser  Pro  Met  Ala  Thr  Glu  Glu  Ser  Ser  Glu  Trp
     50                      55                      60

Glu  Arg  Arg  Thr  Trp  Tyr  Glu  Phe  Lys  Arg  Leu  Val  Glu  Val  Pro
 65                      70                      75                      80

Glu  Ala  Gly  Val  His  Phe  Gln  Lys  Ser  Arg  Ile  Gln  Arg  Arg  Asn  Val
                    85                      90                      95

Asp  Thr  Glu  Lys  Ala  Gln  Arg  Ser  Gly  Phe  Pro  Asp  Ala  Leu  Phe  Ser
               100                     105                     110
```

| Lys | Glu | Pro | Trp | Phe | Lys | Asn | Met | Phe | Glu | Asp | Phe | Arg | Glu | Gln | His |
| | | 115 | | | | | 120 | | | | | 125 | | | |
| Pro | Ser | Glu | Val | Ile | Pro | Gly | Tyr | Asp | Ser | Gly | Cys | Glu | Phe | Thr | Ser |
| | | 130 | | | | 135 | | | | | 140 | | | | |
| Val | Cys | Ile | Asn | Thr | Ala | Ile | Tyr | Leu | Pro | Trp | Leu | Leu | Gly | Gln | Cys |
| 145 | | | | | 150 | | | | | 155 | | | | | 160 |
| Ile | Lys | Asn | Gly | Val | Ile | Val | Lys | Arg | Ala | Ile | Leu | Asn | Asp | Ile | Ser |
| | | | | 165 | | | | | 170 | | | | | 175 | |
| Glu | Ala | Lys | Lys | Leu | Ser | His | Ala | Gly | Lys | Thr | Pro | Asn | Ile | Ile | Val |
| | | | | 180 | | | | 185 | | | | | 190 | | |
| Asn | Ala | Thr | Gly | Leu | Gly | Ser | Tyr | Lys | Leu | Gly | Gly | Val | Glu | Asp | Lys |
| | | 195 | | | | | 200 | | | | | 205 | | | |
| Thr | Met | Ala | Pro | Ala | Arg | Gly | Gln | Ile | Val | Val | Arg | Asn | Glu | Ser |
| | 210 | | | | | 215 | | | | | 220 | | | |
| Ser | Pro | Met | Leu | Leu | Thr | Ser | Gly | Val | Glu | Asp | Gly | Gly | Ala | Asp | Val |
| 225 | | | | | 230 | | | | | 235 | | | | | 240 |
| Met | Tyr | Leu | Met | Gln | Arg | Ala | Ala | Gly | Gly | Gly | Thr | Ile | Leu | Gly | Gly |
| | | | | 245 | | | | | 250 | | | | | 255 | |
| Thr | Tyr | Asp | Val | Gly | Asn | Trp | Glu | Ser | Gln | Pro | Asp | Pro | Asn | Ile | Ala |
| | | | 260 | | | | | 265 | | | | | 270 | | |
| Asn | Arg | Ile | Met | Gln | Arg | Ile | Val | Glu | Val | Arg | Pro | Glu | Ile | Ala | Asn |
| | | 275 | | | | | 280 | | | | | 285 | | | |
| Gly | Lys | Gly | Val | Lys | Gly | Leu | Ser | Val | Ile | Arg | His | Ala | Val | Gly | Met |
| | 290 | | | | | 295 | | | | | 300 | | | | |
| Arg | Pro | Trp | Arg | Lys | Asp | Gly | Val | Arg | Ile | Glu | Glu | Glu | Lys | Leu | Asp |
| 305 | | | | | 310 | | | | | 315 | | | | | 320 |
| Asp | Glu | Thr | Trp | Ile | Val | His | Asn | Tyr | Gly | His | Ser | Gly | Trp | Gly | Tyr |
| | | | | 325 | | | | | 330 | | | | | 335 | |
| Gln | Gly | Ser | Tyr | Gly | Cys | Ala | Glu | Asn | Val | Val | Gln | Leu | Val | Asp | Lys |
| | | | 340 | | | | 345 | | | | | 350 | | | |
| Val | Gly | Lys | Ala | Ala | Lys | Ser | Lys | Leu |
| | | 355 | | | | | 360 | |

( 2 ) INFORMATION FOR SEQ ID NO:26:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:26:

CTATTCGGCG ATGAC         15

( 2 ) INFORMATION FOR SEQ ID NO:27:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:27:

AAGGAGAAGA AGCTC         15

( 2 ) INFORMATION FOR SEQ ID NO:28:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:28:

CTCCTTGTCA TC    12

( 2 ) INFORMATION FOR SEQ ID NO:29:

( i ) SEQUENCE CHARACTERISTICS:
        ( A ) LENGTH: 31 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:29:

CATGAGCCAT ATTCAACGGG AAACGTCTTG C    31

( 2 ) INFORMATION FOR SEQ ID NO:30:

( i ) SEQUENCE CHARACTERISTICS:
        ( A ) LENGTH: 31 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:30:

TCGAGCAAGA CGTTTCCCGT TGAATATGGC T    31

( 2 ) INFORMATION FOR SEQ ID NO:31:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:31:

TTTTTCATAG CTGTTTCCTG TGGATCCG    28

( 2 ) INFORMATION FOR SEQ ID NO:32:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:32:

AATTCGGATC CACAGGAAAC AGCTATGAAA AAG    33

( 2 ) INFORMATION FOR SEQ ID NO:33:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:33:

GATCCGGTAC CAAGGACGT  19

( 2 ) INFORMATION FOR SEQ ID NO:34:

( i ) SEQUENCE CHARACTERISTICS:
        ( A ) LENGTH: 11 base pairs
        ( B ) TYPE: nucleic acid
        ( C ) STRANDEDNESS: unknown
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:34:

CCTTGGTACC G  11

PROCESS FOR PRODUCING 7-AMINOCEPHEM COMPOUND OR SALTS THEREOF

This is a continuation, of application Ser. No. 07/631,906 filed on Dec. 21, 1990, now abandoned.

FIELD OF THE INVENTION

This invention relates to a process for producing 7-aminocephem compound or salts thereof. More particularly, the invention relates to a process for producing 7-aminocephem compound or salts thereof, a vector to be used in said process, cephalosporin compound-producing microorganisms transformed with said vector, and a DNA fragment having the promoter activity of the *Acremonium chrysogenum* alkaline protease gene, among others.

BACKGROUND OF THE INVENTION

7-Aminocephem compound of the formula:

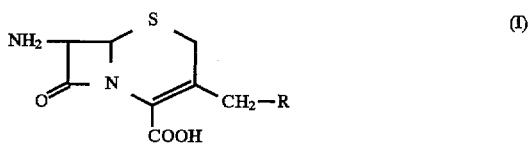

wherein R is an acetoxy, hydroxy or hydrogen, is the most important starting material for the production of semisynthetic cephalosporin antibiotics and is worldwidely used in a number of pharmaceutical factories throughout the world. At present, the 7-aminocephem compound (I) is produced by a two-step process which comprises the step of cultivating in a nutrient medium a cephalosporin compound-producing strain belonging to the species *Acremonium chrysogenum* and capable of producing a cephalosporin compound of the formula:

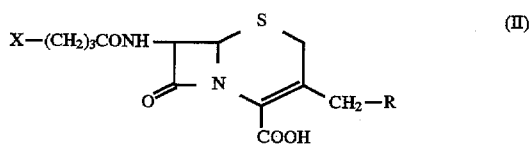

wherein R is as defined above and X is —CH(NH$_2$)—COOH, —CO—COOH or —COOH, and recovering the cephalosporin compound (II) from the cultured broth and the step of chemically or enzymatically eliminating the acyl group at 7 position such as the α-aminoadipoyl group, from the cephalosporin compound (II). For effecting the latter step deacylation chemically, the so-called iminoetherification process (F. M. Huber et al., "Cephalosporins and Penicillins, Chemistry and Biology", page 27, Academic Press, 1972), which involves a series of chemical reactions, is used for eliminating the 7-position acyl group such as the α-aminoadipoyl group of the cephalosporin compound (II). Regrettably, however, this process requires an expensive chemical plant and complicated operations. Enzymatic deacylation also requires complicated operations as well as a separate fermentation plant.

Accordingly the present inventors made investigations in an attempt to produce 7-aminocephem compound (I) directly in one step without the above-mentioned deacylation step by causing microorganisms to fermentatively produce the 7-aminocephem compound (I). Any microorganism capable of directly producing any of the 7-aminocephem compound (I) has not yet been discovered in the natural world in spite of efforts made by researchers all over the world. No report has-been presented as yet about a success in creating an 7-aminocephem compound (I)-producing microorganism by modifying a microorganism by means of mutation treatment or using genetic engineering techniques, because the difficulty of the task is great.

Facing such difficult task, the present inventors made intensive investigations, after which a vector for producing 7-aminocephem compound (I) which contains one or more promoter(s) for *Acremonium chrysogenum* and gene(s) for enzyme(s) capable of converting the cephalosporin compound (II) to the corresponding 7-aminocephem compound (I), with said gene(s) connected to said promoter(s), was newly constructed and the cephalosporin compound (II)-producing microorganism belonging to the species *Acremonium chrysogenum* was transformed with said vector and cultivated. Surprisingly, the desired 7-aminocephem compound (I) was found accumulated in the culture. Further investigations based on this fact have now led to completion of this invention.

SUMMARY OF THE INVENTION

This invention provides a process for producing 7-aminocephem compound (I) which comprises cultivating in a nutrient medium a 7-aminocephem compound (I)-producing microorganism, for example a cephalosporin compound (II)-producing microorganism belonging to the species *Acremonium chrysogenum* transformed with a vector for producing 7-aminocephem compounds (I) which contains one or more promoter(s) for *Acremonium chrysogenum* and gene(s) for enzyme(s) capable of converting the cephalosporin compound (II) to the corresponding 7-aminocephem compound. (I), with said gene(s) connected to said promoter(s), and recovering the 7-aminocephem compound (I) from the cultured broth.

λgt-Protease2: only the insert portion of λgt11 is indicated;

λ-G-Protease-1413 and λ-G-Protease-0112: only the insert portions into λgtWES·λB are indicated;

pGBR3-EH1 and pGBR2-EH1: only the insert portions into pBR322 are indicated.

Figure 1A:
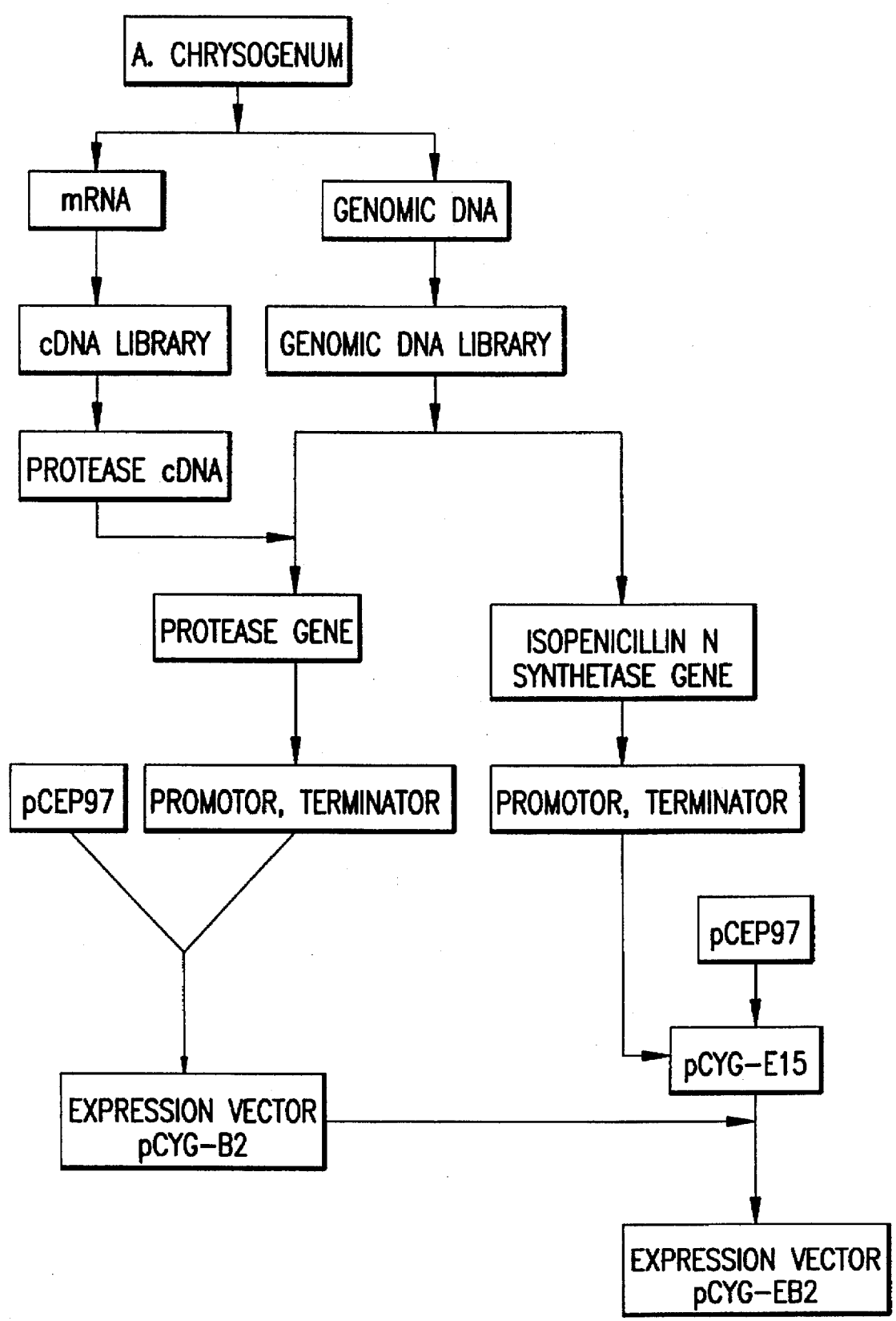
FIG. 1A schematically shows the procedure followed in Example 1.
Figure 1B:
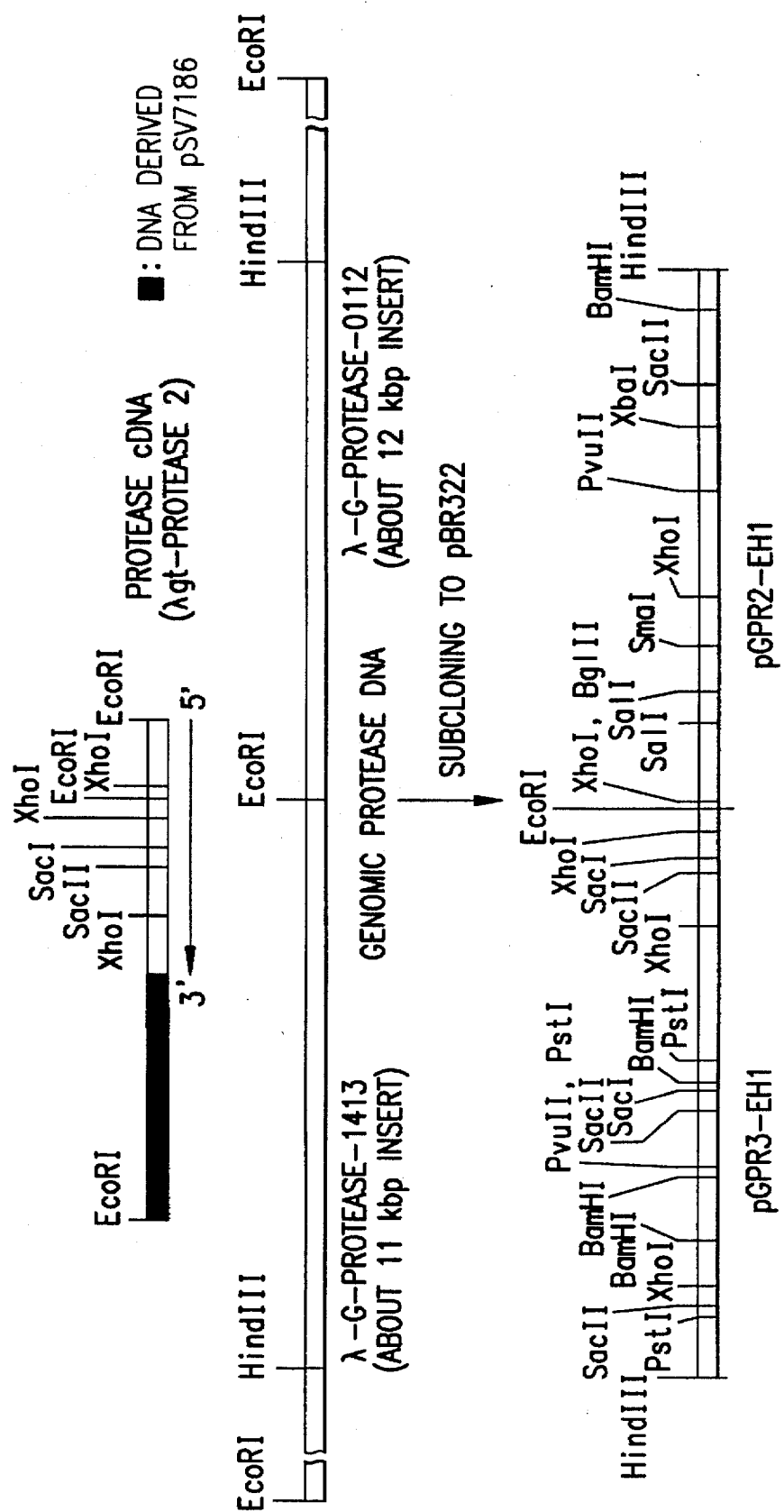
FIG. 1B shows the restriction enzyme cleavage map of an alkaline protease cDNA and that of a genomic alkaline protease DNA.
Figure 1C:
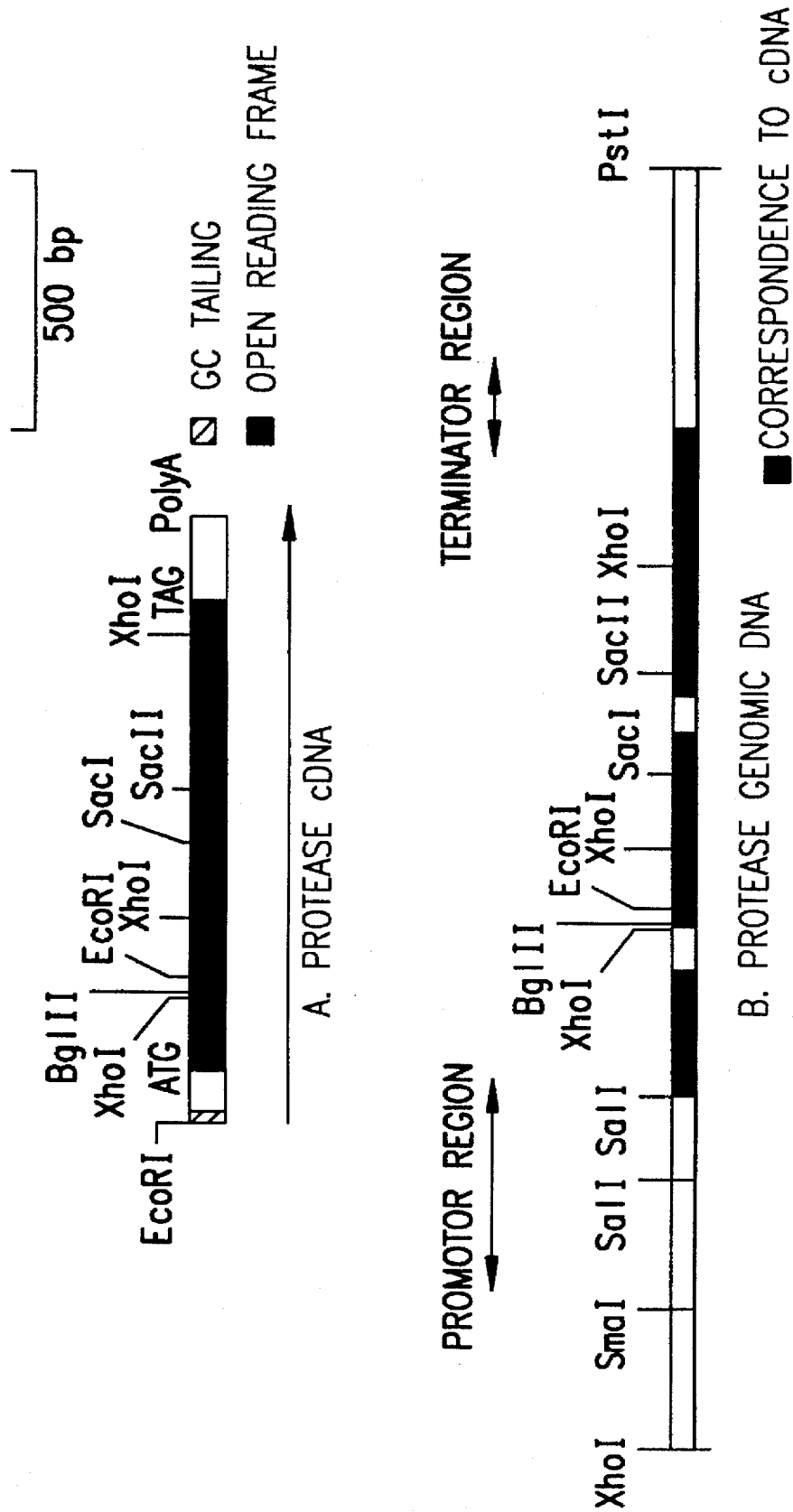

FIG. 1C shows the restriction enzyme cleavage map of the alkaline protease cDNA and that of the genomic alkaline protease DNA.

FIGS. 1D–1F show the nucleotide sequence of the genomic alkaline protease DNA (SEQ ID NO:1). M means G or C.

FIGS. 1G and 1H show the nucleotide sequnce of the alkaline protease cDNA (SEQ ID NO:2).

FIGS. 1I and 1J show the nucleotide sequence (SEQ ID NO:3) and deduced amino acid sequence (SEQ ID NO:4) in the fused region between the alkaline protease cDNA (λgt-Protease2) and the λgt11 β-galactosidase gene.

FIG. 1K shows the nucleotide sequence (SEQ ID NO:5) and deduced amino acid sequence (SEQ ID NO:6) of the open reading frame of the alkaline protease cDNA (λgt-Protease2).

Figure 1L:
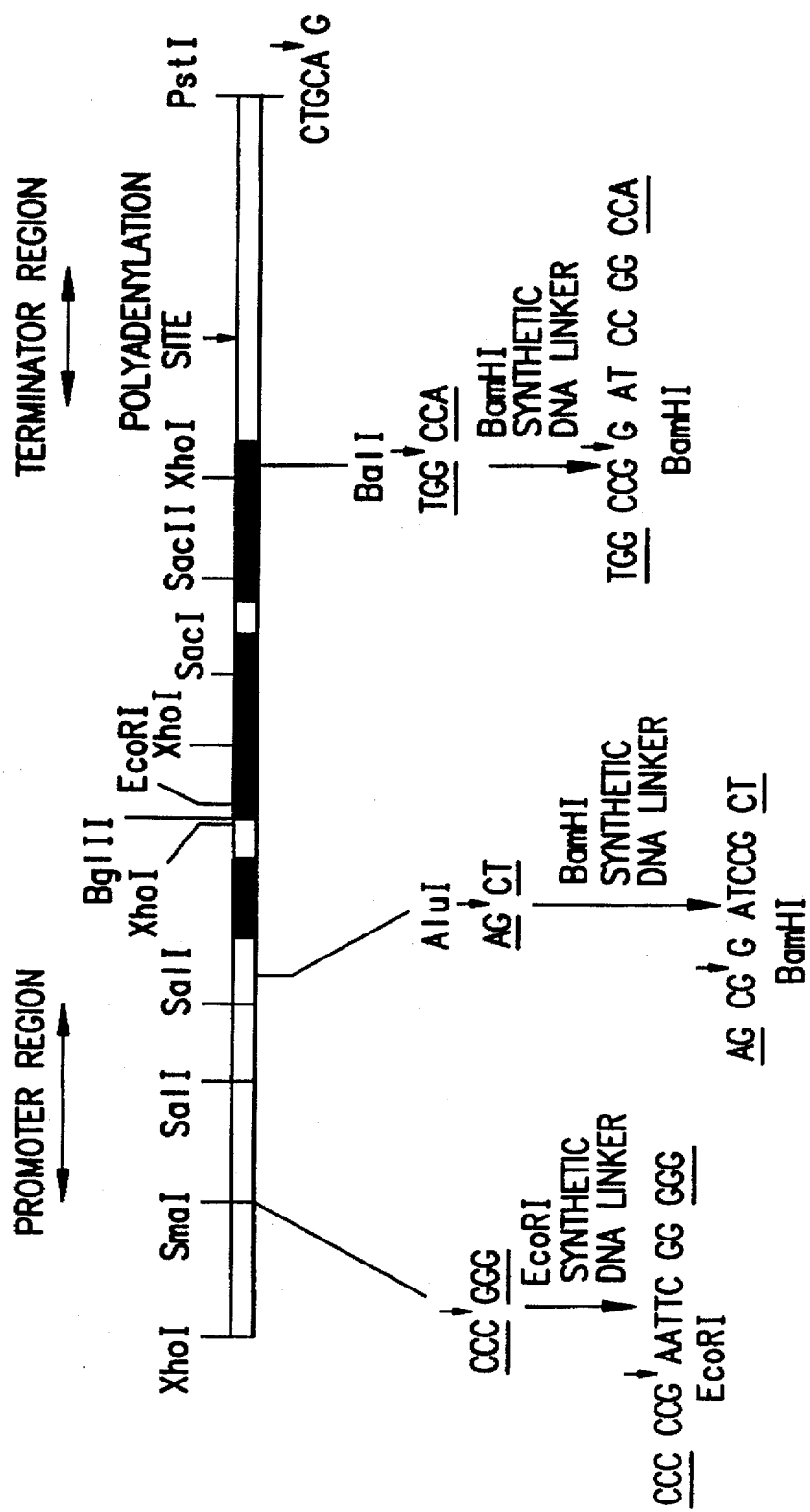
Figure 10:
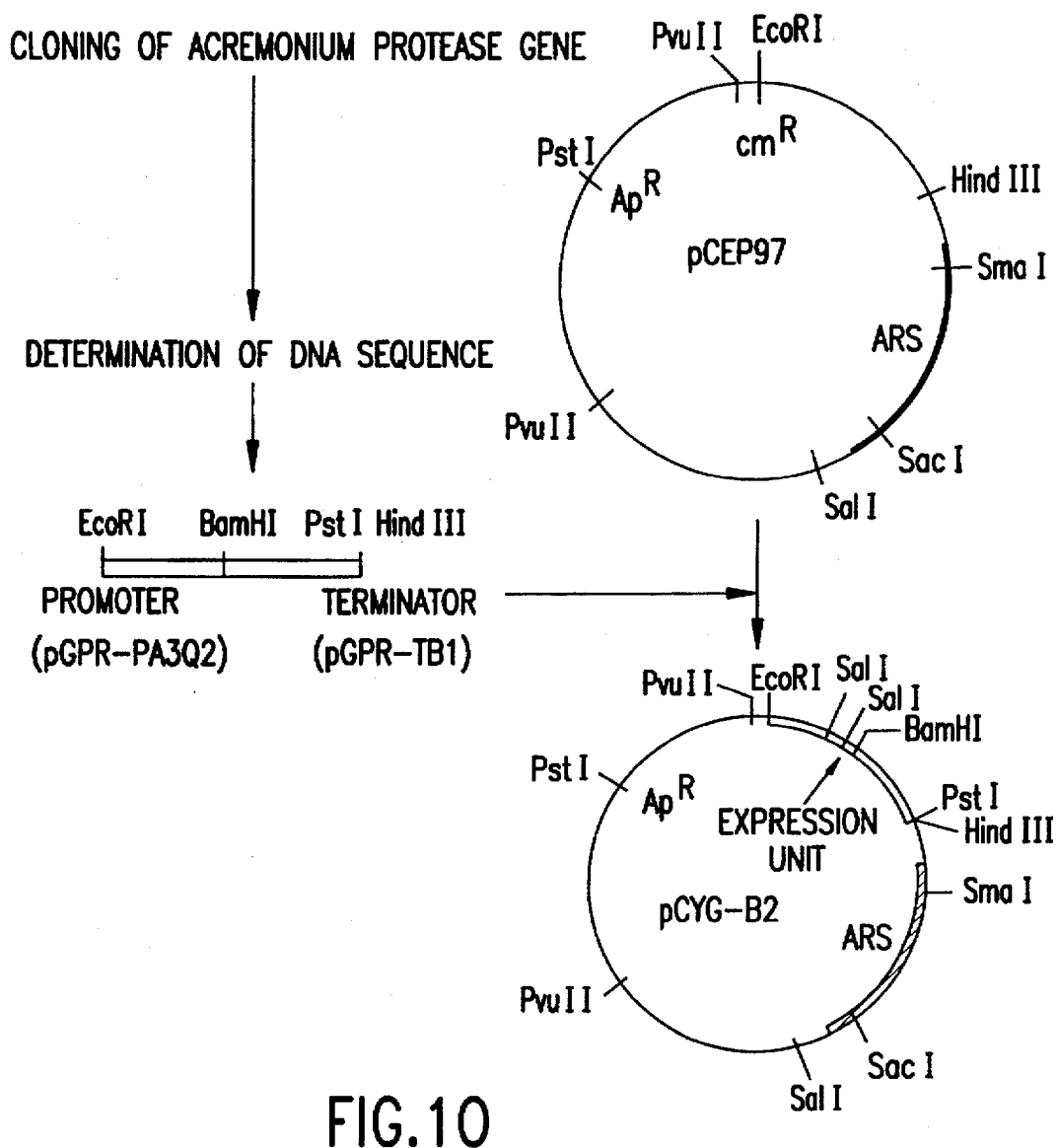

FIG. 1L shows the genomic alkaline protease gene and the site of addition of a synthetic linker (SEQ ID NOS:7–9).

FIG. 1M shows the nucleotide sequence (after modification with EcoRI and BamHI) in the vicinity of the promoter of the genomic alkaline protease DNA (SEQ ID NO:10).

FIG. 1N shows the nucleotide sequence (after modification with BamHI and HindIII) in the vicinity of the terminator of the genomic alkaline protease DNA (SEQ. ID NO:11).

FIG. 1O shows construction scheme for a plasmid, pCYG-B2.

Figure 1P:
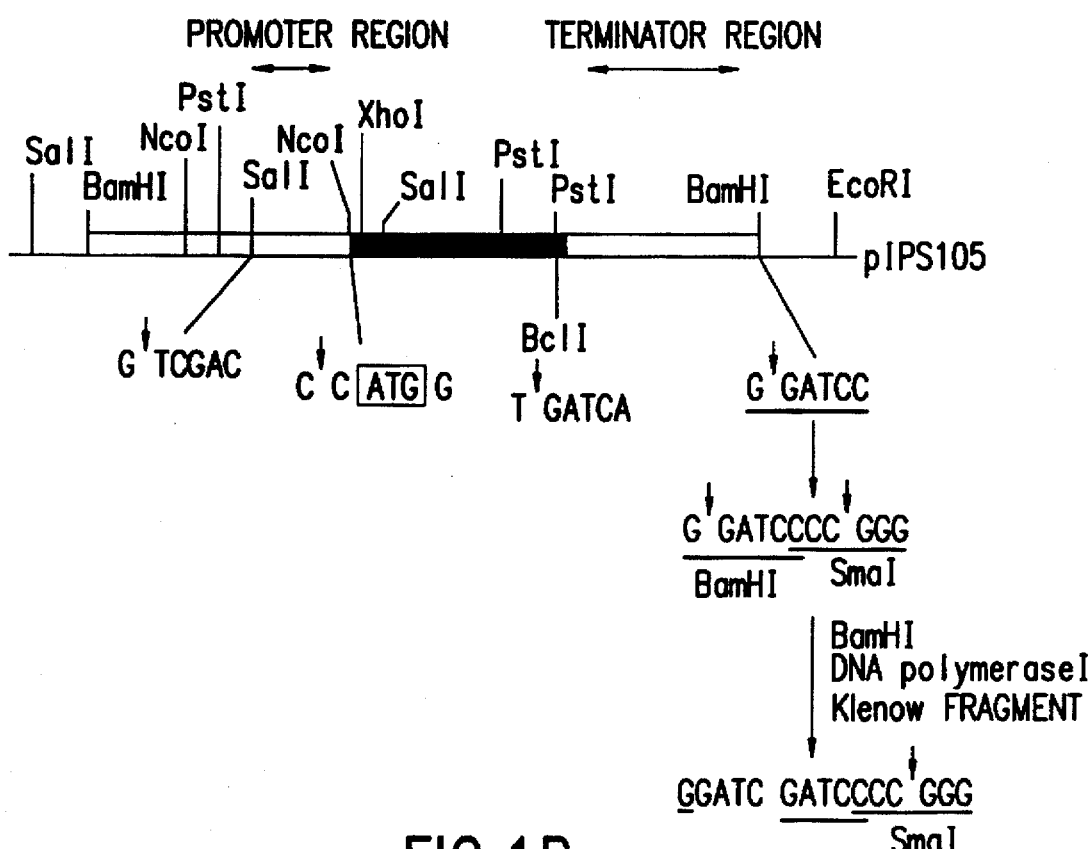

FIG. 1P shows the genomic isopenicillin N synthetase DNA and the modification scheme for a restriction enzyme cleavage site thereof (SEQ ID NOS:12–13).

FIG. 1Q shows the nucleotide sequence in the vicinity of the promoter of the genomic isopenicillin N synthetase DNA (SEQ ID NO:14).

Figure 1R:
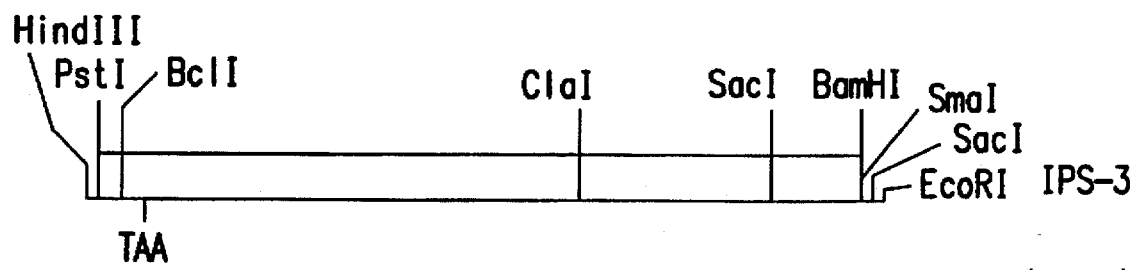

FIG. 1R shows the restriction enzyme cleavage map in the vicinity of the terminator of the genomic isopenicillin N synthetase DNA. For the restriction enzymes BglII, PvuII, SalI, SalII and XhoI, no cleavage site was found.

Figure 1S:
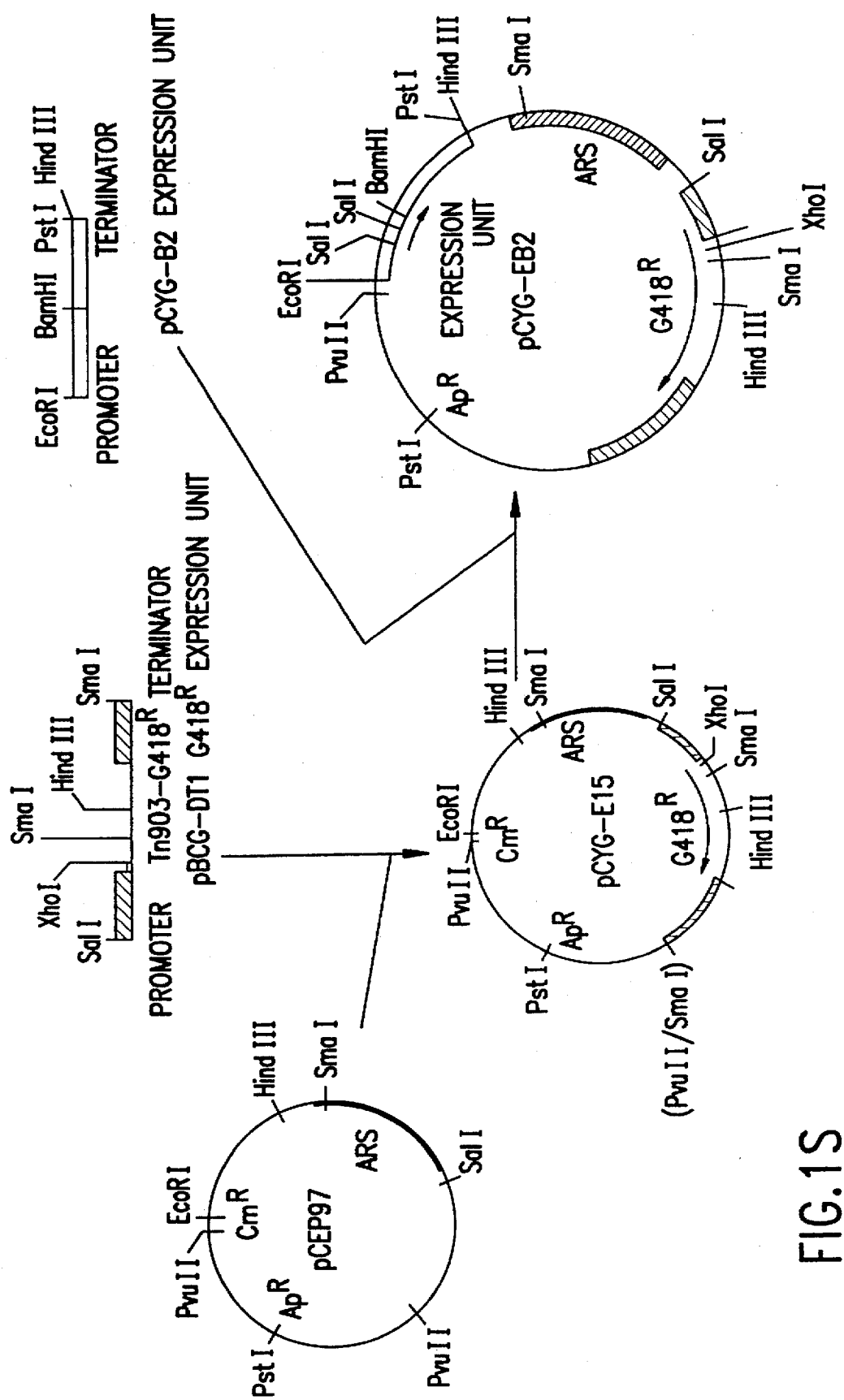

FIG. 1S shows the construction scheme for a plasmid, pCYG-EB2.

□: Promoter and terminator of the protease gene;

■: Promoter and terminator of the IPNS gene;

▫: A. chrysogenum-derived ARS;

—: pBR325 DNA and Tn903 DNA.

FIG. 1T shows the nucleotide sequence in the vicinity of the terminator of the genomic isopenicillin N synthetase DNA (SEQ ID NO:15).

Figure 2A:
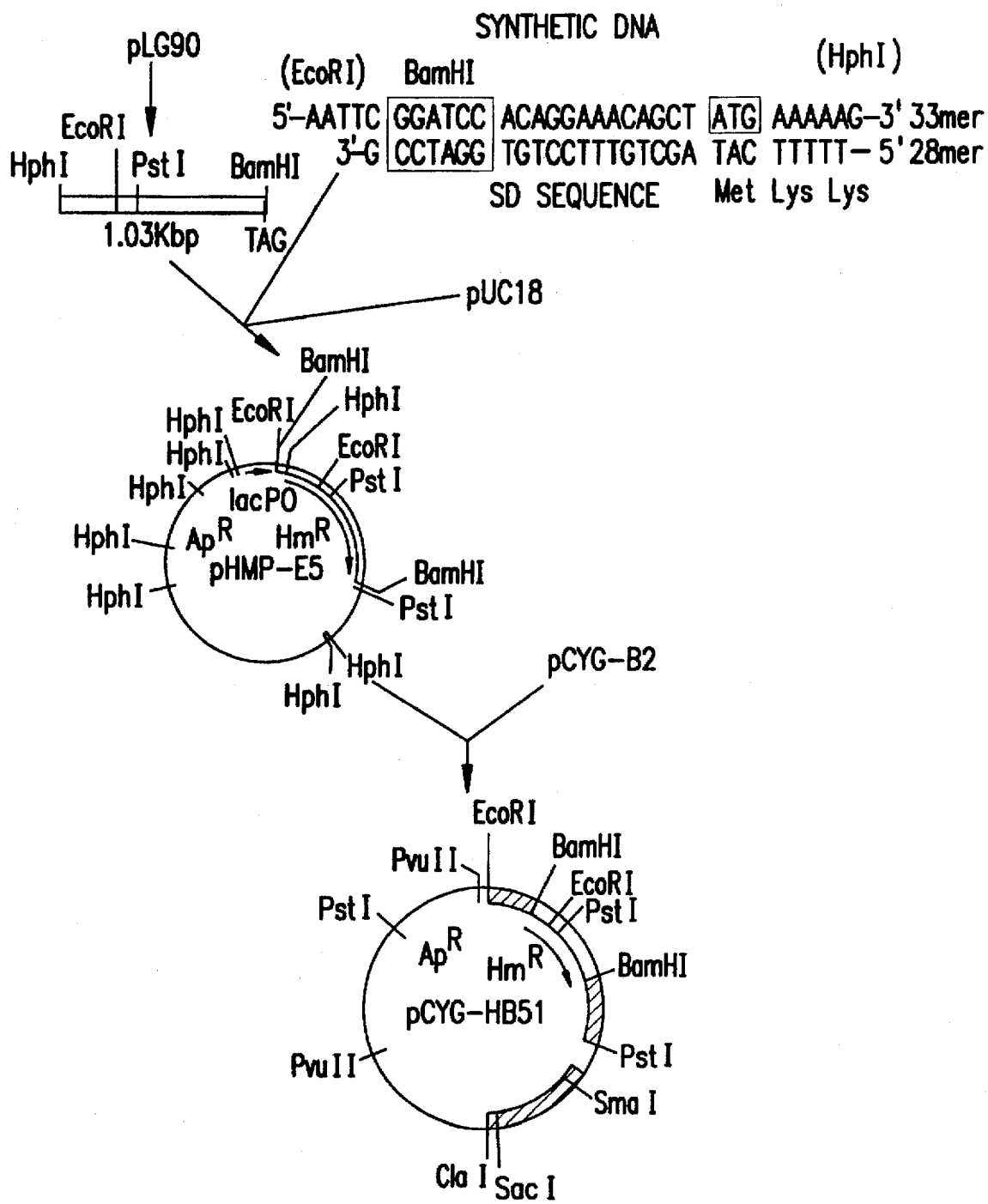

FIG. 2A shows the construction scheme for a plasmid, pYG-HB51 and SEQ ID NOS:16–17.

FIGS. 2B and 2C show the nucleotide sequence (SEQ ID NO:18) and deduced amino acid sequence (SEQ ID NO:19) of a hygromycin B resistance gene.

Figure 3A:
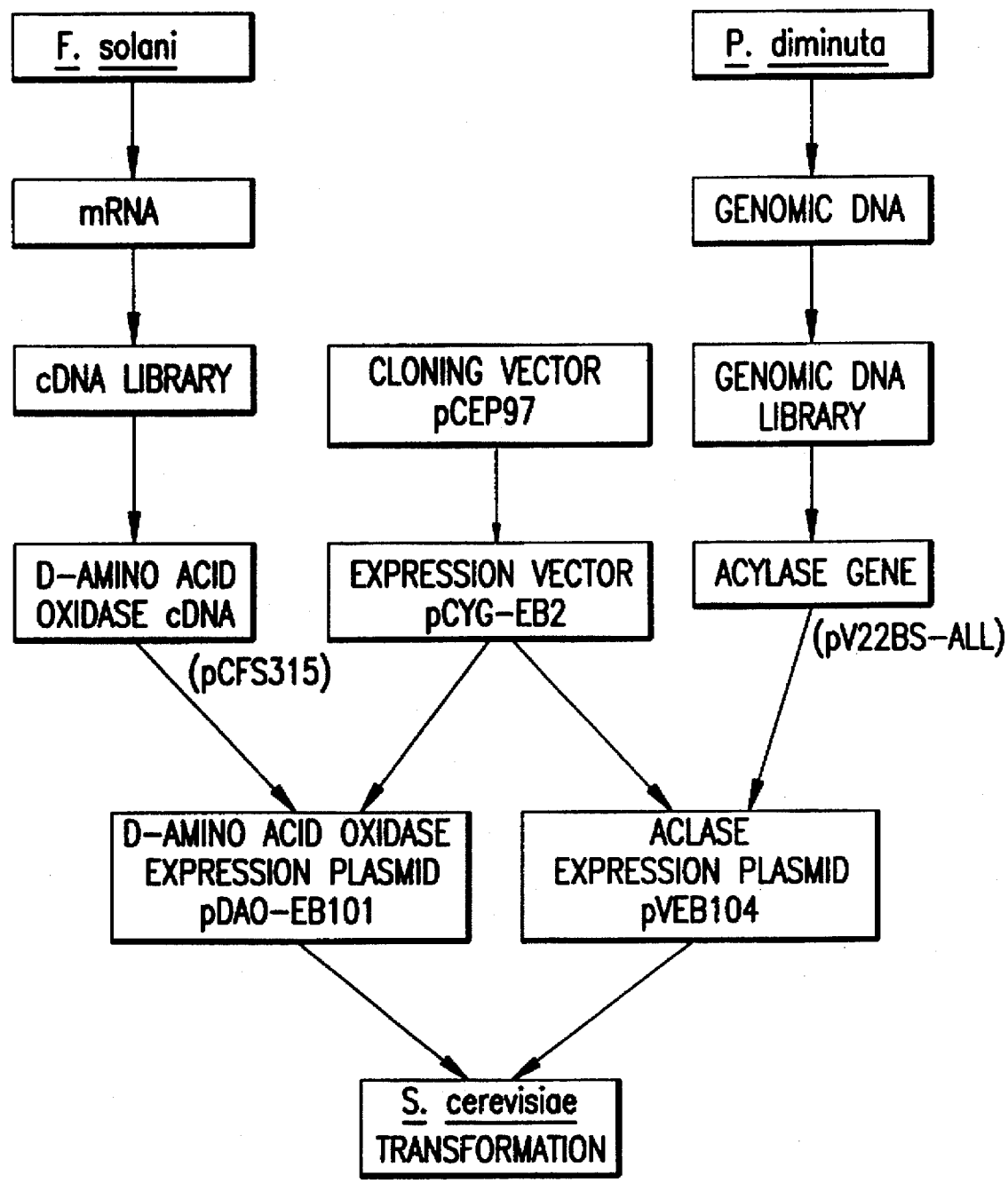

FIG. 3A schematically shows the procedure followed in Example 3.

Figure 3B:
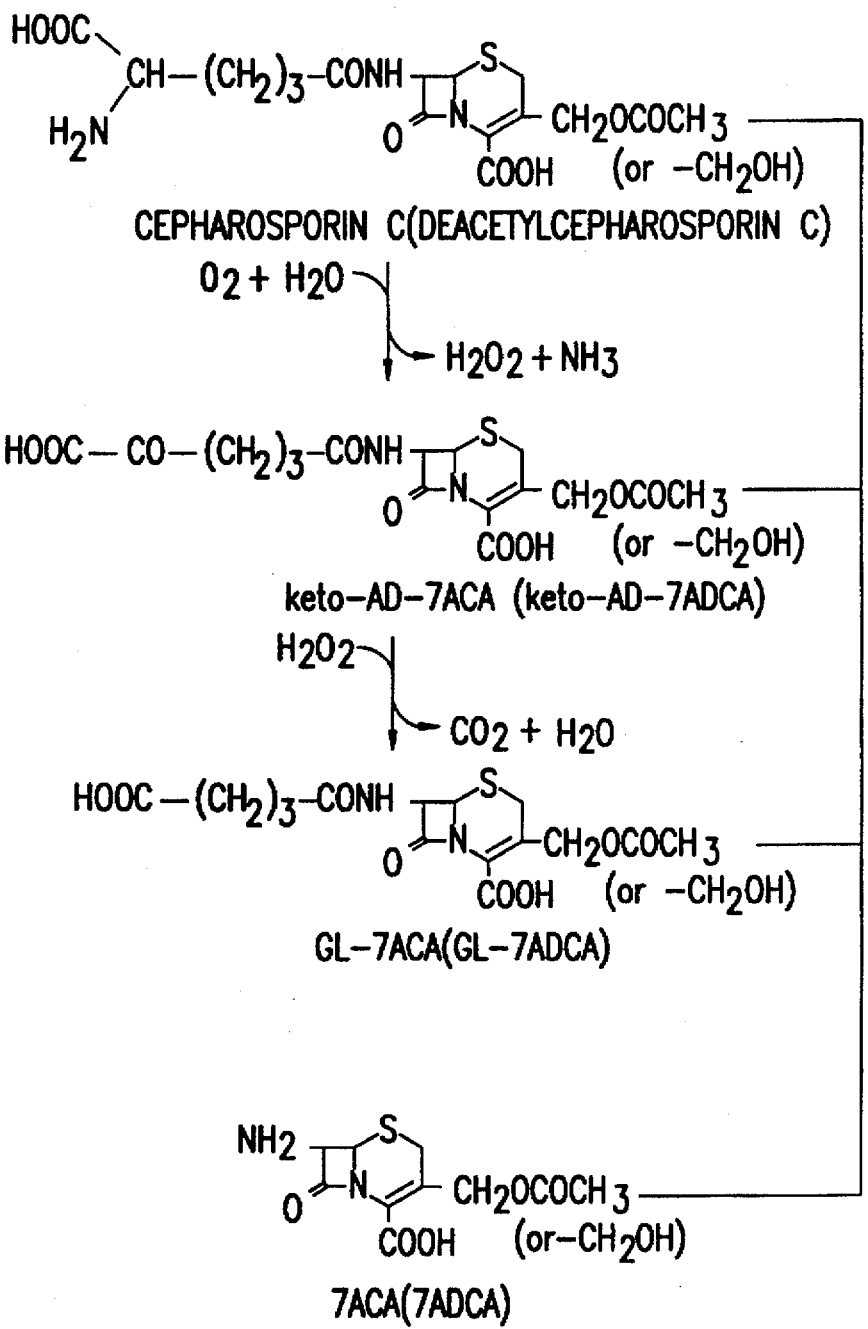

FIG. 3B shows the route of conversion of cephalosporin C and deacetylcephalosporin C to 7ACA and 7ADCA, respectively.

Figure 3C:
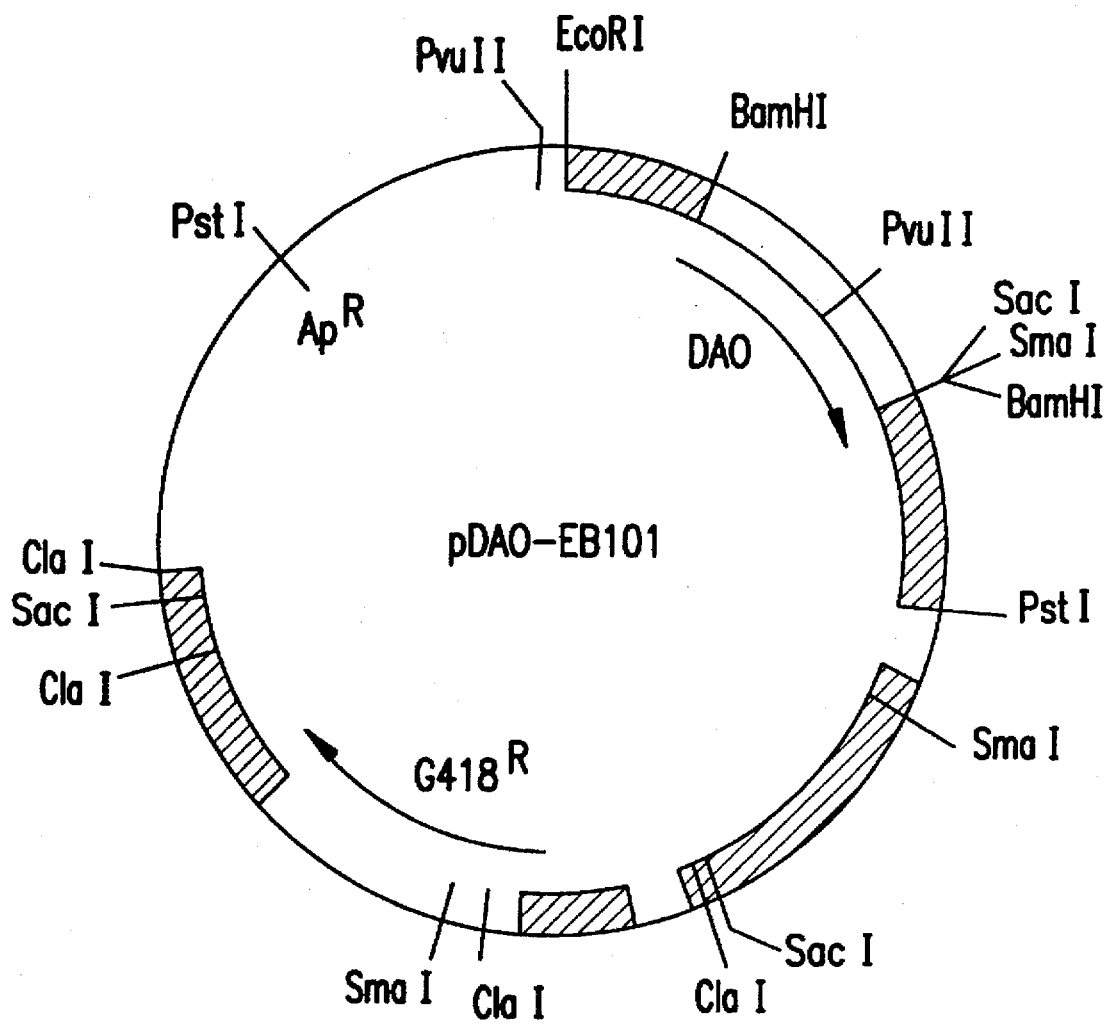

FIG. 3C shows the restriction enzyme cleavage map of a plasmid, pDAO-EB101.

Figure 3D:
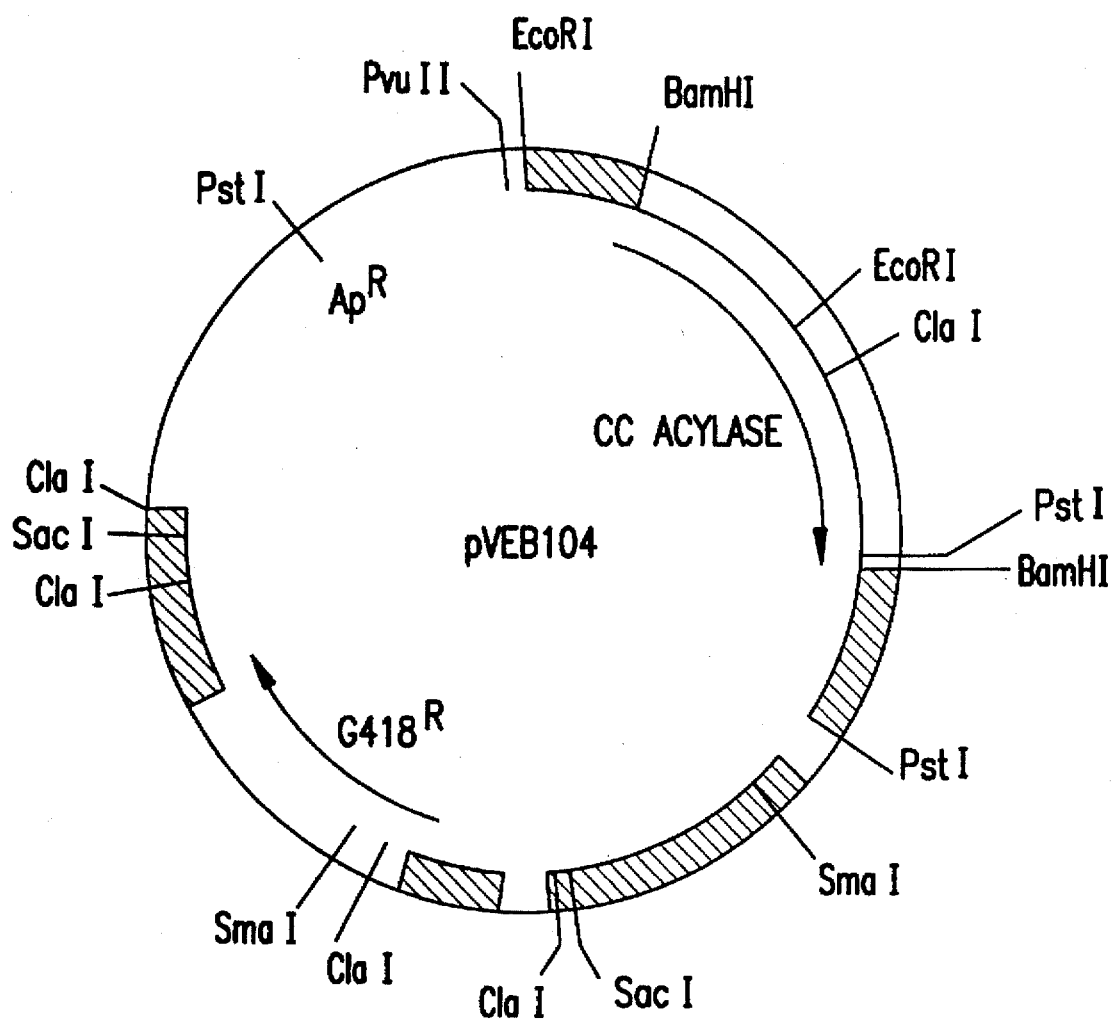

FIG. 3D shows the restriction enzyme cleavage map of a plasmid, pVEB104.

Figure 3E:
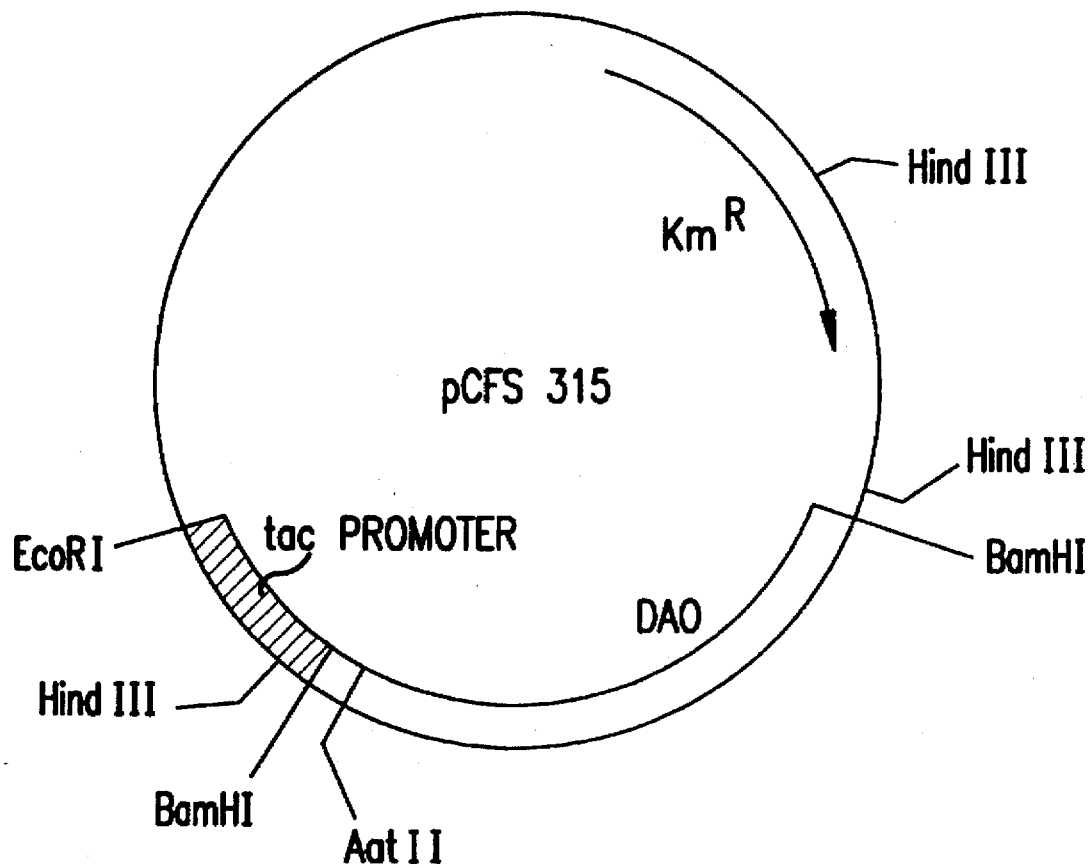

FIG. 3E shows the restriction enzyme cleavage map of a plasmid, pCFS315.

Figure 3F:
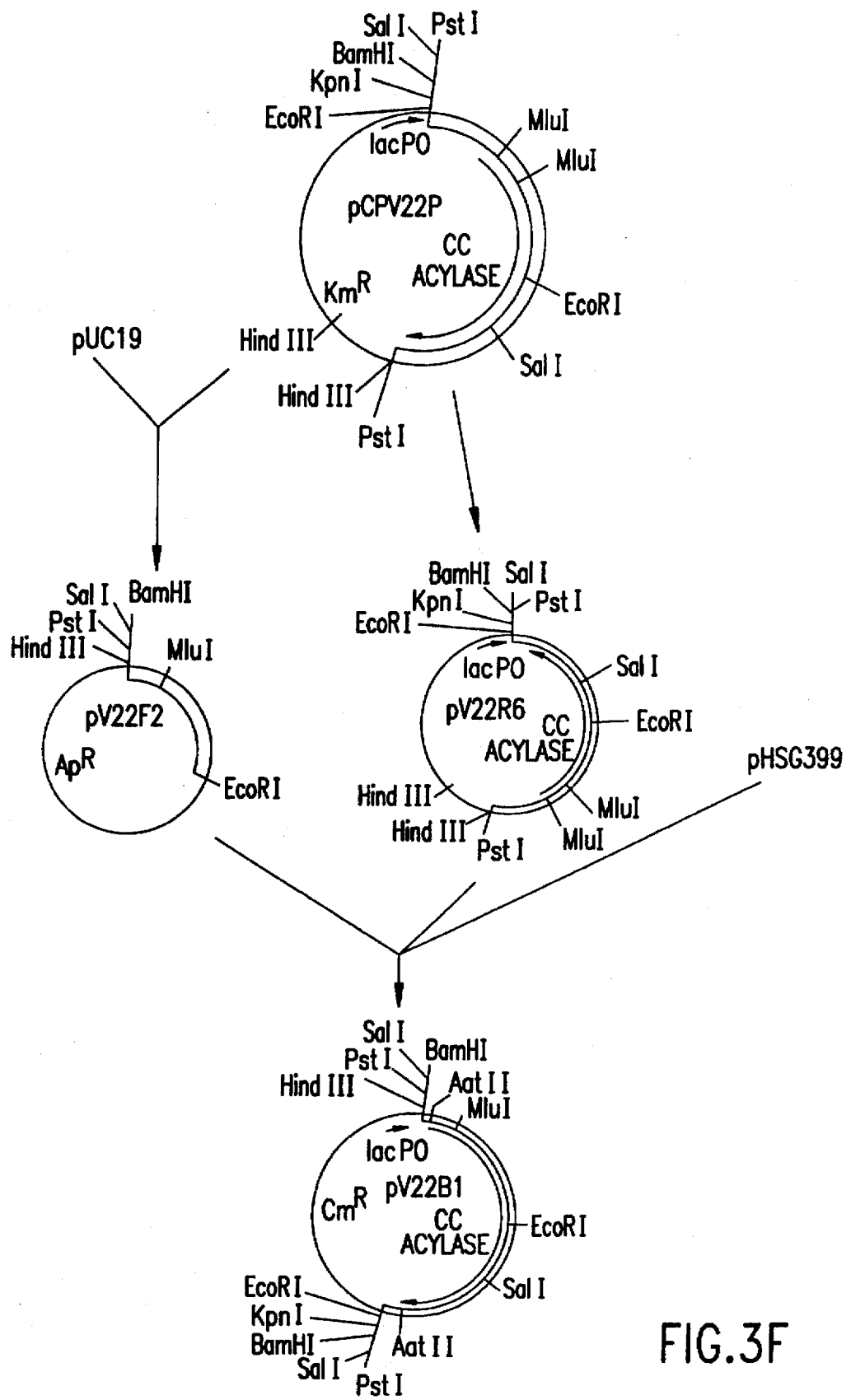

FIG. 3F shows the construction scheme for a plasmid, pV22B1.

FIGS. 3G and 3H show the nucleotide sequence (SEQ ID NO:20) and deduced amino acid sequence (SEQ ID NO:21) of the open reading frame of the Pseudomonas diminuta V22-derived cephalosporin C acylase gene.

Figure 3I:
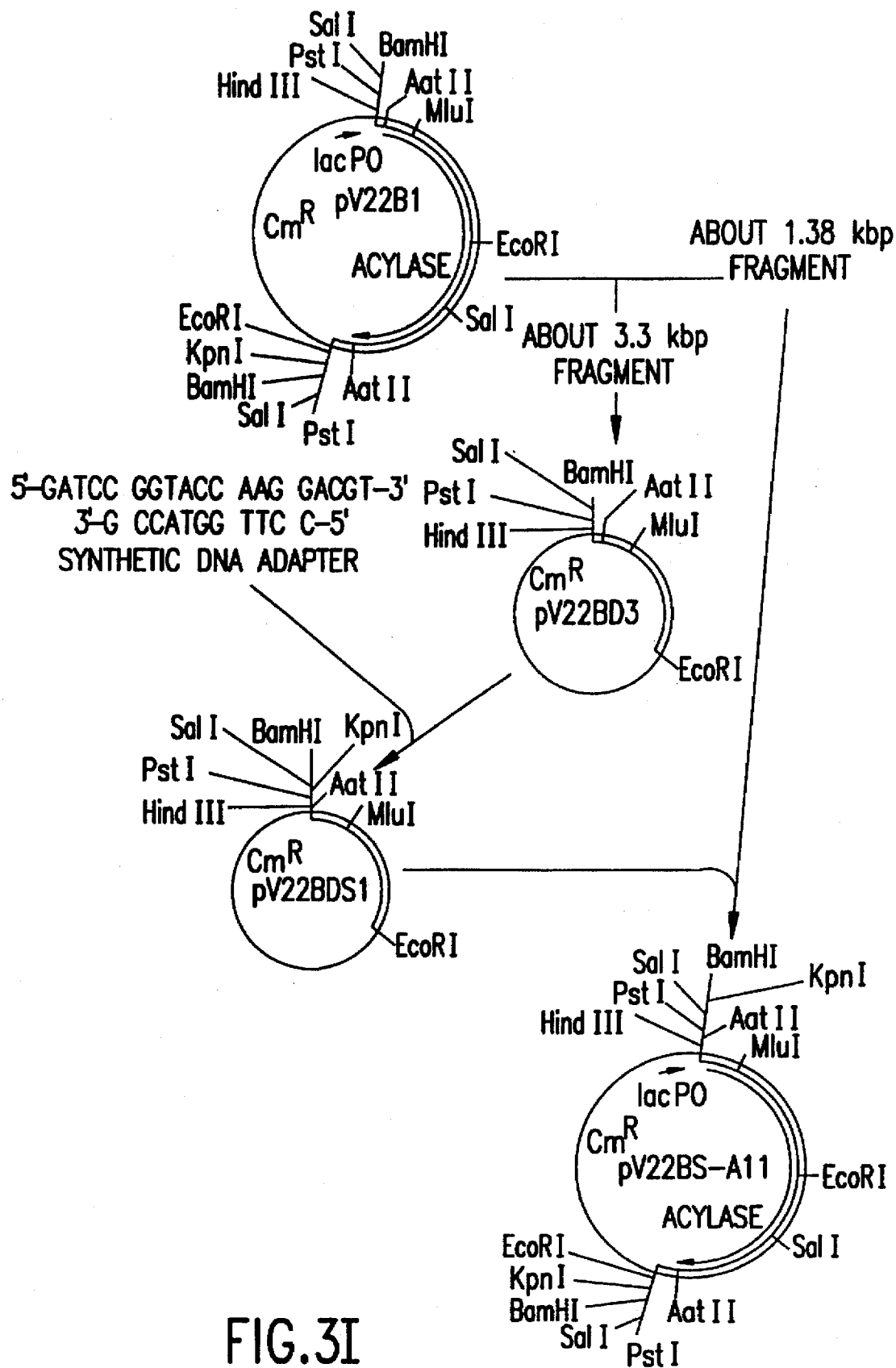

FIG. 3I shows the construction scheme for a plasmid, pV22BS-A11.

FIG. 3J shows the modification scheme for a site upstream from the acylase ATG codon of the plasmid pV22B1 (SEQ ID NOS:22–23).

Figure 3K:
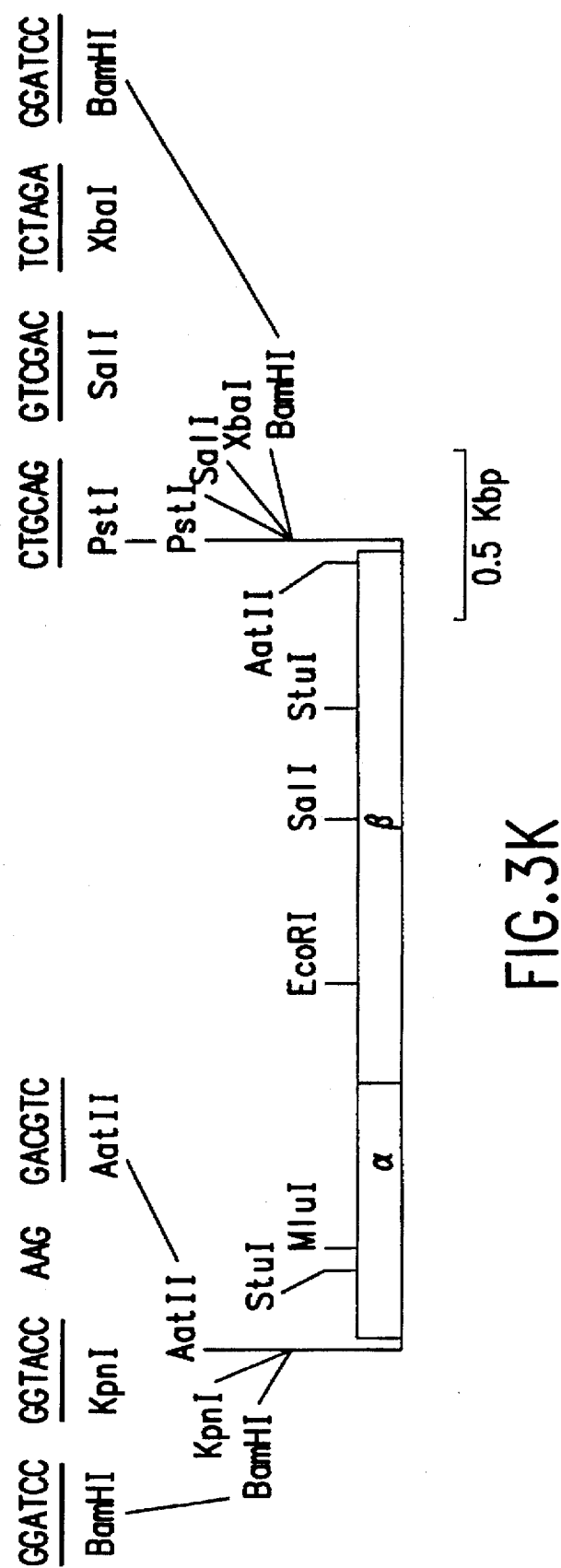

FIG. 3K shows the restriction enzyme cleavage map in the vicinity of the cephalosporin C acylase gene in the plasmid pV22BS-All. In the figure, α and β indicate the estimable α-subunit and β-subunit, respectively.

FIGS. 3L and 3M show the nucleotide sequence (SEQ ID NO:24) and deduced amino acid sequence (SEQ ID NO:25) of the coding region of the DAO gene contained in the plasmid pCFS315.

Figure 4A:
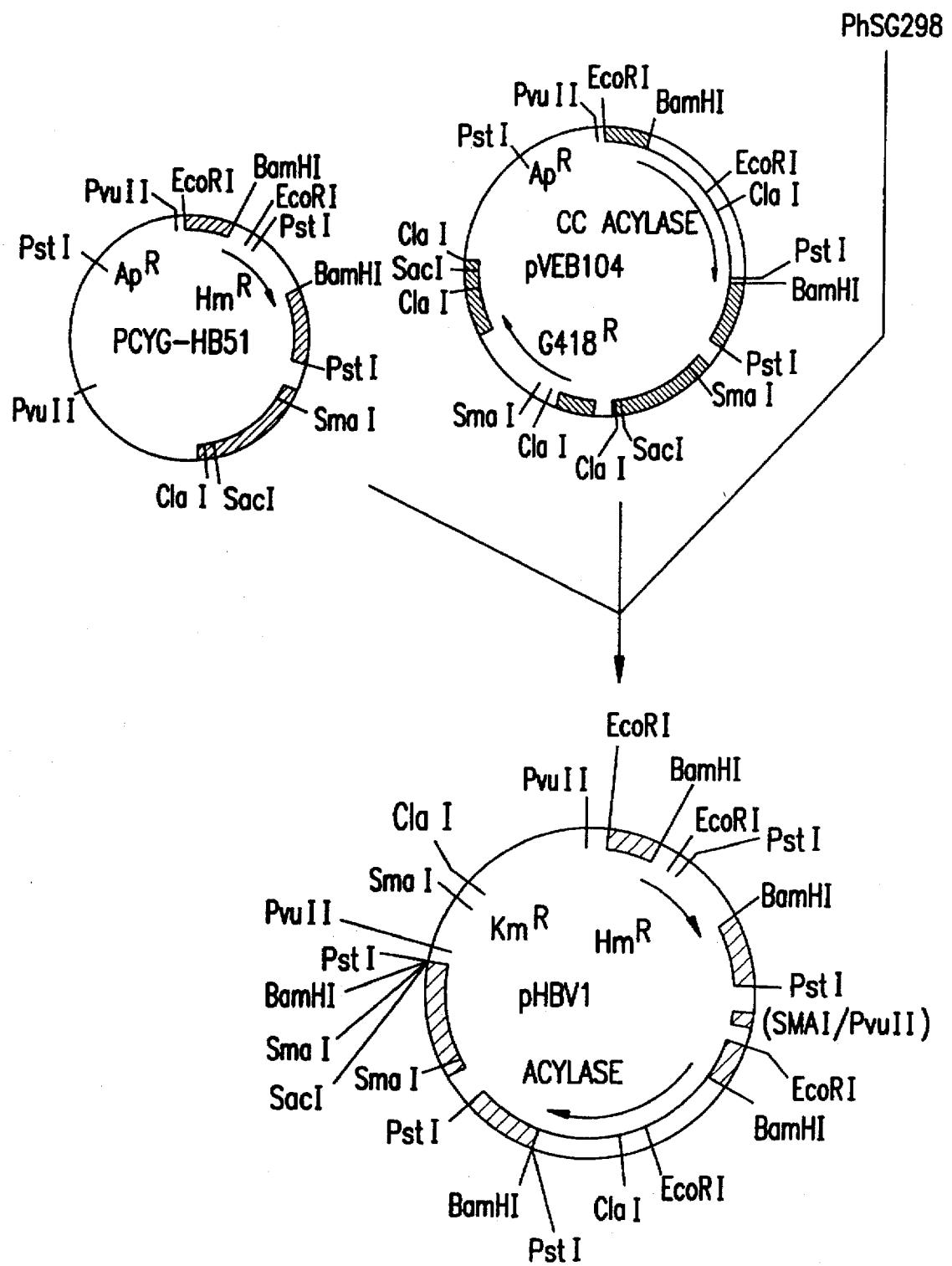

FIG. 4A shows the construction scheme for a vector for 3ACA production, pHBV1.

Figure 4B:
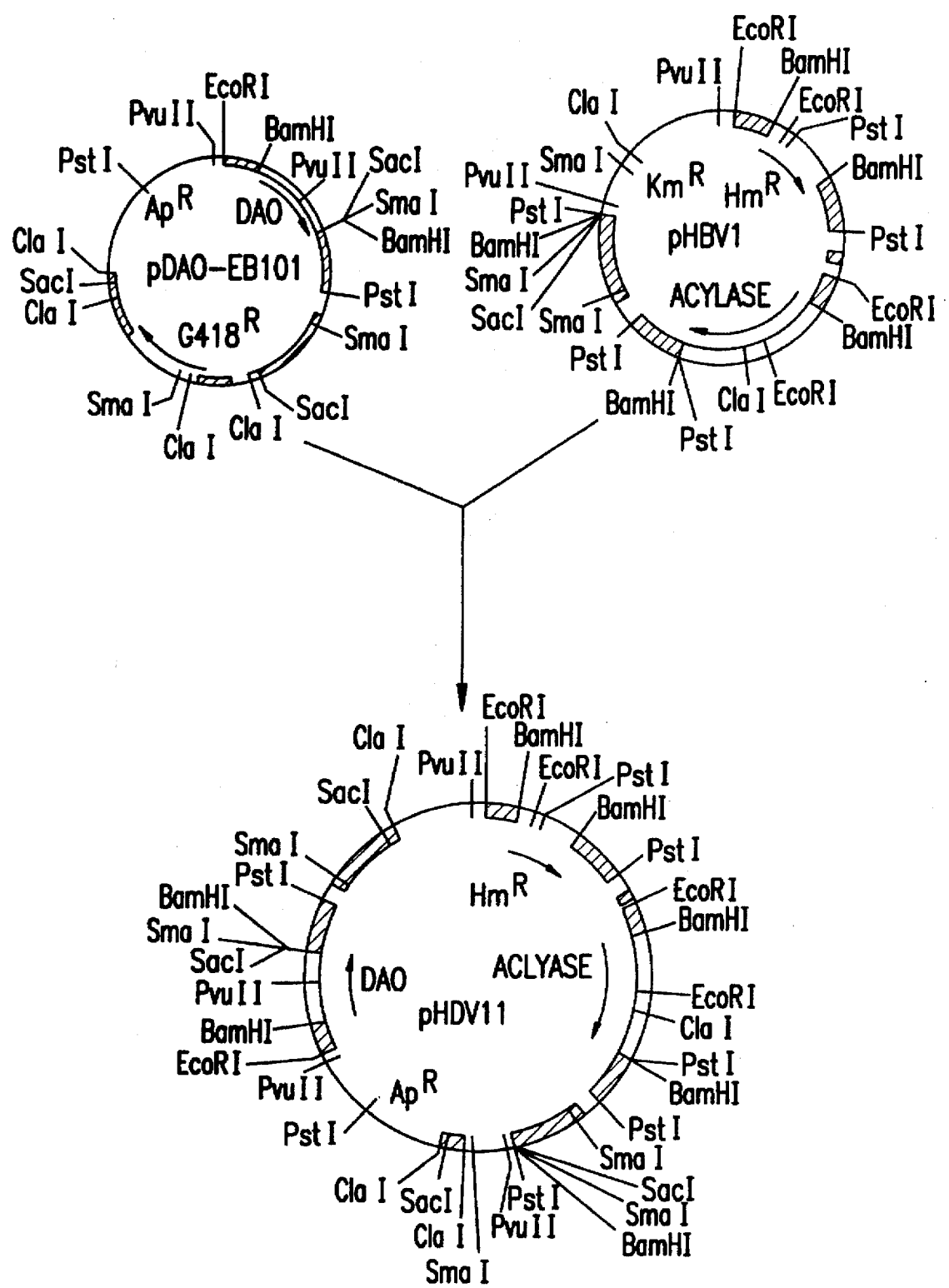

FIG. 4B shows the construction scheme for a vector for 7ACA production, pHDV11.

Figure 4C:
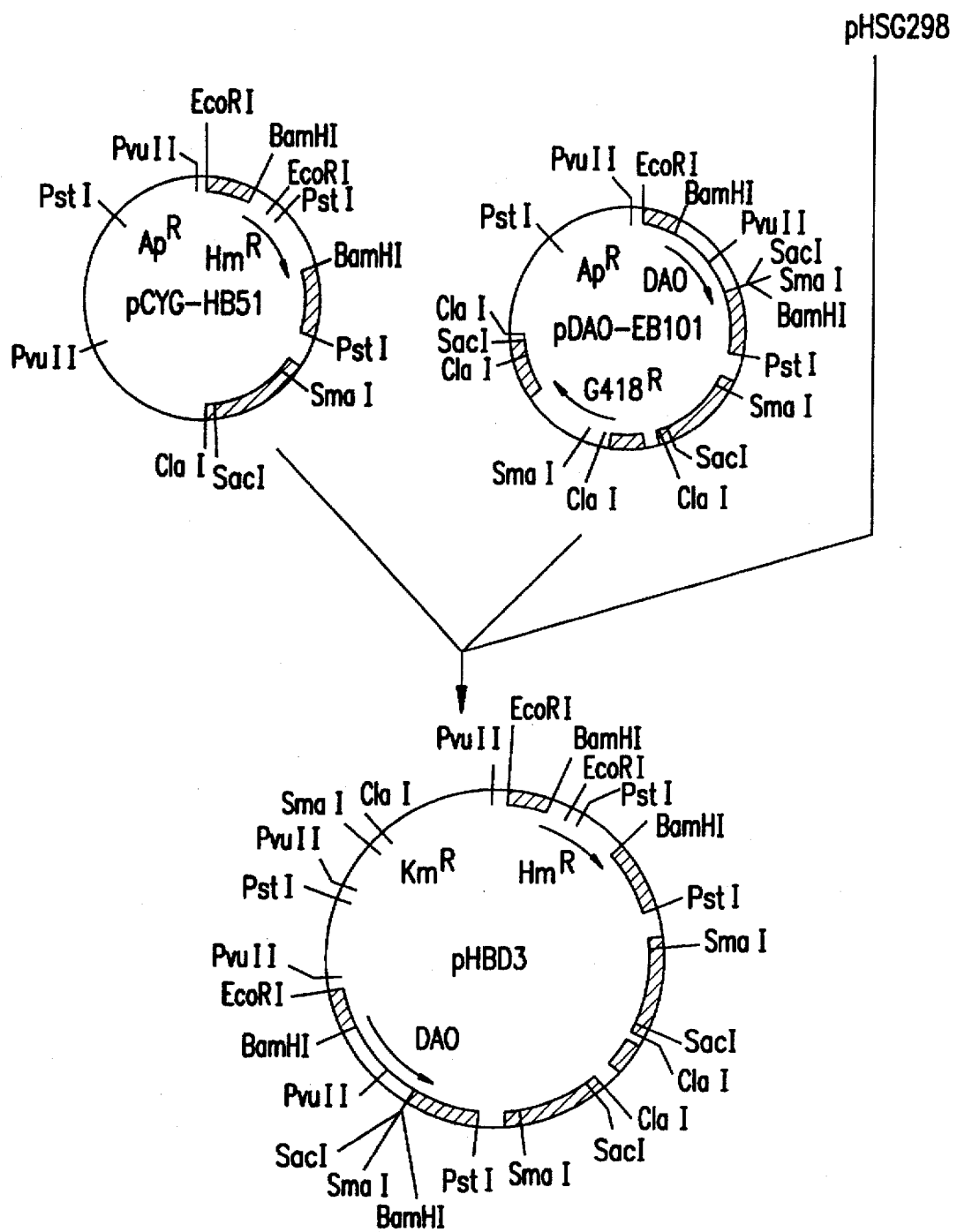

FIG. 4C shows the construction scheme for a vector for GL-7ACA production, pHBD3.

DETAILED DESCRIPTION OF THE INVENTION

The vector for producing 7-aminocephem compound (I) in accordance with this invention contains a DNA fragment prepared by ligating at least one or more promoter(s) for Acremonium chrysogenum (when the host cells are cells of Acremonium chrysogenum, for instance) to gene(s) for enzyme(s) capable of converting the cephalosporin compound (II) to the corresponding 7-aminocephem compound (I) to each other in that order from the upstream side to the downstream side by a conventional method. A5 appropriate selective marker, autonomously replicating sequence (ARS) for Acremonium chrysogenum, terminator, translation activating sequence and so forth may be inserted into said vector at respective desired sites by a conventional method. It is convenient for vector amplification in Escherichia coli if the autonomously replicating sequence for Escherichia coli (ori) and a selective marker are inserted in the vector.

Such vector may be constructed, for example by the methods described later herein in the examples or modifications thereof.

The "promoter for Acremonium chrysogenum" means a promoter capable of enabling expression, in Acremonium chrysogenum, of the gene coding for a desired polypeptide and includes those hitherto known, such as the promoter for the Acremonium chrysogenum isopenicillin synthetase gene and the promoter for the Acremonium chrysogenum β-isopropyl malate dehydrogenase gene, as well as the DNA fragment having promoter activity for alkaline protease gene which was newly isolated from the Acremonium chrysogenum chromosome by the present inventors. These promoters may contain an enhancer sequence.

As the gene for an enzyme capable of converting cephalosporin compound (II) to 7-aminocephem compound (I) may include cephalosporin C acylase gents which are genes for enzymes catalyzing one-step conversion [e.g. Pseudomonas sp. SE83-derived cephalosporin C acylase gene [cf. A. Matsuda et al., J. Bacteriol., 169, 5815–5826 (1987)] as well as the cephalosporin C acylase gene newly isolated from Pseudomonas diminuta V22 by the present inventors]. As the gene(s) for enzyme(s) catalyzing two-step conversion, there may be mentioned the combination of a D-amino acid oxidase (hereinafter, "DAO") gene and a GL-7ACA-acylase gene and the combination of a cephalosporin C acylase gene and a DAO gene (cephalosporin C acylases in general being also capable of converting GL-7ACA and GL-7ADCA, and keto-AD-7ACA and keto-AD-7ADCA, to 7ACA and 7ADCA, respectively). In cases where the cephalosporin compound (II) producer used as the host produces GL-7ACA, GL-7ADCA, keto-AD-7ACA and/or keto-AD-7ADCA, a cephalosporin C acylase gene or a GL-7ACA acylase gene may be used alone.

As the D-amino acid oxidase gene, there may be mentioned, for example, the Trigonopsis variabilis-derived DAO gene (cf. Japanese Kokai Tokkyo Koho No. 62-262994) and the DAO gene newly isolated from Fusarium solani M-0718. FERM-P 2688 by the present inventors (cf. European Laid-open Patent Publication No. 364,275).

As the GL-7ACA acylase gene, there may be mentioned, for example, the gene for the *Pseudomonas putida* ATCC 950-derived GL-7ACA acylase [cf. Agric. Biol. Chem., 45, 1561 (1981)] as well as the cephalosporin C acylase genes specifically mentioned above (cephalosporin C acylases serving also as GL-7ACA acylases).

The enzyme gene(s) is preferably inserted each singly into the vector at a site downstream from the promoter for *Acremonium chrysogenum*. The vector for producing 7-aminocephem compound (I) in accordance with the invention may contain one or more genes for an enzyme or enzymes capable of converting the cephalosporin compound (II) to the 7-aminocephem compound as inserted therein.

The selective marker my be any marker utilizable in screening transformants following transformation of *Acremonium chrysogenum* with the vector. The marker ($Hm^R$) which provides the hygromycin resistance phenotype, for instance, is widely used.

The autonomously replicating sequence (ARS) for *Acremonium chrysogenum* is, for example, the ARS of *Acremonium chrysogenum* (cf. Japanese Kokai Tokkyo Koho No. 61-209593). Since, however, transformation of *Acremonium chrysogenum* with the vector for 7-aminocephem compound production mainly results in incorporation of said vector into the genomic DNA of *Acremonium chrysogenum* and the subsequent replication, it is not necessary, in such a case, that the vector for 7-aminocephem compound production should contain an ARS insert. The presence of an. ARS is required only when the vector for 7-aminocephem compound production is multiplied as an extrachromosomal component in *Acremonium chrysogenum*. The terminator, which may contain a polyadenylation site, is, for example, the *Acremonium chrysogenum* genomic DNA-derived terminator used in the examples to be mentioned later herein.

Cephalosporin compound (II)-producing strains belonging to the species *Acremonium chrysogenum* may be transformed with the vector for 7-aminocephem compound production by a conventional method, for example by the protoplast transformation method [cf. S. W. Queener et al.: Microbiology 1985, American Society of Microbiology, page 468 (1985)].

The cephalosporin compound (II) producer includes, among others, *A. chrysogenum* ATCC 11550, ATCC 36225, etc. as cephalosporin C producers, *A. chrysogenum* ATCC 20371 etc. as deacetylcephalosporin C producers, *A. chrysogenum* ATCC 11550, ATCC 20416, etc. as deacetoxycephalosporin C producers and *A. chrysogenum* ATCC 20416, ATCC 20427, etc. as GL-7ACA and keto-AD-7ACA producers. A number of microorganisms other than *Acremonium chrysogenum* are also known to be cephalosporin compound (II) producers. It is also possible to prepare 7-aminocephem compound producers by using such microorganisms as host cells and transform them with an appropriate vector for 7-aminocephem compound production by a method conventional in the field of genetic engineering referring to the above-mentioned method, for instance.

The thus-obtained 7-aminocephem compound (I)-producing microorganism [cephalosporin compound (II) producer microorganism transformed with the vector for the production of 7-aminocephem compound] is cultivated in a nutrient medium. In principle, this cultivation can be carried out in the same manner as in cultivating microorganisms in general. Generally, however, submerged culture using an aqueous medium is advantageous. The medium to be used in the cultivation may be a synthetic one, a semisynthetic one or a natural one. As the carbon source to be included in the medium composition, there may be mentioned, for example, glucose, sucrose, maltose, glycerin, starch, liquefied starch and the like. As the nitrogen source there may be mentioned, for example, meat extract, caseine hydrolyzate, peptone, gluten meal, corn meal, cottonseed flour, soybean meal, corn steep liquor, dried yeast, yeast extract, urea, ammonium phosphate and the like. Inorganic salts, such as disodium hydrogen phosphate, potassium dihydrogen phosphate, magnesium chloride, magnesium sulfate and calcium carbonate, may be added to the medium, if desired.

In case the medium foams severely during cultivation, an antifoam such as a vegetable oil (e.g. soybean oil or castor oil), a higher alcohol (e.g. octadecanol, tetradecanol or heptanol), or a silicone compound, may be added in an appropriate amount.

The cultivation is suitably carried out at a temperature of about 30° C. When the culture volume is large, the employment of appropriate seed culture will give good results in many instances. The period of the cultivation is suitable about 100 to 170 hours and may be prolonged when a high concentration medium is used.

The cultivation conditions mentioned above may be modified depending on the characteristics of the producing strain employed so that optimum conditions can be seleced and applied.

The 7-aminocephem compound (I) formed during cultivation is generally accumulated extracellularly in the culture in most cases. Therefore the desired 7-aminocephem compound (I) can generally be isolated and purified from the filtrate (or supernatant) separated from microbial cells by centrifugation, filtration or the like means, by applying to the filtrate (supernatant) combinedly (in an appropriate order) and/or repeatedly such means as concentration under reduced pressure, solvent extraction, pH adjustment, treatment with a resin (e.g. anion exchange resin, cation exchange resin, nonionic adsorbent resin, etc.), treatment with an adsorbent (e.g. activated carbon, silicic acid, silica gel, alumina, cellulose, etc.), high-performance liquid chromatography, crystallization, recrystallization, and the like means used in producing antibiotic substances in general.

The 7-aminocephem compound (I) obtained in the free form can be converted to desired salts by reacting it with a base such as sodium hydroxide and the like.

The following examples are further illustrative of this invention. In the examples, the following abbreviations are used.

DNA: Deoxyribonucleic acid c-DNA: Complementary DNA

RF DNA: Replicative form DNA

RNA: Ribonucleic acid m-RNA: Messenger RNA dNTP: Mixture of dATP (deoxyadenosine triphosphate),
 dCTP (deoxycytidine triphosphate),
 dGTP (deoxyguanosine triphosphate) and
 dTTP (deoxythymidine triphosphate)

bp: Base pairs

Kbp: Kilo base pairs $Ap^R$: Ampicillin resistance in *E. coli*

$Ap^S$: Ampicillin sensitivity in *E. coli*

$Cm^R$: Chloramphenicol resistance in *E. coli*

$Cm^S$: Chloramphenicol sensitivity in *E. coli*

$Km^R$: Kanamycin resistance in *E. coli*

$Km^S$: Kanamycin sensitivity in *E. coli*

$Tc^R$: Tetracycline resistance in *E. coli*
$Tc^S$: Tetracycline sensitivity in *E. coli*
lac PO: Lactose operon promoter and operator in *E. coli*
tac PO: Trp-lac promoter and operator in *E. coli*
$Acy^+$: Acylase activity
$Hm^R$: Hygromycin B resistance
$G418^R$: Resistance to the antibiotic G418
DAO: D-Amino acid oxidase
IPNS: Isopenicillin N synthetase
CC: Cephalosporin C
CCNa: Cephalosporin C sodium
DCC: Deacetylcephalosporin C
7ACA: 7-Amino-3-acetoxymethyl-3-cephem-4-carboxylic acid
7-Amino-3-hydroxymethyl-3-cephem-4-carboxylic acid
Keto-AD-7ACA: Ketoadipyl-7ACA [7-(5-carboxy-5-oxopentanamido)-3-acetoxlmethyl-3-cephem-4-carboxylic acid]
Keto-AD-7ADCA: Ketoadipyl-7ADCA [7-(5-carboxy-5-oxopentanamido)-3-hydroxymethyl-3-cephem-4-carboxylic acid]
GL-7ACA: Glutaryl-7ACA [7-(4-carboxybutanamido)-3-acetoxymethyl-3-cephem-4-carboxylic acid]
GL-7ADCA: Glutaryl-7ADCA [7-(4-carboxybutanamido)-3-hydroxymethyl-3-cephem-4-carboxylic acid]
DTT: Dithiothreitol
Tris: Tris(hydroxmethyl)aminomethane
EDTA: Ethylenediaminetetraacetic acid
SDS: Sodium lauryl sulfate
PEG: Polyethylene glycol
IPTG: Isopropyl-β-D-thiogalactopyranoside
X-gal: 5-Bromo-4-chloro-3-indolyl β-galactoside
Met: Methionine
Thr: Threonine
Ala: Alanine
Gln: Glutamine
Gly: Glycine
Val: Valine
Pro: Proline
Ile: Isoleucine
Lys: Lysine
Asn: Asparagine
Glu: Glutamic acid
Phe: Phenylalanine
Leu: Leucine
Asp: Aspartic acid
Tyr: Tyrosine
Cys: Cysteine
Trp: Tryptophan
Ser: Serine
Arg: Arginine
His: Histidine The compositions of the main buffers and media used in the examples are as follows:

TE buffer: 20 mM Tris-HCl (pH 7.5),
    0.5 mM EDTA
LB agar: 10 g/liter Bacto-tryptone (DIFCO),
    5 g/liter yeast extract (DIFCO),
    5 g/liter NaCl,
    15 g/liter agar (DIPCO),
    pH 7.2
B3 agar: 10 g/liter D-Galactose,
    2 g/liter Bacto-tryptone (DIFCO),
    1 g/liter $MgSO_4 \cdot 7H_2O$,
    1.5 g/liter $KH_2PO_4$,
    1 g/liter $NaNO_3$,
    20 g/liter agar,
    (pH about 5.6 to 6.0)
YPS medium: 20 g/liter Sucrose,
    10 g/liter polypeptone (Daigo Nutritive Chemicals),
    5 G/liter powdered yeast extract (Daigo Nutritive Chemicals),
    1 G/liter $K_2HPO_4$,
    1 g/liter $MgSO_4 \cdot 7H_2O$,
    (pH 7.0)
CS1 medium: 25 g/liter Sucrose,
    10 g/liter glucose,
    30 g/liter soybean meal,
    10 g/liter corn steep liquor (CSL),
    adjusted to pH 7.0 with
    5 g/liter $CaCO_3$
Main culture medium:
    16 g/liter Peanut powder,
    40 g/liter CSL,
    8 g/liter wheat germ,
    16 g/liter gluten meal,
    8 g/liter $(NH_4)_2SO_4$,
    20 g/liter glucose,
    20 g/liter sucrose,
    adjusted to pH 7.0 with NaOH,
    10 g/liter $CaCO_3$,
    35 ml/liter methyl oleate
1M KP buffer (pH 7.5):
    1M KCl,
    25 mM
    10 mM $MgCl_2$,
    10 mM Tris-HCl (pH 7.5)
1M KP buffer (pH 5.8):
    Buffer prepared by adjusting 1M KP buffer (pH7.5) to pH 5.8 with HCl
0.8M NaP buffer:
    0.8M NaCl,
    25 mM $CaCl_2 \cdot 2H_2O$,
    10 mM $MgCl_2$,
    10 mM Tris-HCl (pH 7.5)
PDA-YE agar: 39 g/liter Potato dextrose agar medium (Nissui Pharmaceutical),
    5 g/liter agar,
    5 g/liter yeast extract
BRM agar medium:
    [A] 2 g $NaNO_3$,
    1 g $KH_2PO_4$,
    274 g sucrose (final concentration 0.8M),
    10 g brain-heart infusion (DIFCO),
    7.5 g agar (Hayashi Junyaku),
    (pH about 6.3 to 6.4)
    [B] 20 g glucose (final concentration 2%),
    1.5 g $CaCl_2 \cdot 2H_2O$ (final concentration 10 mM)
An aqueous solution (900 ml) of components [A] and an aqueous solution (100 ml) of components [B] are respectively sterilized by autoclaving and then mixed up, and the mixture is used for preparing plates and so on.

Unless otherwise specified, the gene manipulation techniques used in the examples are those described in T. Maniatis et al.: Molecular Cloning—A Laboratory Manual, published 1982 by Cold Spring Harbor Laboratory.

EXAMPLE 1

The whole procedure followed in this example is outlined in FIG. 1A.

(1) Cloning of an alkaline protease cDNA and chromosomal DNA (1-i) Purification of alkaline protease derived from *A. chrysogenum* ATCC 11550 and antibody preparation:

Following the method of Yagi et al. [J. Yagi et al., J. Ferment. Technol., 50, 5.92 (1972)], *A. chrysogenum* ATCC 11550 was cultivated and alkaline protease was recovered from the culture filtrate by precipitation with 70% saturated ammonium sulfate, followed by purification using CM (carboxymethyl)-cellulose and Sephadex G75. A molecular size of about 30,000 dalton was revealed by analysis by 11% SDS-PAGE (SDS polyacrylamide gel electrophoresis). This alkaline protease was mixed with complete Freund adjuvant (DIFCO) and the mixture was injected into male New Zealand white rabbits three times at a dose of 2 mg per injection in order to cause antibody production. Then whole blood collection and serum separation were made, and the serum was treated at 56° C. for 30 minutes and then with 35% saturated ammonium sulfate. The resultant precipitate was subjected to treatment with Protein A-Sepharose CL-4B (Pharmacia) for antibody purification. The whole volume of the antibody solution was made 16 ml. Ouchterlony's test confirmed that the protease protein and the antibody reacted with each other to give an immunoprecipitate. The IgG (immunoglobulin G) fraction obtained from a control rabbit (no protease injection) did not show any immunoprecipitation reaction with the protease.

(1-ii) Formation of a genomic DNA library from *A. chrysogenum* ATCC 11550:

The genomic DNA was extracted from *A. chrysogenum* ATCC 11550 by the method described in Japanese Kokai Tokkyo Koho No. 61-209593 (Isogai et al.; laid open Sep. 17, 1986). This DNA (about 25 μg) was treated with the restriction enzyme EcoRI (100 units.) at 37° C. for 3 hours for partial cleavage and the digest was subjected to sucrose density gradient centrifugation (5 to 20% sucrose; Hitachi ultracentrifuge rotor RPS 55T-2, 50 krpm, 4 hours) to give a purified DNA fraction (about 3 Kbp or more in size). The size-fractionated DNA was finally dissolved in 100 μl of TE buffer. Separately, the λgtWES•λB DNA [Bethesda Research Laboratories (BRL)] (about 40 μg) was completely cleaved with EcoEI and the digest was subjected to sucrose density gradient centrifugation (under the same conditions as mentioned above), whereby a 4.85-Kbp DNA was removed and a 21.7-Kbp left arm and a 13.8-Kbp right arm were purified. The DNA fragment obtained by partial cleavage with EcoEI (>3 Kbp, about 5 μg) and the λgtWES•λB-derived EcoRI arms (about 15 μg) were mixed up and subjected to ligation using T4 DNA ligase. The ligation mixture was subjected to in vitro packaging using Packer-Gene [λ phage in vitro packaging system; Promega Biotec (imported and distributed by Seikagaku Kogyo)]. Plaque formation using *E. coli* DP50 supF (included in the PackerGene kit) as a host gave about $2 \times 10^6$ plaques. Thus a genomic DNA library consisting of about $2 \times 10^6$ clones could be constructed.

(1-iii) Extraction and purification of mRNA from *A. chrysogenum* ATCC 11550:

*A. chrysogenum* ATCC 11550 was cultured in 100 μl of an aqueous medium containing 4.5% soluble starch, 3% corn steep liquor (CSL), 1.5% soybean meal and 0.35% $CaCO_3$ at 25° C. for 4 days. The cells obtained were disrupted in a mortar cooled to a low temperature with liquefied nitrogen, then suspended in 40 ml of a guanidine isothiocyanate solution [4M guanidine isothiocyanate, 50 mM Tris-HCl (pH 7.5)., 20 mM EDTA, 2% N-lauroylsarcosine sodium, 0.17M 2-mercaptoethanol] and heated at 60° C. for 5 minutes. The suspension was then centrifuged at 10,800 x g for 10 minutes and 13 mg of whole RNA was recovered from the supernatant by the guanidine-cesium chloride method (cf. Molecular Cloning, page 196, Cold Spring Harbor Laboratory, 1982).

Two purifications of the whole RNA (13 mg) using 1 g of oligo(dT)-cellulose (BRL) [cf. Molecular Cloning (1982), page 197] gave 460 μg of poly (A)-RNA (mRNA).

(1-iv) Construction of a cDNA library by the Okayama-Berg method:

For obtaining a nearly full-length cDNA, a cDNA library was constructed by the Okayama-Berg method [cf. H. Okayama and P. Berg, Mol. Cell. Biol., 2, 161 1982)]. The mRNA (4 μg) obtained in (1-iii) and 0.9 μg of a primer [3'-oligo(dT)-tailed pSV7186-derived plasmid primer (Pharmacia)] were treated with reverse transcriptase (Seikagaku Kogyo) for synthesizing 0.64 μg of ss-cDNA (single-stranded cDNA). This was treated with terminal transferase for C-tailing (18 C's on the average) and then cleaved with the restriction enzyme HindIII, followed by annealing with 0.25 μg of a linker [3'-oligo(dG)-tailed pSV1932-derived HindIII linker (Pharmacia)] and treatment with *E. coli* DNA ligase. Then ds-cDNA (double-stranded cDNA) was synthesized by treatment of the ligase-treated mixture with RNase H (BRL), DNA polymerase I (Pharmacia) and *E. coli* DNA ligase (Pharmacia). This cDNA was used to transform *E. coli* DH1 (ATCC 33849) by the method of D. Handban [D. Handhan, J. Mol. Biol., 166, 557 (1983)] to give $3.6 \times 10^4$ ampicillin-resistant clones. Thus a cDNA library comprising $3.6 \times 10^4$ clones could be constructed.

(1-v) Cloning of alkaline protease cDNA of *A. chrysogenum* ATCC 11550:

Plasmid DNA was isolated from the cDNA library. consisting of $3.6 \times 10^4$ clones and recloned into λgt11 (ATCC 37194), and the protease gene was searched for by expressblot assay using the protease antibody prepared in (1-i).

The cDNA-derived DNA mixture (20 μg) was cleaved with PstI, then treated with 1.2 units of Bal31 (BRL) (final volume 600 μl) at 37° C. for 5 minutes for rendering the ends blunt and subjected to phenol extraction. The DNA recovered by ethanol precipitation was treated with the Klenow fragment (large fragment *E. coli* DNA polymerase I) in the presence of dNTP, followed by phenol extraction and ethanol precipitation. The DNA recovered was treated with. EcoRI methylase (New England Biolabs) in the presence of S-adenosylmethionine for methylation of the EcoRI site to render said site unclearable with EcoRI. About 10 μg of this DNA and 5 μg of a pEcoRI linker [d(pG-G-A-A-T-T-C-C); Takara Shuzo] were mixed up and ligated to each other using T4 DNA ligase. After inactivation of the enzyme by treating at 65° C. for 15 minutes, the ligation mixture was cleaved with EcoRI. The pEcoRI linker was removed by 5% acrylamide gel electrophoresis. DNA was eluted from the acrylamide gel with an eluting buffer (0.5M $CH_3COONH_4$, 10 mM magnesium acetate, 1 mM EDTA, 1% SDS) and purified on DE52 (Pharmacia) [in 10 mM Tris-HCl (pH 7.5), 5 mM EDTA; adsorption with 0.1M MACl; desorption with 1M NaCl; a spun column used].

Protoclone GT11 DNA (Promega Biotec, distributed by Seikagaku Kogyo; 2 µg) (prepared from purified λgt11 DNA by treatment with DNA ligase, cleavage with EcoRI and treatment with alkaline phosphatase) and the cDNA mixture treated as described above were mixed up and ligated to each other using T4 DNA ligase. The resultant DNA mixture was subjected to in vitro packaging using PackerGene (λ phage in vitro packaging system, Promega Biotec), followed by plaque formation with *E. coli* Y1090 (r⁻m⁺) (ATCC 37197) as a host. About 3×10⁵ plaques were obtained. Upon observation of the plaques in the presence of X-gal and IPTG, about 75% were white plaques and the remaining (about 25%) were blue plaques.

A mixture of a culture (0.1 ml) of *E. coli* Y1090 (r⁻m⁺), the above-mentioned λgt11-derived cDNA library (about 1×10⁴ clones) and a top layer agar (the same as LB agar except for the agar concentration which was 0.8%) (3 ml) was spread over 20 ml of LB agar containing 50 µg/ml ampicillin as placed in a dish (about 8.5 cm in diameter) and the dish contests were allowed to stand at room temperature for 1 hour for agar solidification and then incubated at 42° C. for 4 hours. A nitrocellulose filter (82.5 mm in diameter; Bio-Rad Laboratories) was immersed in 10 mM IPTG solution for 1 hour and then dried at room temperature for about 1 hour. This filter was placed on the above-mentioned dish culture and incubation was further conducted at 37° C. for 2.5 hours for allowing gene expression and blotting onto the filter. From among about 7×10⁴ plaques resulting from such blotting, six positive clones were isolated by using an express-blot assay kit (Bio-Rad) and the antibody produced in (1-i). The express-blot assay (cf. T. V. Huynh et al., DNA Cloning, volume I, pages 73–75,IRL Press, 1985) was performed as described in the manual attached to the kit. Following fused protein expression and blocking of the plaque-lifted filter with gelatin, the filter was reacted with a rabbit-derived protease antibody neutralized with *E. coli* lysate (included in the kit) [neutralized by adding 0.2 ml of *E. coli* lysate and 4 µl of protease antibody to 20 ml of antibody incubation buffer (cf. the manual attached to the kit)] and then with HRP (horseraddish peroxidase)-labeled anti-rabbit IgG (included in the kit). Upon the subsequent color development, positive clones gave blue-violet spots, while negative clones and rabbit-derived control antibodies gave no such spots.

DNA was isolated from each of the above six positive clones and cleaved with restriction enzymes for comparison of cDNA inserts with respect to length. The clone having the longest insert was named. λgt-Protease2 (cf. FIG. 1B). The remaining five clones each gave a similar restriction enzyme cleavage map.

(1-vi) Cloning of the protease cDNA clone λgt-Protease2 into pBR325:

The λgt-Protease2 DNA was cleaved with EcoRI and two DNAs (about 0.5 kbp and about 2.6 Kbp) were isolated by agarose gel (0.8%) electrophoresis followed by electrophoretic elution (cf. Molecular Cloning, pages 150 and 164, Cold Spring. Harbor Laboratory, 1982). Separately, the pBR325 (BRL) DNA was cleaved with EcoRI and mixed with one of the above-mentioned two DNA fargments about 0.5 Kbp and about 2.6 Kbp) and ligation was carried out using T4 DNA ligase. Each ligation mixture was used to transform *E. coli* DH1. From among colonies grown on an LB agar plate containing 50 µg/ml ampicillin, transformants incapable of growing on an LB agar plate containing 50 µg/ml chloramphenicol were recovered. Plasmid DNA was isolated from each of these transformant strains and subjected to restriction enzyme cleavage for insert confirmation. One of the plasmids containing the 0.5 Kbp DNA was named pBR-Pro2-E2 (containing a protease cDNA fragment corresponding to the neighborhood of the N terminus) and one of the plasmids with %he 5.6 Kbp DNA insert was named pBR-Pro2-E3 (containing a protease cDNA fragment corresponding to the C terminus side).

(1-vii) Cloning of genomic protease DNA clones λ-G-Protease-1413 and λ-G-Protease-0112:

From about 5×10⁴ clones of the *A. chrysogenum* ATCC 11550-derived genomic DNA library constructed in (1-ii), two genomic protease DNA clones, λ-G-Protease-1413 and λ-G-Protease-0112 (cf. FIG. 1–2), were cloned using pBR-Pro2-E2 and pBR-Pro2-E3 as probes.

A mixture of a culture of *E. coli* DP50supF (Promega Biotec) (0.1 ml), the genomic DNA library prepared in (1-ii) (about 1×10⁴ clones) and a top agar (the same as LB agar except for the agar concentration which was 0.8%) (3 ml) was spread over 20 ml of LB agar containing 10 mM MgCl₂ as placed in a dish (about 8.5 cm in diameter) and the dish was incubated overnight at 37° C. Phage transfer to a nitrocellulose filter (85 mm in diameter; BioRad) was performed by the method described in Advanced Bacterial Genetics, pages 162 and 174 (Cold Spring Harbor Laboratory, 1980), followed by denaturation and neutralization and by Southern hybridization using a ³²P-labeled DNA mixture of pBR322-Pro2-E2 and pBR-Pro2-E3.for recovering positive clones. DNA labeling with ³²P was performed by the nick translation method (Molecular Cloning, page 109, Cold Spring Harbor Laboratory, 1982) using α-³²P-dCTP.

From about 5×10⁴ plaques, nine positive clones were isolated. From these were obtained 8 clones by monoplaque isolation in the same manner as mentioned above. DNA was recovered from each of these clones, cleaved with EcoRI and subjected to agarose gel (0.8%) electrohoresis, followed by Southern hybridization by the method of Southern [E. M. Southern, J. Mol. Biol., 98, 116 (1975)] using as a DNA probe pBR-Pro2-E2 or pBR-Pro2-E3 labeled with ³²p by the method mentioned above. One of the four clones found positive with the pBR-Pro2-E3 probe was named λ-G-Protease-0112 (cf. FIG. 1B), while one of the four clones found positive with the pBR-Pro2-E3 was named λ-G-Protease-1413 (cf. FIG. 1B).

(1-viii) Construction of genomic protease DNAs, pGR2-EH1 and pGR3-EH1:

pGPR2-EH1 was constructed by subcloning the λ-G-Protease-0112 DNA into pBR322 (BRL) (cf. FIG. 1B), and pGRB-EH1 by subcloning the λ-G-Protease-1413 DNA into pBR322.

Thus, the λ-G-Protease-0112 DNA was cleaved with EcoRI and HindIII and a DNA fragment of about 3.5 Kbp was isolated by agarose gel (0.8%) electrophoresis followed by electrophoretic elution. Separately, the pBR322 DNA was cleaved with EcoRI and HindIII and the cleavage mixture was mixed with the above-mentioned DNA fragment (about 3.5 Kbp). Ligation was effected using T4 DNA ligase. The ligation mixture was used to transform *E. coli* DH1. From the colonies grown on an LB agar plate containing 50 µg/ml of ampicillin, those transformants that could not grow on an LB agar plate containing 10 µg/ml of tetracycline were recovered. The plasmid DNA was isolated from one of these transformant strains and named. pGPR2-EH1 (cf. FIG. 1B). Similarly, the λ-G-Protease-1413 DNA was cleaved with EcoRI and HindIII, a DNA fragment of about 3.7 Kbp was isolated by agarose gel electrophoresis followed by electrophoretic elution and cloned into the EcoRI-HindIII fragment of pBR322. In this way, pGPR3-EH1 (cf. FIG. 1B) was constructed.

Southern hybridization carried out in the same manner as performed in (1-vii) for λ-G-Protease-0112 or λ-G-Protease-1413 revealed that the above plasmids pGPR2-EH1 and pGPR3-EH1 were the desired ones. (In this case, the DNAs were subjected to double digestion with EcoRI and HindIII and $^{32}$p probes corresponding to the respective inserts were used.)

(1-ix) Determination of the nucleotide sequences of the protease gene cDNA and genomic DNA derived from *A. chrysogenum* ATCC 11550:

The nucleotide sequences of the cDNA portion (about 1.5 Kbp) of λgt-Protease2, the XhoI-EcoRI fragment (about 1.4 Kbp) of pGPR2-EH1 and the EcoRI-PstI fragment (about 1.5 Kbp) of pGPR3-EH1 were determined by the dideoxynucleotide synthetic chain termination method [F. Sanger et al., Proc. Natl. Acad. Sci. USA, 74, 5463 (1977)] using the M13mp10 and M13mp11 vectors (Amersham) together with α-$^{32}$P-dCTP. The results obtained are shown in FIGS. 1D–1F and FIGS. 1G and 1H. The long open reading frame of λgt-Protease2 is shown in FIG. 1K. Since this cDNA was obtained based on expression of a protein fused with λgt11 β-galactosidase followed by screening with the antibody mentioned above, the cDNA and β-galactosidase gene were supposed to be in the same translational reading frame and the result of translation was estimated. The result is shown in FIGS. 1I and 1J. It is evident that the two frames are just in phase. Furthermore it was found that the cDNA was joined to λgt11 via a 21-bp GC tailing portion. Considering the fact that the Okayama-Berg method was used for cDNA preparation and that the GC tailing formed in said cDNA preparation was found attaching, it was estimated that the cDNA in λgt-Protease2 was almost full-length. The result of analysis of the nucleotide sequence of this cDNA is shown in FIG. 1C A. Comparison in nucleotide sequence between the cDNA and genomic DNA indicated that portion of the genomic DNA which is transcribed into mDNA (cf. FIG. 1C B). The estimated locations of the promoter and terminator upstream and downstream respectively, from said portion are shown in FIG. 1C B.

Comparison in amino acid sequence between the preproprotein to *A. chrysogenum*-derived alkaline protease and the known preproprotein to *Aspergillus oryzae*-derived alkaline protease [Molecular and General Genetics, 219, 33–38 (1989)] revealed that 230 out of the 402 amino acid residues in the former are identical to the corresponding ones in the latter with 57.2% homology and that the former is a serine protease. Based on this data and other -results obtained in a separate study, the primary structure of *A. chrysogenum*-derived mature alkaline protease was estimated to be represented by the amino acid sequence comprising the residues Nos. 1 to 285 as shown in FIG. 1K.

(2) Construction of the plasmid pCYG-B2:

(2-i) Introduction of EcoRI and BamHI synthetic DNA linkers into the *A. chrysogenum* ATCC 115.50-derived protease gene genomic DNA:

The pGPR2-EH1 (cf. FIG. 1B) DNA was cleaved with SmaI, a synthetic EcoRI liner [d(CCGAATTCGG); Takara Shuzo] was added, and ligation was effected using T4 DNA ligase, followed by cleavage with EcoRI and BglII. An EcoRI-BglII fragment (about 1.02Kbp) was isolated by agorose gel (0.8%) electrophoresis followed by electrophoretic elution. This DNA fragment (about 1.02 Kbp) was mixed with an EcoRI-BamHI DNA fragment (4.0 Kbp) of the vector plasmid pBR322 and ligation was carried out using T4 DNA ligase to give the plasmid pGPR-PA3.

The pGPR-PA3 DNA was cleaved with AluI, a synthetic pBamHI linker [d(pCGGATCCG); Takara Shuzo] was added, and ligation was conducted in the presence of T4 DNA ligase. The ligation product was then cleaved with EcoRI and BamHI and an EcoRI-BamHI fragment (about 0.59 Kbp) was isolated by polyacrylamide gel (8%) electrophoresis followed by electrophoretic elution. This DNA fragment (about 0.59 Kbp) was mixed with an EcoRI-BamHI fragment (4.0 Kbp) of the vector plasmid pBR322 and ligation was performed using T4 DNA ligase to give the plasmid pGPR-PA3Q2.

The sites of introduction of the EcoRI and BamHI linkers into the promoter region of the protease gene DNA are shown in FIG. 1L. The nucleotide sequence of the 0.59 Kbp DNA is shown in FIG. 1M.

(2-ii) Introduction of a BamHI synthetic DNA linker into the *A. chrysogenum* ATCC 11550-derived protease genomic DNA:

The pGPR3-EH1 (cf. FIG. 1B) DNA was cleaved with BalI, a synthetic BamHI linker [d(CCGGATCCGG); Takara Shuzo] was added, and ligation was conducted using DNA ligase, followed by cleavage with BamHI, PstI and XhoI. A BamHI-PstI DNA fragment (about 0.92 Kbp) was isolated by agarose gel (0.8%) electrophoresis followed by electrophoretic elution. This DNA fragment (about 0.92 Kbp) was mixed with a BamHI-PstI DNA fragment (2.7 Kbp) of the vector plasmid pUC18 and ligation was effected using T4 DNA ligase to give the plasmid pGPR-TB1.

The site of introduction of the BamHI linker into the terminator region of the protease gene DNA is shown in FIG. 1L. The nucleotide sequence comprising the 0.92-Kbp DNA is shown in FIG. 1N.

(2-iii) Cloning of a promoter and a terminator into pCEP97 (construction of pCYG-B2): (cf. FIG. 1O)

The vector plasmid pCEP97 [cf. Isogai et al., Japanese Kokai Tokkyo Koho No. 61-209593; isolable from Escherichia coli C600 r⁻m⁻ (pCEP97) ATCC 39971 by a conventional method] ($Ap^RCm^R$) (cf. FIG. 1–11) was cleaved with EcoRI and HindIII. Separately, pGPR-PA3Q2 [cf. (2-i); Containing a procter (about 0.59 Kbp)] ($Ap^RCm^S$) was cleaved with EcoRI and BamHI and, further, pGPR-TB1 [cf. (2-ii); containing a terminator (about 0.92 Kbp)]($Ap^RCm^S$) was cleaved with BamHI and HindIII. An EcoRI-HindIII DNA fragment (about 6.1 Kbp) of pCEP97 and a BamHI-HindIII DNA fragment (about 0.93 Kbp) of pGPR-TB1 were respectively isolated by agarose gel (0.8%) electrophoresis followed by electrophoretic elution.

An EcoRI-BamHI DNA fragment (about 0.59 Kbp) of pGPR-PA3Q2 was isolated by acrylamide get (8%) electrophoresis followed by electrophoretic elution. These three DNA fragments were mixed up and ligated to one another using T4 DNA ligase, and the ligation mixture was used to transform *E. coli* DE1. Transformant strains capable of growing on an. LB agar plate containing 50 µg/ml of ampicillin but incapable of growing on an LB agar plate containing 50 µg/ml of chloramphenicol were recovered. The plasmid DNA was isolated from one of these strains and named pCYG-B2 (cf. FIG. 1O). That said DNA was the desired one which was confirmed using restriction enzymes.

(3) Cloning of the genomic IPNS gene DNA (3-i) Extraction and purification of the genomic DNA from *A. chrysogenum* 3112:

*A. chrysogenum* 3112 was grown on a medium (100 ml) containing 1% glucose, 3% soluble starch, 3% corn steep liquor (CSL), 1.5% soybean meal and 0.5% $CoCO_3$ (RE 6.5)

at 30° C. for 5 days. The cells were disrupted in a mortar under cooling with liquefied nitrogen and a buffer was added to Give the following composition: 50 mM Tris-HCl (pH 7.5), 10 mM EDTA and 1% SDS. The resultant mixture was-heated at 65° C. for 10 minutes. After phenol extractions(twice), ethanol precipitation was performed. The precipitate was treated with 5 µg/ml RNase A (Sigma.) and then with 100 µg/ml protease K (Merck). Phenol extractions, ethanol precipitation and sucrose density gradient centrifugation (5 to 20% sucrose; Hitachi ultracentrifuge rotor SRP28; 22 krpm, 13 hours) gave a purified genomic DNA.

(3-ii) Size identification of the genomic isopenicillin N synthetase (IPNS) DNA:

Based on the DNA nucleotide sequence of the *A. chrysogenum*-derived IPNS gene cloned by S. M. Samson et al. [S. M. Samson et al., Nature, 318, 191 (1985)], the following three DNA probes (two 15-meric DNAs and one 12-meric DNA) were synthesized by the method described in Eiko Otsuka: Bunshi Idengaku Jikkenho (Experiments in Molecular Genetics), pages 298–307, Kyoritsu Shuppan, 1983.

Probe [1]: 5'-CTATTCGGCGATGAC-3' (SEQ ID NO:26)

Probe [2]: 5'-AAGGAGAAGAAGCTC-3' (SEQ ID NO:27)

Probe [5]: 5'-CTCCTTGTCATC-3' (SEQ ID NO:28)

Probe [1] and probe [2] were respectively labeled by the method of Inglia et al. [Inglia et al., Nucleic Acids-Res., 9, 1627 (1982)] using T4 polynucleotide. kinase (BRL) and $\gamma^{32}$P-ATP. Then a mixed DNA solution containing the probes [1], [2] and [3] was prepared, heated at 95° C. for 2 minutes and cooled gradually to room temperature for effecting annealing. The annealing product was purfied using NENSORB 20 (Du Pont; imported and distributed by Daiichi Kagaku.) (according to the attached manual). Separately, the *A. chrysogenum* 3112-derived genomic DNA (about 5 prepared in (3-i) was cleaved with BamHI and the cleavage mixture was subjected to agarose gel (0.8%) electrophoresis, followed by transfer to a nitrocellulose filter and Southern hybridization by the method of Southern [E. M. Southern, J. Mol. Biol., 98, 503 (1975)]. The hybridization was performed overnight at 42° C. using 6 x SSC (0.9M NaCl, 0.09M sodium citrate, pH 7.0), 5 x BFP [1 x BFP: 0.02% bovine serum albumin, 0.02% Ficoll (MW: 408,000), 0.02% Polyvinylpyrrolidone], 0.5% SDS, 100 µg/ml carrier DNA (calf thymus DNA) and the labeled DNA mentioned above. The filter was then washed once with 6 x SSC at 55° C. and then twice with 2 x SSC (2 x SSC being a three-fold dilution of 6 x SSC). As a result a DNA fragment of about 3.1 Kbp was found hybridization-positive.

(3-iii) Cloning of the IPNS gene:

About 20 µg of the *A. chrysogenum* 3112-derived genomic DNA prepared in (3-i) was cleaved with BamHI and a DNA mixture (about 2.5 to 4.4 Kbp) was separated by agarose gel (0.8%) electrophoresis followed by electrophoretic elution. Separately, the vector plasmid pBR322 was cleaved with BamHI, the digest was mixed with the above-mentioned DNA mixture (about 2.5 to 4.4 Kbp), then ligation was conducted using T4 DNA ligase, and the ligation mixture was used to transform *E. coli* DH1. About $2.4 \times 10^5$ colonies appeared on an LB agar plate containing 50 µg/ml ampicillin. About 5% of the colonies could not grow on an LB agar plate containing 10 µg/ml tetracycline. Thus, about $1.2 \times 10^4$ colonies contained the *A. chrysogenum* 3112-derived DNA. The plasmid DNA was isolated from each of about $2.4 \times 10^5$ transformants and cleaved with EcoRI. For exclusion of the original vector plasmid free of the *A. chrysogenum* 3112-derived DNA, the EcoRI digest was subjected to agarose gel (0.8%) electrophoresis and a mixture of DNAs about 6.5 to 9.5 Kbp in size was separated by electrophoretic elution. This DNA mixture was subjected to ligation using T4 DNA ligase and the ligation mixture was used to transform *E. coli* DH1. In this way, about $2.6 \times 10^4$ transformants resistant to 50 µg/ml ampicillin were obtained.

The above-mentioned about $2.6 \times 10^4$ genomic DNA-containing *E. coli* transformants were grown on an LB agar plate containing 50 µg/ml ampicillin at 37° C. for 9 hours to give colonies, which were transferred to a nitrocellulose filter and further incubated on an LB agar plate containing 250 µg/ml chloramphenicol at 37° C. for 12 hours. The filter was then treated with 0.5N NaOH-1.5M. NaCl at room temperature for 4 minutes for bacteriolysis and DNA denaturation, then neutralized by treatment with two portions of 0.5M Tris=HCl (pH 7.0)-1.5M MaCl at room temperature for 5 minutes per portion and subjected to hybridization, which was performed by the method described in (3-ii) using the $^{32}$P-labeled 30-meric DNA resulting from joining of probes [1] and [2]. Five hybridization-positive strains were obtained. The plasmid DNAs isolated from these strains were found quite identical to one another when compared by restriction enzyme cleavage analysis. One of the plasmids was named pIPS105 (cf. FIG. 1P).

(3-iv) Cloning of pIPS105 into M13mp10:

Amersham's M13 cloning kit was used and the procedure described in the manual attached to the kit was followed. Thus, the pIPS105 DNA was cleaved with SalI and a DNA fragment of about 0.63 Kbp was isolated by agarose gel (1.5%) electrophoresis followed by electrophoretic elution. This. DNA fragment was mixed with the SalI digest of the M13mp10 DNA and ligation was carried out using T4 DNA ligase. The ligation mixture was used to transform *E. coli* JM105 (Amersham) as a host. White plaques which formed in the presence of X-gal and IPTG were collected and phage multiplication was conducted using *E. coli* JM105 as a host. The RF (replicating form) DNA was isolated from the host cells and named M13mp10-IPS4-2. Similary, the pIPS105 DNA was cleaved with PstI and BamHI and a DNA fragment of about 1.0 Kbp was isolated by agarose gel (0.8%) electrophoresis followed by electrophoretic elution. This DNA fragment (about 1.0 Kbp) was ligated to PstI-BamHI DNA fragments of M13mp10 using T4 DNA ligase. Cloning was carried out in the same manner as above. The phage obtained was multiplicated using *E. coli* JM 105 as a host and the RF DNA was isolated and named M13mp10-IPS3.

The DNA nucleotide sequence of a SalI region of about 0.63 Kbp of the ss-DNA (single-stranded DNA) of M13mp10-IPS4-2 was determined by the dideoxynucleotide synthetic chain termination method (using Amersham's sequencing kit). The 478 bp SalI-NcoI DNA fragment out of said region is illustrated in FIG. 1Q. In this way, the presence of the IPNS gene could be confirmed and the promoter region could be identified. The restriction enzyme map of the IPNS terminator of M13mp10-IPS3 and the multicloning site portion of M13mp10 is shown in FIG. 1R. The IPNS gene promoter and terminator can be readily synthesized by means of a DNA synthesizer on the basis of the DNA nucleotide sequences shown in FIG. 1Q and FIG. 1T, respectively.

(4) Construction of pCYG-EB2 (cf. FIG. 1–15)

(4-i) Deletion of the BamHI site from M13mp10-IPS3 (cf. FIG. 1P):

The RF DNA of M13mp10-IPS3 was cleaved with BamHI, then repaired using the Klenow fragment (large fragment E. coli DNA polymerase I; Amersham) in the presence of dNTP, subjected to ligation using T4 DNA ligase and again cleaved with BamHI. The cleavage mixture was used to transform E. coli JM105 and phage plaques were collected. The phage was multiplied using E. coli JM105 as a host and the RF DNA was separated from the host cells. This DNA was named M13mp10-IPS3-DS and it was confirmed that said DNA could not be cleaved with BamHI. The DNA nucleotide sequence of the terminator-containing BclI-EcoRI region. (about 1.0 Kbp) of M13mp10-IPS3-D8 was determined by the dideoxynucleotide synthetic chain termination method using $\alpha$-$^{32}$P-dATP and sequenase. The sequence is shown in FIG. 1T.

(4-ii) Joining of the IPNS promoter to the G418 resistance gene:

The G418 resistance gene of Tn903 [A. Oka et al., J. Mol. Biol., 147, 217 (1987)] (PvuII 1696 bp fragment) was purified from the PvuII-cleaved DNA of pCYG97 [cf. Japanese Kokai Tokkyo Koho No. 61-209593; isolable from Escherichia coli C600 r-m- (pCYG97) ATCC 399770 by a conventional method]. To this 1696 bp DNA fragment was added a synthetic BamHI linker [d(CCGGATCCGG; Takara Shuzo] was added, and ligation was carried out using T4 DNA ligase. The ligation mixture was subjected to cleavage with BamHI and ethanol precipitations (three times) to thereby remove the linker DNA remaining unbound. Separately, the pUC18 DNA (Takara Shuzo) was cleaved with BamHI, the digest was mixed with the above-mentioned BamHI linker-bound 1.7 Kbp DNA fragment, and ligation was performed using T4 DNA ligase. The resulting DNA solution was used to transform E. coli JM109 (Takara Shuzo) and transformants grown on an LB agar plate containing 20 μg/ml kanamycin were obtained. The plasmid DNA was isolated from one of these transformants and named pUC-Tn903-F1. Its structure was confirmed using restriction enzymes. The pUC-Tn903-F1 DNA was cleaved with XhoI and BamHI and a DNA fragment of about 1.21 Kbp was isolated by agarose gel (0.8%). electrophoresis followed by electrophoretic elution. Separately, the IPNS gene promoter was isolated from the M13mp10=IPS4-2 RF DNA by cleavage with HindIII and NcoI followed by acrylamide gel (8%) electrophoresis and electrophoretic elution as a DNA fragment (HingIII. PstI•SalI-NcoI) of about 0.49 Kbp. ATG occurs in this NcoI site. Therefore, for allowing expression of the G4.18 resistance (kanamycin resistance) gene, the NcoI site was linked to the XhoI site by means of a synthetic DNA. Thus, two 31-meric synthetic DNAs (shown below) were synthesized using an Applied Biosystems model 381A DNA synthesizer.

5'-CATGAGCCATATTCAACGGGAAACGTCTTGC-3' (SEQ ID NO:29)

5'-TCGAGCAAGACGTTTCCCGTTGAATATGGCT-3' (SEQ ID NO:30)

The two synthetic DNAs (10 μg each) were mixed up in 100 μl of TE buffer, heated at 95° C. for 2 minutes and then gradually cooled to room temperature for annealing. The 4.0 Kbp HindIII-BamHI fragment derived from the vector plasmid pBR322, the M13mp10-IPS4-2-derived HindIII-NcoI fragment (about 0.49 Kbp), the annealed synthetic DNA (31 bp) and the pUC-Tn903-F1-derived XhoI-BamHI fragment (about 1.21 Kbp) were mixed up and ligation was carried out using T4 DNA ligase. The ligation mixture was used to transform E. coli by the method of D. Hanahan [D. Hanahan, J. Mol. Biol., 166, 557 (1983)] and ampicillin-resistant, tetracycline-sensitive transformants were obtained. The plasmid DNA was isolated from each of these transformants and subjected to restriction enzyme analysis for structure confirmation. One of the plasmids was named pBCG-D3.

(4-iii) Joining of the IPNS terminator to the G418 resistance gene:

The RF DNA of M13mp10-IPS3-DS as prepared in (4-i) was cleaved with PvuII and BclI and a DNA fragment of about 1.1 Kbp was isolated by agarose gel (0.8%) electrophoresis followed by electrophoretic elution. Separately, the pBCG-D3 DNA prepared in (4-ii) was cleaved with BamHI and PvuII and a BamHI-PvuII DNA fragment of about 4.05 Kbp was isolated by agarose gel (0.8%) electrophoresis followed by electrophoretic elution. The BclI-PvuII DNA fragment (BclI-SacI-SmaI. SacI-EcoRI-PvuII) (about 1.1 Kbp) and the BamHI-PvuII DNA fragment (about 4.05 Kbp) were mixed up and ligation was carried out using T4 DNA ligase. The ligation mixture was used to transform E. coli DH1. The plasmid DNA was isolated from each of the ampicillin-resistant transformants thus obtained and the structure thereof was confirmed by analysis with restriction enzymes. One of the plasmids was named pBCG-DT1.

(4-iv) Cloning of the G418 resistance expression unit into pcEP97 (cf. FIG. 1S):

About 10 μg of the pCEP97 DNA (cf. FIG. 1S) was treated with 30 units of PvuII at 37° C. for 1 hour (final volume: 200 μl) for partial cleavage of the DNA. Following phenol extraction and ether extraction, DNA was precipitated with ethanol. This DNA was then completely cleaved with SalI and a DNA of about 6.0 Kbp was isolated by agarose gel (0.8%) electrophoresis followed by electrophoretic elution. Separately, about 10 μg of the pBCG-DT1 DNA prepared is (4-iii) was treated with 20 units of SmaI at 37° C. for 30 minutes (final volume: 100 μl). for partial cleavage. Following phenol extraction .and ether extraction, DNA was precipitated with ethanol. This DNA was then completely cleaved with SalI and a DNA fragment of about 2.7 Kbp was isolated by agarose gel (0.8%) electrophoresis followed by electrophoretic elution. The PvuII-PvuII-SalI DNA fragment (about 6.0 Kbp) and the SalI-SmaI-SmaI DNA fragment (about 5.7 Kbp) were mixed up and ligation was carried out using T4 DNA ligase. The ligation mixture was used to transform E. coli DH1. Out of the colonies grown on an LB agar plate containing 50 μg/ml ampicillin, 64 transformants capable of growing on an LB agar plate containing 35 μg/ml chloramphenicol were obtained. The plasmid DNA was isolated from each of them and examined for plasmid size by agarose gel (0.8%) electrophoresis, whereupon 13 transformants were found to be the desired ones. One of them was called pCYG-E15 (cf. FIG. 1S) and the structure thereof was confirmed by analysis using restriction enzymes.

(4-v) Cloning of a protease expression unit into pCYG-E15 (construction of pCYG-EB2) (cf. FIG. 1S):

About 20 μg of the pCYG-E15 DNA prepared in (4-iv) was treated with 8 units of HindIII at 37° C. for 30 minutes (final volume: 200 μl) for partial cleavage of the DNA. After phenol extraction and ether extraction, DNA was precipitated with ethanol. This DNA was then completely cleaved with EcoRI and a DNA fragment of about 7.4 Kbp was isolated by agarose gel (0.8%) electrophoresis followed by electrophoretic elution. Separately, pCYG-B2 (cf. FIG. 1O) was cleaved with EcoRI and HindIII and a DNA fragment of about 1.5 Kbp was isolated by agarose gel (0.8%) electrophoresis followed by electrophoretic elution. The HindIII-HindIII-EcoRI DNA fragment (about 7.4 Kbp) and the EcoRI-HindIII DNA fragment (about 1.5 Kbp) were mixed up and ligation was carried out using T4 DNA ligase. The ligation mixture was used to transform E. coli DE1. Out of the colonies grown on an LB agar plate containing 50 μg/ml ampicillin, transformants incapable of growing on an LB agar plate containing 35 µg/ml chloramphenicol were separated. The plasmid DNA was isolated from each of these transformants and analyzed using restriction enzymes for structure confirmation. One of the desired plasmids thus obtained was named pCYG-EB2 (cf. FIG. 1S).

EXAMPLE 2

A plasmid, DCYG-HB51, capable of expressing $Hm^R$ in *A. chrysogenum* was constructed by introducing the plasmid pLG90-derived $Hm^R$ gene with its 5' side modified with a synthetic DNA into the plasmid pCYG-B2 (cf. FIG. 1–11) containing a protease gene expression unit, at the BamHI site thereof (cf. FIG. 2-1). The plasmid pLG90 and a method of constructing the same are known [cf. P. J. M. van den Elzen et al. Plant Molecular Biology, 5, 299–302 (1985) and L. Gritz and J. Davies, Gene, 25, 179–188 (1983)].

(1) Construction of the plasmid pCYG-HB51

(i) Construction of a plasmid, pHMP-E5:

pLG90 was cleaved with the restriction enzyme HphI and then with the restriction enzyme BamHI. An HphI-BamHI fragment (about 1.03 Kbp) was isolated by agarose gel (1.5%) electrophoresis followed by electrophoretic elution [cf. Molecular Cloning (cited above), pages 150 and 164].

Separately, for deleting ATG occurring just upstream from the ATG codon in the $Hm^R$ BamHI DNA fragment of pLG90 the 28-meric and 33-meric DNAs shown in FIG. 2A were Synthesized using an Applied Biosystems model 381A DNA synthesizer according to the operator's manual therefor. The DNAs synthesized were purified using an Applied Biosystems oligonucleotide purification cartridge (OPC cartridge) according to the manual therefor. The DNAs synthesized (each 10 µg) were mixed up in a final volume of 100 µl of TE buffer and heated at 95° C. for 10 minutes. The mixture was then gradually cooled to room temperature for effecting annealing of the two DNAs.

28 mer 5'-TTTTTCATAGCTGTTTCCTGTGGATCCG-3' (SEQ. ID NO:31)

33 mer 5'-AATTCGGATCCACAGGAAACAGCTATGAAAAAG-3' (SEQ. ID NO:32)

A mixed solution containing three DNAs, namely the annealed synthetic DNA, the HphI-BamHI DNA fragment (about 1.03 Kbp) obtained above and an EcoRI-BamHI fragment (2.7 Kbp) of the plasmid pUC18 (Takara Shuzo), was prepared and ligation was carried out using T4 DNA ligase. The ligation mixture was used to transform *E. coli* JM109 (Takara Shuzo). Out of the colonies grown on an LB agar plate containing 50 µg/ml ampicillin, transformants capable of growing on an LB agar plate containing 150 µg/ml hygromycin B and 0.5 mM IPTG were separated. The plasmid isolated from one of the transformants was named pHMP-E5 (cf. FIG. 2A). Its structure was confirmed using restriction enzymes. nucleotide sequence of a synthetic DNA region-containing portion of pHMP-E5 was, determined by the dideoxynucleotide synthetic chain termination method and found to be as designed.

(ii) Construction of pCYG-HB51:

pHMP-E5 was cleaved with BamHI and a DNA about 1.06 Kbp in size was isolated by agarose gel (0.8%) electrophoresis followed by electrophoretic elution. Separately, the expression vector in *A. chrysogenum* pCYG-B2 (cf. FIG. 1O) was cleaved with BamHI. Both BamHI DNA fragments were mixed up and ligated to each other using T4 DNA ligase, and the ligation mixture was used to transform *E. coli* JM109. Out of the colonies grown on an LB agar plate containing 50 µg/ml ampicillin, transformants capable of growing on an LB agar plate containing 150 µg/ml hygromycin B were collected. Since both the *A. chrysogenum* ATCC 11550-derived protease gene promoter and terminator show promoter activity in *E. coli*, the presence of an SD sequence (ribosome binding site sequence) before an ATG codon would induce translation in *E. coli*. Therefore, the $Ap^R Hm^R$ strains might include strains containing the $Hm^R$ gene in one direction and strains containing said gene in the reverse direction. Therefore the plasmid DNA was isolated from each of these strains, and cleaved with EcoRI and the direction of the $Hm^R$ gene was judged by agarose gel (0.8%) electrophoresis. One of the plasmids in which said gene was in the same direction with that of the protease gene promoter was named pCYG-HB51 (cf. FIG. 2A). The nucleotide sequence of the hygromycin B resistance gene inserted in this plasmid pCYG-HB51 is shown in FIGS. 2B and 2C, together with the amino acid sequence encoded by said nucleotide sequence.

EXAMPLE 3

(1) Construction of the plasmid pDAO-EB101 (expression vector for a D-amino acid oxidase gene) and the plasmid pVEB104 (expression vector for a CC acylase gene)

For direct fermentative production of 7ACA or 7ADCA using a cephalosporin C (CC)- or deacetylcephalosporin C (DCC)-producing microorganism belonging to the species *Acremonium chrysogenum*, the routes shown in FIG. 3B were conceived. Thus the routes should respectively include:

(1) transformation of a CC or DCC producer With a 7ACA or 7ADCA production vector containing a CC acylase gene;

(2) transformation of a CC or DCC producer with a 7ACA or 7ADCA production vector containing a D-amino acid oxidase (DAO) gene and a CC acylase gene; and (3) transformation of a CC or DCC producer with a 7ACA or 7ADCA production vector containing a DAO gene and a GL-7ACA acylase gene.

For the above purposes, an expression vector containing a CC acylase gene and an expression vector containing a DAO gene were prepared. It was confirmed that each enzyme could be expressed in *Saccharomyces cerevisiae*. The procedure followed in this Example 3 is schematically shown in FIG. 3A.

(i) Construction of pDAO-EB101:

The DAO expression plasmid pCFS315 (cf. FIG. 3E) was isolated from *E. coli* JM109 (pCFS315). (FERM BP-1916) by a conventional method and cleaved with BamHI, and a 1.24 Kbp DNA was isolated by agorose gel (0.8%) electrophoresis followed by electrophoretic elution. The nucleotide sequence of the DAO cDNA contained in the plasmid pCFS315 is shown in FIGS. 3–11. Separately, the vector pCYG-EB2 DNA (cf. FIGS. 1–15) having an expression unit in *A. chrysogenum* was cleaved with BamHI. Both the BamHI DNA fragments were mixed up and ligated to each other using T4 DNA ligase. The ligation mixture was used to transform *E coli* DE1 (ATCC 33849). Transformants capable of growing on an LB agar plate containing 50 µg/ml ampicillin were collected. The plasmid DNA was isolated from each of these transformants, cleaved with BamHI or EcoRI+PvuII and subjected to agorose gel (1.5%) electropharesis. One of the plasmids that gave a 1.24 Kbp DNA fragment upon BamHI cleavage and a 1.33 Kbp DNA fragment upon EcoRI+PvuII cleavage was named pDAO-EB101 (cf. FIG. 3C).

(ii) Construction of pVEB104:

*Pseudomonas diminuta* V22 showing CC acylase activity was isolated from a soil sample and an acylase gene was cloned from the genomic DNA thereof using *E. coli* as a host, with CC acylase activity as a index. The N-terminal side of this gene was excised with PstI, the C-terminal side was deleted by treatment with Bal31 to reduce the gene size to about 3 Kbp, and pCPV22P (cf. FIG. 3-6) was constructed using this gene and $Km^R$ pHSG298 [Tahara Shuzo; S. Takeshita et al., Gene, 61, 63–74 (1987)] as the vector therefor.

Starting with the CC acylase gene of pCPV22P and deleting the N-terminal side to the MluI site located upstream from ATG, pV22B1 was constructed (of FIG. 3F).

It was found that, in the vicinity of an AatII site just upstream from the ATG codon of the V22 CC acylase gene, there was another ATG belonging to a different frame. Therefore this ATG was deleted by using a synthetic DNA adapter and pV22BS-A11 (cf. FIG. 3I) was constructed. By cloning the acylase gene, with said ATG deleted, in the expression vector pCYG-EB2, pVEB104 (cf. FIG. 3D) was constructed.

(a) Construction of pV22B1 and determination of the N-terminal side nucleotide sequence:

The pCPV22P plasmid was isolated from *E. coli* JM109 (pCPV22P) (FERM-BP 2704) and 15 μg of this DNA was treated with 30 units of the restriction enzyme, MluI (Toyoho) at 37° C. for 15 minutes for partial cleavage of the DNA. Following phenol extraction and ether extraction, DNA was precipitated with ethanol and treated with the Klenow fragment (large fragment *E. coli* DNA polymerase I) (Takara Shuzo) in the presence of dNTP for rendering the cleavage site blunt-ended. Following phenol extraction and ether extraction, DNA was precipitated with ethanol. The DNA was cleaved with EcoRI and a DNA about 1.1 Kbp in size was isolated by agarose gel (1.5%) electrophoresis followed by electrophoretic elution. The above DNA fragment (about 1.1 Kbp) and a SmaI-EcoRI DNA fragment (2.7 Kbp) of the vector plasmid pUC19 (Takara Shuzo) were mixed up and ligated to each other using T4. DNA ligase to give a plasmid, pV22F2 (cf. FIG. 3F).

Since there was no BamHI site on the acylase C-terminus side, introduction of a BamHI site on the C terminus side was attempted by reversing the direction of the acylase gene of pCPV22P. Thus, pCPV22P was cleaved with PstI and selected to religation using T4 DNA ligase, and the religation mixture was used to transform *E. coli* JM109. White transformant colonies grown on an LB agar plate containing 50 μg/ml, 100 μg/ml X-gal and 0.5 mM IPTG were recovered (blue clones contained the vector pHSG298 having no acylase gene insert). The plasmid DNA was isolated from each of these transformants and cleaved with SalI, and pV22R6 (cf. FIG. 3F) with the acylase gene inserted therein in the reverse direction was isolated by agarose gel (0.8%) electrophoresis.

PV22F2 was cleaved with HindIII and EcoRI, and a HindIII-EcoRI fragment (about 1.2 Kbp) was isolated by agarose gel (0.8%) electrophoresis followed by electrophoretic elution. Separately, pV22R6 was cleaved with EcoRI and BamHI and an EcoRI-BamHI fragment (about 1.4 Kbp) was isolated by agaross gel (0.8%) electrophoresis followed by electrophoretic, elution. The above-mentioned HindIII-EcoRI fragment (about 1.2 Kbp) and EcoRI-BamHI fragment (about 1.4 Kbp) and further a HindIII-BamHI fragment of the vector plasmid pHSG399 [Takara Shuzo; plasmid containing $Cm^R$ as a marker; *E. coli* JM109 (pHSG399) can grow or an LB agar plate containing 30 μg/ml chloramphenicol] were mixed up and ligation was carried out using T4 DNA ligase to give the plasmid pV22B1 (cf. FIG. 3F).

pV22B1 was cleaved with BamHI and EcoRI and a BamHI-EcoRI fragment (about 2.5 Kbp) was isolated by agarose gel (0.8%) electrophoresis followed by electrophoretic elution. This DNA fragment was cloned into an EcoRI-BamHI fragment of M13mp18 and of M13mp19 and the DNA nucleotide sequence of the open reading frame of the acylase gene inserted in pV22B1. was determined (cf. FIGS. 3A and 3H). For the nucleotide sequence determination, $\alpha$-$^{32}$P-dATP and seguenase [cf. S. Tabor and C. C. Richardson, J. Biol. Chem., 264, 6447 (1989)] (United States Biochemical Corporation) were used and the dideoxynucleotide synthetic chain termination method of Sanger et al. [F. Sanger et al., Proc. Natl. Acd. Sci. USA, 74, 5463 (1977)] was followed. Comparison of the amino acid sequences of the V22-derived acylase and the known *Pseudomonas sp.* SE83-derived acylase [A. Matsuda et al., J. Bacteriol., 169, 5821 (1983)] revealed that 53 out of 774 amino acid residues were different.

(b) Construction of pV22BS-A11 (deletion of ATG upstream from ATG):

pV22B1 was cleaved with EcoRI and DNA fragments of about 3.3 Kbp and about 1.38 Kbp were isolated by agarose gel (0.8%) electrophoresis followed by electrophoretic elution. The 1.38 Kbp DNA fragment was used in constructing pV22BS-A11 from pV22BDS1. The 3.3 Kbp DNA fragment was subjected to ligation using T4 DNA ligase to give a plasmid, pV22BND3 (cf. FIG. 3I).

pV22BD3 was cleaved with AatII and BamHI and a DNA of about 3.3 Kbp was isolated by agarose gel (0.8%) electrophoresis followed by electrophoretic elution. Separately, two synthetic DNAs (19-met and 11-mer) were prepared by a conventional method.

19mer 5'-GATCC GGTACC AAG GACGT-3' (SEQ ID NO:33)

11mer 5'-CCTTGGTACCG-3' (SEQ ID NO:34) The synthetic DNAs were designed such that a KpnI site could be formed for facilitating detection of clones with the same inserted therein. The synthetic DNAs (10 μg each ) were mixed up in a final volume of 100 μl of TE buffer, heated at 90° C. for 2 minutes and cooled gradually to room temperature for effecting annealing of the two DNAs. The above-mentioned AatII-BamHI DNA fragment (about 3.3 Kbp) and the annealing product DNA were mixed up and ligated to each other using T4 DNA ligase to give a plasmid, pV22BDS1 (cf. FIG. 3I). Since this DNA contained the newly introduced KpnI site, it was easy to determine whether the synthetic DNA portion was present in a subsequent product.

pV22BDS1 was cleaved with EcoRI and then mixed with the above-mentioned. EcoRI-EcoRI DNA fragment (about 1.38 Kbp), and ligation was carried out using T4 DNA ligase. The ligation mixture was used to transform *E. coli* DH1 and transformants growing-on an LB agar plate containing 30 μg/ml chloramphenicol were collected. The plasmid DNA was isolated from each of these transformants and cleaved with PstI. Agarose gel (0.8%) electrophoresis gave pV22BS-A11 which contained the 1.38 Kbp EcoRI DNA fragment in the desired direction (cf. FIG. 3I). Cleavage of pV22BS-A11 with PstI gave two DNA fragments about 2.5 Kbp and 2.2 Kbp in size, hence can be readily distinguished from others. The restriction enzyme cleavage map of the acylase gene region (BamHI, about 2.5 Kbp) of pV22BS-A11 is shown in FIG. 3K.

(c) Cloning of the acylase gene of pV22BS-A11 into a gene expression unit capable of functioning in chrysogenum:

pV22BS-A11 was cleaved with BamHI and a DNA of about 2.5 Kbp was isolated by agarose gel (0.8%) electrophoresis followed by electrophoretic elution. Separately, the expression vector pCYG-EB2 (cf. FIG. 1S) for use in *A. chrysogenum* was cleaved with BamHI. Both the BamHI DNA fragments were mixed up and ligated to each other using T4 DNA ligase, and the ligation mixture was used to transform *E. coli* DE1. Transformants growing on an LB agar plate containing 50 µg/ml ampicillin were recovered. The plasmid DNA was isolated from each of these transformants and cleaved with BamHI and EcoRI. One of the plasmids which gave a DNA fragment of about 2.5 Kbp upon cleavage with BamHI and a DNA fragment of about 1.67 Kbp (about 1.96 Kbp if the acylase gene was in the reverse direction) upon cleavage with EcoRI was named pVEB104 (cf. FIG. 3D).

(iii) Expression of pDAO-EB101 and pVEB104 in *S. cerevisiae*:

It was examined whether the *A. chrysogenum* ATCC 11550-derived protease gene expression unit *F. solani* M-0718-derived D-amino acid oxidase cDNA and *P. diminuta* V22-derived acylase gene could function to give enzyme activity in *S. cerevisiae* YNN27 [D. T. Stinchcomb et al., Proc. Natl. Acad. Sci. USA, 77, 4559 (1980)], one of lower eukaryotes.

Transformation of *S. cerevisiae* YNN7 with pDAO-EB101 or pVEB104. was performed as described in Japanese Kokai Tokkyo Koho No. 61-209593 (Isogai et., laid open Sep. 17, 1986) (in Example 2-III). Thus, the protoplast of *S. cerevisiae* YNN27 was mixed with 10 µl (about 5 µg) of each DNA and a buffer containing 20% PEG 4000 was added to the mixture for effecting transformation. Selection using about 300 µg/ml of the antibiotic 0415 gate about 1×10$^4$ transformants.

Each transformant was inoculated into YEPD medium (10 g/liter yeast extract, 20 g/liter peptone, 20 g/liter glucose) (5 ml) containing 10 µg/ml uracil, 40 µg/ml tryptophan and 300 µg/ml G415 and cultivation was carried out at 30° C. for 3 days. Cells were then collected by centifugations. The cells were reacted with CCNa or GL-7ACA and the supernatant separated from cells by centrifugation was subjected to high performance liquid chromatogrphay [column: Inertsil ODS-2 (GasChro Kogyo); mobile phase: solution composed of 6.6 mM phosphate buffer (pH 7.3) and 3% methanol; detection: 254 nm] for product quantification.

In the case of pDAO-EB101-carrying transformants, 500 µl of a reactant solution containing 5 mg/ml CCNa, 0.1M phosphate buffer (pH 7.5) and 14 mM NaN$_3$ and 5 µl of toluene were added to centrifuged cells and the reaction was carried out at 37° C. for 3 hours with shaking. NaN$_3$ was added so that it could inhibit catalase to thereby allow DAO-catalyzed conversion of CCNa to GL-7ACA without stopping at the stage of keto-AD-7ACA. In this way, 840 µg/ml GL-7ACA was formed. In this case, it was also confirmed that transformants carrying pCYG-EB2 containing no DAO gene, which were used as controls, did not give GL-7ACA. It was thus found that the *A. chrysogenum* ATCC 11550-derived protease gene expression unit can function in *S. cerevisiae* YNN27, causing D-amino acid oxidase formation. It was also found that the *F. solani* M-0718-derived DAO cDNA cab be expressed in *S. cerevisiae* YNN27.

In the case of pVEB104-carrying transformants, 500 µl of a reaction solution containing 2 mg/ml GL-7ACA and 0.1M Tris-HCl buffer (pH. 8.0) and 5 µl of toluene were added to centrifuged cells and the reaction was allowed to proceed at 30° C. for 3 hours with shaking, whereby 7ACA was formed in an amount of 15 µg/ml. Control transformants carrying pCYG-EB2 containing no acylase gene failed to cause 7ACA formation. Further it was found that the *P. diminuta* V22-derived acylase gene can be expressed in *S. cerevisiae* YNN27, though to a lesser extent.

EXAMPLE 4

(1) Construction of the plasmids pEBV1 (vector for 7ACA and 7ADCA production), pEDV11 (vector for 7ACA and 7APDA production) and pHBD3 (vector for GL-7ACA and GL-7ADCA production)

In DNA introduction into *Acremonium chrysogenum* BC2116 (FERM-BP 2707), which is a CC and DCC producer, the hygromycin B resistance was used as a marker since selection is difficult when the G418 resistance is used as a selective marker. Thus the CC acylase gene- and Hm$^R$ gene-containing plasmid pHBV1 (cf. FIG. 4A) for 7ACA and 7ADCA production, the D-amino acid oxidase gene-, CC acylase (capable of functioning also as keto-AD-7ACA acylase and GL-7ACA acylase) gene- and Hm$^R$ gene-containing plasmid pHDV11 (cf. FIG. 4B) for 7ACA and 7ADCA production and the D-amino acid oxidase gene- and Hm$^R$ gene-containing plasmid pHBD3 (cf. FIG. 4C) for GL-7ACA and GL-7ADCA production were constructed (i) Construction of pHBV1 (cf. FIG. 4A):

About 15 µg of pCYG-EB51 was treated with 10 units of EcoRI at 37° C. for 15 minutes (final volume: 100 µl) for partial cleavage of the DNA. Following phenol extraction and ether extraction, DNA was precipitated with ethanol. This DNA was then completely cleaved with SmaI and a DNA fragment of about 3.1 Kbp was isolated by agarose gel (0.8%) electrophoresis followed by electrophoretic elution. Separately, pVEB104 was cleaved with SacI and PvuII and a DNA fragment of about 5.7 Kbp was isolated by agarose gel (0.8%) electrophoresis followed by electrophoretic elution. The above-mentioned EcoRI-SmaI fragment (about 3.1 Kbp) and PvuII-SacI DNA fragment (about 5.7 Kbp) and, further, an EcoRI-SacI DNA fragment (2.7. Kbp) of the vector plasmid pHSG298 (Tahara Shuzo) were mixed up and ligation was conducted using T4 DNA ligase. The ligation mixture was used to transform *E. coli* JM109 by the method of D. Hanahan [D. Hanahan, J. Mol. Biol., 163, 557–580 (1983)] and transformants growing as white clones on an LB agar plate containing 20 µg/ml kanamycin, 0.5 mM IPTG and 100 µg/ml X-gal were obtained. From these transformants, those capable of growing on an LB agar plate containing 150 µg/ml hygromycin but incapable of growing on an LB agar plate containing-50 µg/ml ampicillin were recovered. The plasmid DNA was isolated from each of the thus-obtained Km$^R$Hm$^R$Ap$^S$ strains and analyzed by cleavage with restriction enzymes. One of the plasmids thus found to have the desired structure was named pHBV1 (cf. FIG. 4A).

(ii) Construction of pHDV11 (cf. FIG. 4B):

pDAO-EB101 was cleaved with ClaI and a DNA fragment of about 7.5 Kbp was isolated by agarose gel (0.8%) electrophoresis followed by electrophoretic elution. Further, pHBV1 was cleaved with. ClaI (for cleavage at one site alone). The cleavage mixture was mixed with the above-mentioned ClaI fragment (about 7.5 Kbp) and ligation was carried out using T4 DNA ligase. The ligation mixture was used to transform *E. coli* JM109 and transformants growing on an LB agar plate containing 50 µg/ml ampicillin were collected. From among these transformants, strains capable of growing on an LB agar plate containing 150 µg/ml hygromycin but incapable of growing on an LB agar plate containing 30 µg/ml kanamycin were selected. The plasmid DNA was isolated from each of the thus-obtained Ap$^R$Hm-$^R$Km$^S$ strains. Based on the BamHI cleavage pattern, whether said plasmid was the desired one or not was judged and the direction of gene insertion was determined. One of the plasmids thus found to be as designed was named pHDV11 (cf. FIG. 4B).

(iii) Construction of pPIBD3 (cf. FIG. 4C):

About 15 μg of pCYG-HB51 was treated with 10 units of EcoRI at 37° C. for 15 minutes (final volume: 100 μl) for partial cleavage of the DNA. Following phenol extraction and ether extraction, DNA was precipitated with ethanol. This DNA was then completely cleaved with ClaI and a DNA fragment fraction of about 4.3 Kbp was isolated by agarose gel (0.8%) electrophoresis followed by electrophoretic elution said fraction was a mixture of a fragment of about 4.28 Kbp and a fragment of about 4.44 Kbp. If desired, however, the necessary DNA fragment (about 4.28 Kbp) can be isolated by utilizing $Hm^R Ap^S$. Separately, about 20 μg of pDAO-EB101 was treated with 50 units of PstI at 37° C. for 5 minutes (final volume: 200 μl). for partial cleavage of the DNA. Following phenol extraction and ether extraction, DNA was precipitated with ethanol. This DNA was then cleaved with ClaI and a DNA fragment fraction of about 6 Kbp was isolated by agarose gel (0.8%) electrophoresis followed by electrophoretic elution. This DNA fragment fraction included the following three fragments: $PstI^{DAO}PstI$—ClaI (about 5.63 Kbp), $PstI^{DAOP}stI$ ClaI—ClaI (about 6.53 Kbp) and ClaI—$PstI^{DAOP}stI$ (about 5.80 Kbp). If desired, however, the last fragment (about 5.50 Kbp) can be removed by selecting $Ap^S$ transformants.

The above-mentioned first DNA fragment mixture (about 4.3 Kbp) and second DNA fragment mixture (about 6 Kbp) and, further, an EcoRI-PstI fragment (2.6 Kbp) of the vector plasmid pH0298 were mixed up and subjected to ligation using T4 DNA ligase. The ligation mixture was used to transform *E. coli* JM109 by the method of D. Handhah and transformants growing as white colonies on an LB agar plate containing 20 μg/ml kanamycin, 0.5 mM IPTG and 100 μg/ml X-gal were recovered. 800 strains out of these transformants were tested for growing on an LB agar plate containing 150 μg/ml hygromycin and an LB agar plate containing 50 μg/ml ampicillin. Nineteen $Km^R Hm^R Ap^S$ transformants were thus obtained. The plasmid DNA was isolated from each of these strains and subjected to restriction enzyme cleavage analysis for confirmation that it was the desired one. One of the plasmids thus obtained was named pHBD3 (cf. FIG. 4C).

EXAMPLE 5

(1) Introduction of the plasmids pHBV1, pHDV11 and pHBD3 into *A. chrysogenum* BC2116 and cultivation of the transformants

*A. chrysogenum* BC2116 was transformed with pHBV1 or pHDV11 (vector for 7ACA and 7ADCA production in *A. chrysogenum*) or pHBD3 (vector for GL-7ACA and GL-7ADCA production in *A. chrysogenum*). The thus-obtained hygromycin B-resistant transformants were cultivated in a CC production medium (without addition of hygromycin B). It was found that said transformants can produce 7ACA or GL-7ACA in the medium.

(i) Transformation of *A. chrysogenum* BC2116:

(a) Preparation of a uniform inoculum for cell culture:

An ampule of a cell suspension (20% glycerol) obtained by thawing, at 37° C., a stock culture of *A. chrysogenum* BC2116 stored in liquefied nitrogen was inoculated onto ten B3 agar plates dried in advance until the surface moisture could not be observed any longer. The agar plates thus inoculated were incubated at 30° C. for 6 days. The mycelial mass (inclusive of spores) covering each agar plate surface was scraped up while avoiding inclusion of the agar and suspended in 3 ml of 20% glycerol. The suspension was distributed into 5 ampules and, frozen stored in a liquefied nitrogen-cooled cell storage chamber (the ten B3 agar plates giving 50 ampules).

(b) Cell multiplication for protoplast preparation:

The frozen cell suspension (*A. chrysogenum* BC2116) in one ampule was thawed at 37° C. and the whole amount was inoculated into 50 ml of YSP medium placed in a 250-ml shaking flask and shake culture was performed at 30° C. for 4 days. A 5-ml portion of this preculture was transferred to 50 ml of fresh YPS medium and cultivation was conducted at 30° C. as mentioned above for 24 hours.

(c) Protoplast preparation:

Cells were harvested from the thus-obtained 24-hour culture (200 ml) by centrifugation (3,000 rpm, 5 minutes), washed twice with sterile water (200 ml) by centrifugation and suspended in 80 ml of 10 mM Tris HCl (pH 7.5) Containing 10 mM DTT. The suspension was shaken gently at 30° C. for 1 hour. Cells were then collected by centrifugation (3,000 rpm, 5 minutes) washed twice with 100 ml of 1M KCl buffer (pH 5.8) by centrifugation and suspended in 1M KCl buffer (pH 5.8) to a suspension volume of 20 ml. To this suspension (20 ml) was added 30 ml of 1 M KCl buffer (pH 5.8.) containing 16.3 mg/ml Novozyme 234 (Novo Biolabs). The mixture was shaken gently at 30° C. for 30 minutes. After completion of this procedure, the resultant protoplast suspension was placed in a disposable centrifugal tube, stirred for 2 to 3 seconds, then diluted with 50 ml of 1M KP-buffer (pH. 7.5) and centrifuged (750 rpm, 2 minutes). The protoplast sedimented by centrifugation was resuspended in 50 ml of 1M KCl buffer (pH 7.5) and then harvested and at the same time washed by centrifugation (1,500 rpm, 5 minutes). This washing cycle was repeated twice. The protoplast washed was suspended in 0.8M NaP buffer to a final volume of about 5 ml.

(d) Transformation:

To 60 μl (about 20 μg DNA) of each plasmid DNA solution to be used for transformation was added 240 μl of 1M KP buffer (pH 7.5). After mixing up, 400 μl of the protoplast suspension was added. After mixing up, the mixture was allowed to stand in ice for 30 minutes, then 4 ml of 10 mM Tris-HCl (pH 7.5) containing 40% PEG, 10.8% sucrose and 50 mM $CaCl_2$ was added and, after mixing up, the mixture was allowed to stand at room temperature for 15 minutes. Then, 10 ml of 0.8M NaP buffer was added to the mixture and, after mixing up, the whole mixture was centrifuges at 1,000 rpm for 5 minutes. The sediment was suspended in 1.2 ml of 0.8M NaP buffer.

(e) Selection of transformants resistant to the antibiotic hygromycin B:

The transformant suspension (0.2 ml) was mixed with 5 ml of BRM agar medium (48° C.) and the mixture was poured onto a BRM agar medium plate (25 ml). After incubation at 20° C. for 20 hours, 10 mg/ml hygromycin B (Calbiochem Corporation; imported and distributed by Nakalai Tesque) was spread over the plate to a final concentration of 25 μg/ml or 50 μg/ml using a spreader (three plates for each concentration). After 2 to 3 weeks of incubation at 30° C., each colony that had appeared was transferred to a PDA-YE agar plate containing 50 μg/ml hygromycin B. Incubation was further continued at 30° C. for 7 days. In this way, hygromycin B-resistant transformants were obtained. Since abortive transformants cannot grow on fresh medium in the presence of hygromycin B in such subculture as mentioned above, stable transformants can be readily distinguished from abortive transformants. The transformants were each again spread over a PDA-YE agar plate containing 40 a μg/ml hygromycin B and subcultured (30° C., 5 to 7 days).

The above procedure generally gave 1 to 3 hygromycin B-resistant transformants per about 20 μg of DNA. The number of colonies regenerated on the BRM agar medium plate from the final protoplast suspension obtained as described above in section (c) was about $2 \times 10^8$/ml (after 2 weeks of incubation at 30° C.

(ii) 7ACA and GL-7ADCA production by hygromycin B-resistant A. chrysogenum BC2116 transformants:

Hygromycin B-resistant transformants (cf. Table 1) were produced by transforming A. chrysogenum BC2116 with pCYG-HB51 (Hm$^R$ alone), pHBV11 (vector for 7ACA and 7ADCA production), pPIDV11 (vector for 7ACA and 7ADCA production) or pHBD3 (vector for GL-7ACA and GL-7ADCA production) as described above in section (i). Each transformant was inoculated into 50 ml of CS1 medium placed in a 250-ml shaking flask. After 4 days of incubation at 30° C., 1 ml of the resultant preculture was transferred to a 250-ml shaking flask containing 20 ml of the main culture medium and shake culture (stroke: 3 inches; 250 rpm) was conducted at 25° C. for 6 to 7 days. Each main culture was filtered through a Toyo filter paper No. 2 and the filtrate was assayed by HPLC (high-performance liquid chromatography). The HPLC conditions were as follows:

Column: Two columns connected, namely Cosmosil 5C$_{18}$ column (4.6×150 mm) (Nacalai-Tesque) directly followed by Inertsil ODS-2 column (5×150 mm) (Gaskuro Kogyo)

Column temperature: 40° C.

Mobile phase: 4.0. mM (0.567 g/liter) Na$_2$HPO$_4$, 2.6 mM (0.36 g/liter) KH$_2$PO$_4$, 4% methanol Rate of flow: 1 ml/min UV detection: 254 nm Assaying under the above HPLC conditions gave the results shown in Table 1. The positions of (retention times for) 7ACA, GL-7ACA and CCNa were 17.7 minutes, 24.3 minutes and 18.9 minutes, respectively. [Each culture filtrate was 10-fold diluted with 0.5M citrate buffer (pH 4.0) and 10 μl of the dilution was subjected to HPLC.] The results indicate that while transformants obtained with the plasmid pCYG-HB51 characterized by hygromycin B resistance alone produced neither 7ACA nor GL-7ACA, transformants obtained with the vector pHBV1 for 7ACA and 7ADCA production produced 7ACA in an amount of about 50 μg/ml and transformants obtained with the vector pHBD3 for GL-7ACA and GL-7ADCA production produced GL-7ACA in an amount of about 130 μg/ml. Furthermore, transformants obtained with the 7ACA and 7ADCA production vector pEVD11 containing both the D-amino acid oxidase gene and acylase gene produced 7ACA in an amount of about 150 μg/mi but did not produce GL-7ACA or keto-AD-7ACA. Even GL-7ACA producers did not produce keto-AD-7ACA. This is presumably because keto-AD-7ACA was decomposed due to its instability.

TABLE 1

Production of 7ACA and GL-7ACA by hygromycin B-resistant transformants of A. chrysogenum BC2116

| Strain No. | DNA used for transformation | Yield | | |
|---|---|---|---|---|
| | | 7ACA (μg/ml) | GL-7ACA (μg/ml) | CC (mg/ml) |
| Hm144 | pCYG-HB51 | ND | ND | 8.7 |
| Hm172 | | 50 | ND | 7.8 |
| Hm155 | | 55 | ND | 7.3 |
| Hm146 | | 65 | ND | 7.8 |
| Hm154 | pHBV1 | 40 | ND | 7.9 |
| Hm156 | | 50 | ND | 7.0 |
| Hm161 | | 45 | ND | 6.2 |
| Hm178 | pHDV11 | 150 | ND | 4.9 |

TABLE 1-continued

Production of 7ACA and GL-7ACA by hygromycin B-resistant transformants of A. chrysogenum BC2116

| Strain No. | DNA used for transformation | Yield | | |
|---|---|---|---|---|
| | | 7ACA (μg/ml) | GL-7ACA (μg/ml) | CC (mg/ml) |
| Hm165 | | 145 | ND | 5.5 |
| Hm164 | | ND | 130 | 6.5 |
| Hm168 | pHBD3 | ND | 125 | 6.4 |
| Hm179 | | ND | 145 | 6.6 |

ND: Not detected.

For reidentification of the product 7ACA, assaying was further made under different, HPLC conditions to give similar results. The HPLC conditions used in this reassay were as follows:

Column: Cica-Merck pre-packed column for high performance liquid chromatography column (4×250 mm) LiChrospher 100 RP-18(e) (5 μm) (Kanto Chemical)

Column temperature: Room temperature

Mobile phase:
0.92 g/liter Sodium 1-hexanesulfonate (Tokyo Kassei),
1.32 G/liter 18-crown-6 (Nacalai Tesque),
21 g/liter citric acid,
2.47 g/liter trisodium citrate (dihydrate),
10% acetonitrile Rate of flow: 1 ml/min.

UV detection: 254 nm (iii) Analysis of hygromycin-resistant transformants by Southern hybridization:

Hygromycin B-resistant transformants (A. chrysogenum Hm144, Hm172, Hm155, Hm146, Hm154, Hm156, Hm161, Hm178, Hm165, Hm164, Hm168 and Hm179) were each shake-cultured in YPS medium (50 ml) containing 12.5 μg/ml hygromycin B at 30° C. for 5 to 7 days. Cultured cells were collected by centrifugation and stored at −20° C. Cells were disrupted in a mortar cooled with liquefied nitrogen, 5 ml of 50 mM Tris-HCl buffer 7.5) containing 10 mM EDTA and 0.35 ml of 20% SDS were added, and the mixture was heated at 65° C. for 20 minutes. After phenol extractions (twice), DNA was precipitated with ethanol. The precipitate was dissolved in 2.5 ml of the above-mentioned 10 mM EDTA-containing buffer, then RNase A (ribonuclease) was added to a concentration of 4 μg/ml, and the mixture was maintained at 37° C. for 1 hour. Protease K was then added to a concentration of 100 μg/ml and the mixture was maintained at 37° C. for 2 hours. Following phenol extraction, DNA precipitation was caused with ethanol and the precipitate was dissolved in about 300 μl of TE buffer. The DNA solution was dialyzed against TE buffer.

Each DNA thus recovered was cleaved with the restriction enzymes BamHI and EcoRI and subjected to agarose gel (0.8%) electrophoresis, which was followed by DNA transcription from the electrophoretic gel to a nitrocellulose filter by the method of Southern (Molecular Cloning, pages 382–386, Cold Spring Harbor Laboratory, 1982). The pCPV22P DNA [cf. FIG. 3–6; derived from the vector pHSG298 by insertion of the P. diminuta V22-derived acylase gene (about 3-Kbp)] was cleaved with the restriction enzyme PstI and then $^{32}$P-labeled using a mixed primer labeling system (Clontech; imported and distributed by Toyobo). This labeled DNA and the above-mentioned DNA-bound nitrocellulose filter were subjected to Southern hybridization (Advanced Bacterial Genetics, pages 174–177, Cold Spring Harbor Laboratory, 1980).

While no hybridization was observed between the *A. chrysogenum* BC2116 DNA and pCPV22P, DNAs from the twelve hygromycin B-resistant transformants showed distinct hybridization. Furthermore, BamHI-cleaved DNAs from the acylase gene-containing strains *A. chrysogenum* Hm172, Hm155, Hm146, Hm154, Hm156, Hm161, Hm178 and Hm165 gave an hybrid band corresponding to the acylase gene of about 2.5 Kbp. These results indicate that the DNA in question was successfully introduced into hygromycin B-resistant transformants. Furthermore, the results of Southern hybridization indicate that the DNA introduced did not occur in a plasmid form but occurred integrated in the genomic DNA.

EXAMPLE 6

The 7ACA producing strain *Acremonium chrysogenum* Hm178 was cultivated in the same manner as in Example 5. The thus-obtained culture (1,000 ml) was centrifuged at 8,000 rpm for 5 minutes. The supernatant obtained was adjusted to pH 5.0 with 1N HCl (about 10 ml) and the resultant precipitate was removed by suction filtration. The filtrate (600 ml; 7ACA content: 136 µg/ml) was subjected to column chromatography using Diaion HP-20 (600 ml; Mitsubishi Kasei). After washing with 600 ml of acidified water (pH 3.5) and 600 ml of water (pH 7.0), elution was carried out with 30% aqueous isopropyl alcohol. The combined 7ACA-containing eluate fractions (1,200 ml) were concentrated at 30° C. under reduced pressure and the concentrate (60 ml) was applied to a YMC reversed-phase column (ODS A60 200/60 mesh, Yamamura Kagaku Kenkyusho; 1 liter). Development was carried out with water. 7ACA (39.8 mg) was eluted in fractions 360 ml to 1960 ml. The combined 7ACA-containing eluate fractions (1,600 ml) were concentrated to 114 ml at 30° C. under reduced pressure. Since this concentrate contained. CC in large excess relative to 7ACA, 5.4 ml of DAO [cf. Japanese Patent Application No. 1-266795 (266795/1989); 182 units/ml], 2 ml of catalase C-10 (Sigma; 10 mg/ml) and 13 ml of 1M phosphate buffer (pH 7.3) were added to the concentrate (114 ml) and the mixture was shaken at 25° C. for 1 hour for decomposing CC. The reaction mixture was adjusted to pH 1.5 with 1N HCl, then washed with an equal volume of ethyl acetate, and the aqueous layer obtained (127 ml; 7ACA: 21.6 mg) was concentrated to 50 ml at 30° C. under reduced pressure.

The concentrate was divided into two 25-ml portions and subjected to high performance liquid chromatography using two YMC reversed-phase columns equibrated in advance with 2% methanol-6.6 mM phosphate buffer (pH 7.3) (ODS packed column, R-354 S-15/30 µm, 50×300 mm×2 columns, Yamamura Kagaku Kenkyusho; UV detection: 254 nm). Development was carried out using the same solvent system as used in column eguilibration at a flow rate of 100 ml/min. The eluate was fractionated. 7ACA-containing fractions were combined (600 ml), adjusted to pH 5.0 with 1N HCl and subjected to column chromatography using Diaion HP-20 (60 ml), development being conducted with water (1,200 ml). 7ACA was eluted in fractions 600 ml to 1,600 ml. The 7ACA-containing fractions were combined and concentrated to dryness at 30° C. under reduced pressure to give 5.36 mg of 7ACA as a white powder. The $^1$H MNR, spectrum and IR spectrum of this product were in good agreement with those of a standard.

EXAMPLE 7

Hygromycin-B-resistant transformants were prepared by transforming *A. chrysogenum* BC2116 with pCYG-HB51 (Hm$^R$ alone), pHBV1 (vector for 7ACA and 7ADCA production), pHDV11 (vector for 7ACA and 7ADCA production) or pHBD3 (vector for GL-7ACA or GL-7ADCA production) in the same manner as described in Example 5 (cf. Table 2). These transformants Were each inoculated into 50 ml of CS1 medium placed in a 250-ml shaking flask and cultured at 30° C. for 4 days. One milliliter of this preculture was transferred to each of ten 250-ml shaking flasks containing 20 ml of the main culture medium. Shake culture (stroke: 3 inches; 250 rpm) was conducted at 25° C. for 3, 4, 5, 6 or 7 days. The main culture (two flasks for each culture period) was filtered through a Toyo No. 2 filter paper. A 100-µl portion of the filtrate was added to 900 µl of 0.1M phosphate buffer (pH 6.0) for dilution and assayed by HPLC-under the following conditions:

Column: Two columns connected, namely Cosmosil
    5C$_{18}$ column (4.6×150mm) (Nacalai
    Tesque) directly followed by Inertsil
    ODS-2 column (5×150 mm) (Gaskuro Kogyo)

Column temperature: 40° C.

Mobile phase: 2.2 mM tetra-n-butylammonium hydroxide,
    2.82 g/liter (NH$_4$)$_2$HPO$_4$
    (adjusted to pH 7.3 with phosphoric acid),
    5.63% methanol Rate of flow: 1 ml/min.

UV detection: 254 nm

Assaying under the above HPLC conditions gave the results shown in Table 2. In this assay, the positions of (retention times for) DCC, 7ADCA and GL-7ADCA were 5.5 minutes, 6.1 minutes and 26.9 minutes, respectively. As is evident from the results, transformants obtained with the plasmid pCYG-HB51 characterized by hygromycin B resistance alone produced neither 7ADCA nor. GL-7ADCA whereas transformants obtained with the 7ACA and 7ADCA production vector pHBV1 produced 7ADCA in an amount of about 24 µg/ml and transformants obtained with the GL-7ACA and GL-7ADCA production vector pHBD3 produced GL-7ACA in an amount of about 375 µg/ml. Furthermore, transformants obtained with the 7ACA and 7ADCA production vector pHDV11 containing both the D-amino acid oxidase and acylase genes produced 7ADCA in an amount of about 177 µg/ml and, in addition, the above-mentioned HPLC analysis revealed the simultaneous production of 7-amino-3-methyl-3-cephem-4-carboxylic acid by them (a small peak was found at a position corresonding to a retention time of 10 minutes).

TABLE 2

Production of 7ADCA and GL-7ADCA by *A. chrysogenum* BC2116-derived hygromycin B-resistant tranformants

| Strain No. | DNA used for transformation | Cultivation period (days) | pH | Yield 7ADCA (µg/ml) | GL-7ADCA (µg/ml) | DCC (mg/ml) |
|---|---|---|---|---|---|---|
| Hm144 | pCYG-HB51 | 3 | 6.5 | ND | ND | 0.23 |
|  |  | 4 | 6.8 | ND | ND | 0.73 |
|  |  | 5 | 7.2 | ND | ND | 1.45 |
|  |  | 6 | 8.3 | ND | ND | 2.38 |
|  |  | 7 | 8.3 | ND | ND | 3.13 |
| Hm172 | pHBV1 | 3 | 6.2 | ND | ND | 0.11 |
|  |  | 4 | 7.1 | ND | ND | 0.46 |
|  |  | 5 | 7.4 | ND | ND | 1.31 |
|  |  | 6 | 7.8 | 20 | ND | 2.07 |
|  |  | 7 | 8.1 | 24 | ND | 2.86 |
| Hm178 | pHDV11 | 3 | 6.4 | 11 | ND | 0.48 |
|  |  | 4 | 6.8 | 70 | 42 | 1.08 |
|  |  | 5 | 7.1 | 105 | 82 | 1.92 |
|  |  | 6 | 8.0 | 159 | 65 | 2.63 |
|  |  | 7 | 8.4 | 177 | 97 | 4.21 |
| Hm209 | pHBD3 | 3 | 6.2 | ND | ND | 0.18 |
|  |  | 4 | 6.9 | ND | 36 | 0.50 |
|  |  | 5 | 7.3 | ND | 190 | 1.35 |
|  |  | 6 | 8.2 | ND | 324 | 2.11 |
|  |  | 7 | 8.3 | ND | 375 | 2.88 |

ND: Not detected.

The following microorganisms have been deposited, since Dec. 25, 1989, with the Fermentation Research Institute, Agency of Industrial Science and Technology, Ministry of International Trade and Industry, Japan:

*Escherichia coli* JM109 (pCPV22P) FERM BP-2704
*Escherichia coli* JM109 (pHBV1) FERM BP-2703
*Escherichia coli* JM109 (pHDV11) FERM BP-2706
*Escherichia coli* JM109 (pHBD3) FERM BP-2705
*Acremonium chrysogenum* BC2116 FERM BP-2707

---

What is claimed is:

1. A method for producing a 7-aminocephem compound of the formula (I) or salt thereof:

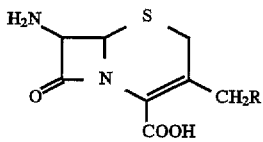

where R is acetoxy, hydroxy or hydrogen, comprising the steps of:

(i) cultivating a microorganism which has been transformed from a host microorganism to a transformed microorganism in a nutrient medium, wherein said host microorganism produces a cephalosporin compound of the formula (II):

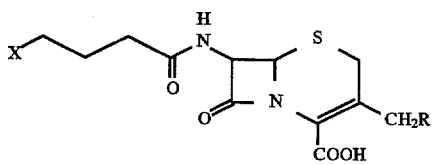

where R is defined above and X is —CH(NH₂)COOH, —CO—COOH or —COOH, and wherein said transformed microorganism contains a gene encoding an enzyme which converts said compound (II) to the corresponding 7-aminocephem compound (I); and (ii) recovering said compound of the formula (I) from the culture media.

2. The method according to claim 1, wherein said transformed microorganism is obtained by transforming a *Acremonium chrysogenum* with a vector comprising a gene encoding an enzyme which converts said compound (II) to the corresponding 7-aminocephem compound (I).

3. The method according to claim 2, wherein said *Acremonium chrysogenum* is selected from the group consisting of:

*Acremonium chrysogenum* BC 2116 (FERM BP 2707)

*Acremonium chrysogenum* (ATCC 11550),

*Acremonium chrysogenum* (ATCC 36225),

*Acremonium chrysogenum* (ATCC 20371),

*Acremonium chrysogenum* (ATCC 20416), and

*Acremonium chrysogenum* (ATCC 20427).

4. The method according to claim 2, wherein said gene capable of converting said compound (II) to the corresponding 7-aminocephem compound (I) is a cephalosporin C acylase gene.

5. The method according to claim 4, wherein said cephalosporin C acylase gene is isolated from *Pseudomonas sp.* SE83, *Pseudomonas putida* (ATCC 950) or *Pseudomonas diminuta* V22.

6. The method according to claim 4, wherein said vector further comprises one or more promoters for *Acremonium chrysogenum* located upstream from said cephalosporin C acylase gene.

7. The method according to claim 4, wherein said vector further comprises a D-amino acid oxidase gene.

8. The method according to claim 7, wherein said D-amino acid oxidase gene is isolated from *Trigonopsis variabilis* or *Fusarium solani* M-0718 (FERM-P 2688).

9. The method according to claim 7, wherein said vector further comprises one or more promoters for *Acremonium chrysogenum* located upstream from said cephalosporin C acylase gene and a D-amino acid oxidase gene.

10. The method according to claim 1, wherein the temperature of said cultivating step is about 30° C.

11. The method according to claim 1, wherein said cultivating step is conducted for about 100 to 170 hours.

* * * * *

UNITED STATES PATENT AND TRADEMARK OFFICE
CERTIFICATE OF CORRECTION

PATENT NO. : 5,677,141
DATED      : October 14, 1997
INVENTOR(S): Takao ISOGAI et al.

It is certified that error appears in the above-identified patent and that said Letters Patent is hereby corrected as shown below:

On the title page, Item [30], the first Foreign Application Number should read:

-- Dec. 27, 1989   [JP]   Japan ...... 1-342113 --

Signed and Sealed this

Ninth Day of December, 1997

Attest:

BRUCE LEHMAN

*Attesting Officer*   Commissioner of Patents and Trademarks